United States Patent
Allman

(10) Patent No.: US 10,683,549 B2
(45) Date of Patent: Jun. 16, 2020

(54) METHODS FOR ASSESSING RISK OF DEVELOPING BREAST CANCER

(71) Applicant: Genetic Technologies Limited, Fitzroy (AU)

(72) Inventor: Richard Allman, Wyndham Vale (AU)

(73) Assignee: GENETIC TECHNOLOGIES LIMITED, Fitzroy (AU)

(*) Notice: Subject to any disclaimer, the term of this patent is extended or adjusted under 35 U.S.C. 154(b) by 0 days.

(21) Appl. No.: 15/133,055

(22) Filed: Apr. 19, 2016

(65) Prior Publication Data
US 2016/0222469 A1 Aug. 4, 2016

Related U.S. Application Data

(63) Continuation of application No. PCT/AU2015/050583, filed on Sep. 25, 2015.

(30) Foreign Application Priority Data

Sep. 30, 2014 (AU) ................ 2014903898

(51) Int. Cl.
C12Q 1/6886 (2018.01)
C40B 40/06 (2006.01)

(52) U.S. Cl.
CPC ............ *C12Q 1/6886* (2013.01); *C40B 40/06* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | |
|---|---|---|
| 6,812,339 B1 | 11/2004 | Venter |
| 6,897,025 B2 | 5/2005 | Cox et al. |
| 6,955,883 B2 | 10/2005 | Margus et al. |
| 6,969,589 B2 | 11/2005 | Margus et al. |
| 7,124,033 B2 | 10/2006 | Hinds et al. |
| 7,127,355 B2 | 10/2006 | Cox et al. |
| 7,135,286 B2 | 11/2006 | Margus et al. |
| 7,427,480 B2 | 9/2008 | Margus et al. |
| 7,529,685 B2 | 5/2009 | Davies et al. |
| 9,051,617 B2 | 6/2015 | Cox |
| 9,068,229 B2 | 6/2015 | Cox et al. |
| 9,702,011 B2 | 7/2017 | Cox et al. |
| 10,407,738 B2 | 9/2019 | Cox et al. |
| 2002/0123095 A1 | 9/2002 | Kalush |
| 2003/0092019 A1 | 5/2003 | Meyer |
| 2003/0099964 A1 | 5/2003 | Patil |
| 2003/0108910 A1 | 6/2003 | Toland |
| 2003/0157488 A1 | 8/2003 | Cox |
| 2004/0002071 A1 | 1/2004 | Ralph |
| 2004/0023237 A1 | 2/2004 | Patil |
| 2004/0191783 A1 | 9/2004 | Leclercq |
| 2004/0210400 A1 | 10/2004 | Konvicka |
| 2004/0229224 A1 | 11/2004 | Frazer |
| 2004/0241657 A1 | 12/2004 | Patil |
| 2005/0003410 A1 | 1/2005 | Frazer |
| 2005/0019787 A1 | 1/2005 | Berno |
| 2005/0084849 A1 | 4/2005 | Moskowitz |
| 2005/0196770 A1 | 9/2005 | Cox |
| 2007/0037198 A1 | 2/2007 | Cox et al. |
| 2007/0166738 A1 | 7/2007 | Cox et al. |
| 2008/0131887 A1 | 6/2008 | Dietrich et al. |
| 2009/0087854 A1 | 4/2009 | Cox et al. |
| 2009/0208962 A1 | 8/2009 | Cox et al. |
| 2009/0239226 A1 | 9/2009 | Cox et al. |
| 2009/0239763 A1 | 9/2009 | Cox et al. |
| 2011/0015081 A1 | 1/2011 | Stacey |
| 2011/0015092 A1 | 1/2011 | Cox et al. |
| 2011/0200588 A1 | 8/2011 | Cox et al. |
| 2011/0294681 A1 | 12/2011 | Hinds |
| 2014/0018258 A1 | 1/2014 | Cox et al. |
| 2015/0354010 A1 | 12/2015 | Cox et al. |
| 2016/0371427 A1 | 12/2016 | Cox et al. |
| 2016/0371429 A1 | 12/2016 | Patil et al. |
| 2017/0275707 A1 | 9/2017 | Cox |
| 2018/0080089 A1 | 3/2018 | Hinds |
| 2018/0305764 A1 | 10/2018 | Allman |

FOREIGN PATENT DOCUMENTS

| | | |
|---|---|---|
| WO | WO 95/011995 | 5/1995 |
| WO | WO 98/020167 | 5/1998 |
| WO | WO 2003/025141 | 3/2003 |
| WO | WO 2005/014846 | 2/2005 |
| WO | WO 2005/024067 | 3/2005 |
| WO | WO 00/33161 | 6/2005 |
| WO | WO 2005/086770 | 9/2005 |
| WO | WO 2007/064776 | 6/2007 |
| WO | WO 2007/150044 | 12/2007 |
| WO | WO 2008/117314 | 10/2008 |
| WO | WO 2008/146309 | 12/2008 |
| WO | WO 2009/009752 | 1/2009 |
| WO | WO 2009/097270 | 8/2009 |
| WO | WO 2010/017520 | 2/2010 |
| WO | WO 2010/030929 | 3/2010 |
| WO | WO 2010/139006 | 9/2010 |
| WO | WO 2013/151413 | 10/2013 |
| WO | WO 2018/136995 | 8/2018 |
| WO | WO 2019/071322 | 4/2019 |

OTHER PUBLICATIONS

Dite et al. (Breast Cancer Res Treat., Jun. 2013,; 139(3): 887-896) (Year: 2013)*
Maxwell et al. (Breast Cancer Res. 2013; 15(6): 212, pp. 1-17; Pub. Date: Aug. 31, 2013). (Year: 2013).*
Dite et al. "Breast cancer risk prediction using clinical models and 77 independent risk-associated SNPs for women aged under 50 years: Australian Breast Cancer Family Registry." Cancer Epidemiology Biomarkers & Prevention 25.2 (2016): 359-365.

(Continued)

*Primary Examiner* — Pablo S Whaley
(74) *Attorney, Agent, or Firm* — Gary J. Gershik; Cooper & Dunham LLP

(57) ABSTRACT

The present disclosure relates to methods and systems for assessing the risk of a human female subject for developing breast cancer. In particular, the present disclosure relates to combining clinical risk assessment and genetic risk assessment to improve risk analysis.

19 Claims, 11 Drawing Sheets

Figure 1:
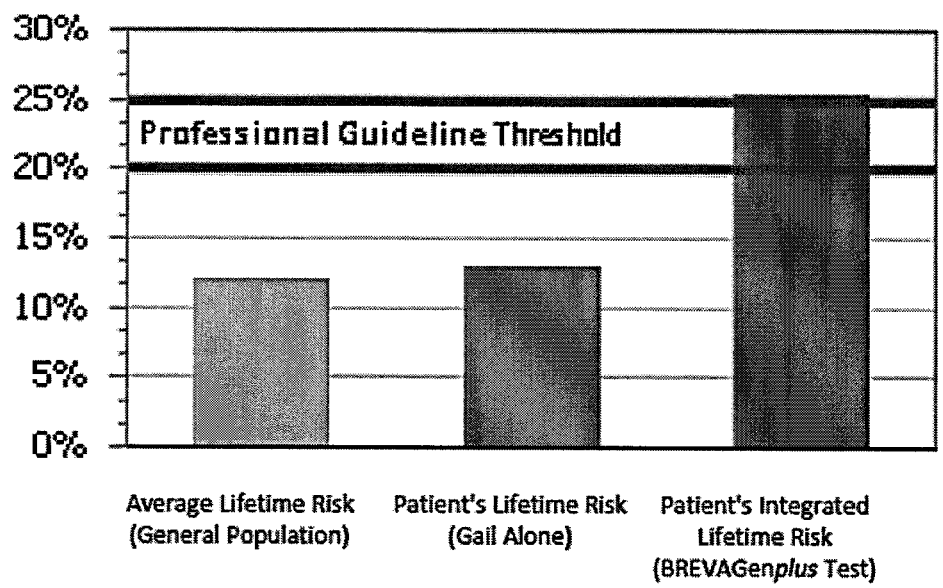

Specification includes a Sequence Listing.

(56) References Cited

OTHER PUBLICATIONS

Adami, et al. (1998) "Towards an understanding of breast cancer etiology" Cancer Biology 8:255-262 (Exhibit 1).
Adnane, et al. (1991) "BEK and FLG, two receptors to members of the FGF family, are amplified in subsets of human breast cancers" Onogene 6(4):659-663 (Exhibit 2).
AFD Eur panel-North America perlegen (www.ncbi.nlm.nih.gov/projects/SNP/snp_viewTable.cgi?pop=1371)(Exhibit 3).
Agami (2002) "RNAi and related mechanisms and their potential use for therapy" Curr Opin Chem Biol 6:829-834 (Exhibit 4).
Agúndez (2004) "Cytochrome P450 gene polymorphism and cancer." Current drug metabolism 5: 211-224 (Exhibit 5).
Amarzguioui et al. (2003) "Tolerance for mutations and chemical modifications in a siRNA" Nucl. Acids Res. 31:589-595 (Exhibit 6).
The Anglian breast cancer study group, (2000) "Prevalence and penetrance of BRCA1 and BRCA2 mutations in a population-based series of breast cancer cases" British Journal of Cancer 83(10):1301-1308 (Exhibit 7).
Antoniou, et al. (2003) "Average risks of breast and ovarian cancer associated with BRCA1 or BRCA2 mutations detected in case Series unselected for family history: a combined analysis of 22 studies" American Journal of Human Genetics 72:1117-1130 (Exhibit 8).
Antoniou, et al. (2001) "Evidence for further breast cancer susceptibility genes in addition to BRCA1 and BRCA2 in a population-based study" Genetic Epidemiology 21:1-18 (Exhibit 9).
Antoniou, et al. (2008) "Common Breast Cancer-Predisposition Alleles are Associated with Breast Cancer Risk in BRCA1 and BRCA2 Mutation Carriers" American Journal of Human Genetics 82:937-948 (Exhibit 10).
Bartel and Bartel (2003) "MicroRNAs: At the Root of Plant Development?" Plant Physiology 132:709-717 (Exhibit 11).
Beaucage and Iyer (1993) "The Synthesis of Modified Oligonucleotides by the Phosphoramidite Approach and Their Applications" Tetrahedron 49:6123 (Exhibit 12).
Becker et al. (1995) "Combined mapping of AFLP and RFLP markers in barley" Mol Gen Genet 249:65 (Exhibit 13).
Bird (1988) "Single-Chain Antigen-Binding Proteins" Science 242:423-426 (Exhibit 14).
The Breast Cancer Association Consortium (2006) "Commonly Studied Single-Nucleotide Polymorphisms and Breast Cancer: Results from the Breast Cancer Association Consortium" Journal of National Cancer Institute 98:1382-1896 (Exhibit 15).
Campbell, Ian G., James Allen, and Diana M. Eccles. "Prohibitin 3' untranslated region polymorphism and breast cancer risk." Cancer Epidemiology Biomarkers & Prevention 12.11 (2003) : 1273-1274 (Exhibit 16).
Canzian, F., et al. (2006) "Polymorphisms of genes coding for insulin-like growth factor 1 and its major binding proteins, circulating levels of IGF-1 and IGFBP-3 and breast cancer risk: results from EPIC study" British Journal of Cancer 94:299-307 (Exhibit 17).
Caplen et al. (2001) "Specific inhibition of gene expression by small double-stranded RNAs in invertebrate and vertebrate systems" Proc. Natl. Acad. Sci. USA 98:9742-9747 (Exhibit 18).
Carlson, et al. (2004) "Selecting a maximally informative set of single-nucleotide polymorphisms for association analyses using linkage disequilibrium" American Journal of Human Genetics 74:106-120 (Exhibit 19).
Chapman, et al. (2003) "Detecting disease associations due to linkage disequilibrium using haplotype tags: a class of tests and the determinants of statistical power" Human Heredity 56: 18-31 (Exhibit 20).
CHEK 2 Breast Cancer consortium (2002) "Low-penetrance susceptibility to breast cancer due to CHEK2(*)1100delC in noncarriers of BRCA1 or BRCA2 mutations" Nature Genetics 31: 55-59 (Exhibit 21).
Chlebowski, R., et al. (2002) "American Society of Clinical Oncology Technology Assessment of Pharmacologic Interventions for Breast Cancer Risk Reduction Including Tamoxifen, Raloxifene, and Aromatase Inhibition" Journal of Clinical Oncology 20(15):3328-3343 (Exhibit 22).
Cote et al. (1983) "Specific inhibition of gene expression by small double-stranded RNAs in invertebrate and vertebrate systems" Proc. Natl. Acad. Sci. USA 80:2026-2030 (Exhibit 23).
Cox, A., et al. (2007) "A common coding variant in CASP8 is associated with breast cancer risk" Nature Genetics 39(3):352-358 (Exhibit 24).
Cui, et al. (2001) "After BRCA1 and BRCA2—what next? Multifactorial segregation analyses of three-generation, population-based Australian families affected by female breast cancer" American Journal of Human Genetics 68:420-431 (Exhibit 25).
Czauderna et al. (2003) "Structural variations and stabilising modifications of synthetic siRNAs in mammalian cells" Nucl Acids Res 31:2705-2716 (Exhibit 26).
Day, et al. (1999) "EPIC-Norfolk: study design and characteristics of the cohort" British Journal of Cancer 80(1):95-103 (Exhibit 27).
Deloukas et al. (2004) "The DNA sequence and comparative analysis of human chromosome 10" Nature, 429: 375-381 (Exhibit 28).
Dite, G. et al., "Value of adding single-nucleotide polymorphism panel markers to phenotypic algorithms of breast cancer risk", Cancer Research, May 2015, vol. 75, No. 9 suppl. 1, abstract No. P6-09-05 (Exhibit 29).
Dite et al. "Breast cancer risk prediction using clinical models and 77 independent risk-associated SNPs for women aged under 50 years: Australian Breast Cancer Family Registry." Cancer Epidemiology Biomarkers & Prevention 25.2 (2016): 359-365 (Exhibit 30).
Doench and Sharp (2004) "Specificity of microRNA target selection in translational repression" Genes & Dev. 18:504-511 (Exhibit 31).
Doench et al. (2003) "siRNAs can function as miRNAs" Genes & Dev. 17:438-442 (Exhibit 32).
Dunning, et al. (1999) "A systematic review of genetic polymorphisms and breast cancer risk" Cancer Epidemiology Biomarkers & Prevention 8:843-854 (Exhibit 33).
Dunning, et al. (2003) "A Transforming Growth Factor 1 Signal Peptide Variant Increases Secretion inVitro and Is Associated with Increased Incidence of Invasive Breast Cancer" Cancer Research 63:2610-2615 (Exhibit 34).
Dunning, et al. (2004) "Polymorphisms Associated With Circulating Sex Hormone Levels in Postmenopausal Women" Journal of National Cancer Institute 96(12):936-945 (Exhibit 35).
Dykxhoorn et al. (2003) "Killing the Messenger: Short RNAs that Silence Gene Expression" Nature Reviews Molec. and Cell Biol. 4:457-467 (Exhibit 36).
Easton (1999) "How many more breast cancer predisposition genes are there?" Cancer Research 1:1-4 (Exhibit 37).
Elbashir et al. (2001) "Duplexes of 21-nucleotide RNAs mediate RNA interference in cultured mammalian cells" Nature 411:494-498 (Exhibit 38).
Elbashir et al. (2002) "Analysis of gene function in somatic mammalian cells using small interfering RNAs" Methods 26:199-213 (Exhibit 39).
Fibroblast growth factor receptor 2, bacteria-expressed kinase, keratino dysostosis 1, crouzon syndrome, Pfeiffer syndrome, gene card for FGFR2, GC10M122473, pp. 1-17, available at www.genecards.org/cgi-din/carddisp.pl?gene=FGFR@&search=FGFR (Exhibit 40).
Finnegan et al. (1996) "Reduced DNA methylation in *Arabidopsis thaliana* results in abnormal plant development" Proc Natl Acad Sci USA 93:8449-8454 (Exhibit 41).
Ford, et al. (1998) "Genetic Heterogeneity and Penetrance Analysis of the BRCA1 and BRCA2 Genes in Breast Cancer Families" American Journal of Human Genetics 62:676-689 (Exhibit 42).
Goodchild (1990) "Conjugates of Oligonucleotides and Modified Oligonucleotides: A Review of Their Synthesis and Properties" Bioconjugate Chem. 1:165 (Exhibit 43).
Goode, et al. (2001) Genetic Epidemiology 126: p. 155 (Exhibit 44).

(56) References Cited

OTHER PUBLICATIONS

Hanks, et al (2003) Genome Biology vol. 4, p. 11 published Apr. 29, 2003 (Exhibit 45).
Hannon (2002) "RNA interference" Nature 418:244 30:251 (Exhibit 46).
Healey, et al. (2000) "A common variant in BRCA2 is associated with both breast cancer risk and prenatal viability" Nature Genetics 26:362-364 (Exhibit 47).
Heiskanen, et al. (2001) "CGH, cDNA and tissue microarray analyses implicate FGFR2 amplification in a small subset of breast tumors" Analytical Cellular Pathology 22: 229-234 (Exhibit 48).
Hinds, et al. (2005) "Whole-genome patterns of common DNA variation in three human populations" Science 307:1072-1079 (Exhibit 49).
Hirschhorn et al. (Genetics in Medicine. vol. 4, No. 2, pp. 45-61, Mar. 2002) (Exhibit 50).
Holen et al. (2003) "Similar behaviour of single-strand and double-strand siRNAs suggests they act through a common RNAi pathway" Nucl. Acids Res. 31:2401-2407 (Exhibit 51).
Hunter et al. (2007) "A genome-wide association study identifies alleles in FGFR2 associated with risk of sporadic postmenopausal breast cancer" Nature Genetics (2007) 39(6):870-874 (Exhibit 52).
Huse et al. (1989) "Generation of a Large Combinatorial Library of the Immunoglobulin Repertoire in Phage Lambda" Science 246:1275-1281.(Exhibit 53).
Huston et al. (1988) "Protein engineering of antibody binding sites: Recovery of specific activity in an anti-digoxin single-chain Fv analogue produced in *Escherichia coli*" Proc. Natl. Acad. Sci. USA 85:5879-5883 (Exhibit 54).
Hutvagner and Zamore (2002) "RNAi: nature abhors a double-strand" Curr Opin Genet & Dev 200:225-232 (Exhibit 55).
Huusko, et al. (2004) "Genome-wide scanning for linkage in Finnish breast cancer families" European Journal of Human Genetics 12: 98-104 (Exhibit 56).
Huusko, "Genome-wide scanning for linkage in Finnish breast cancer families" European Journal of Human Genetics 12:256 (2003) (Exhibit 57).
Ioannidis (2001) "Replication validity of genetic association studies" Nature Genetics 29:306-309 (Exhibit 58).
Ishibe et al. (1998) Cancer Research 58: 667-671 (Exhibit 59).
Issaq et al. (2003) "SELDI-TOF MS for Diagnostic Proteomics" Analytical Chemistry 75:149A-155A (Exhibit 60).
Kohno et al (2001), Medical Online 6:25-31* (Exhibit 61).
Jang, et al. (2001) "Mutations in Fibroblast growth factor receptor 2 and fibroblast growth factor receptor 3 genes associated with human gastric and colorectal cancers" Cancer Research 61: 3541-3543 (Exhibit 62).
Jorde (2000) "Linkage Disequilibrium and the Search for Complex Disease Genes" Genome Research 10:1435-1444 (Exhibit 63).
Kamali-Sarvestani, et al. (2005) "Polymorphism in genes of alpha and beta tumor necrosis factors (TNF-α and TNG-β) and gamma interferon (IFN-γ) among Iranian women and breast cancer" Cancer Letters 223(1): 113-119 (Exhibit 64).
Kalemi, et al. (2005) "The association of p53 mutations and p53 codon 72, Her 2 codon 655 and MTHFR C677T polymorphisms with breast cancer in Northern Greece" Cancer Letters 222(1): 57-65 (Exhibit 65).
Katoh & Katoh, (2003) "FGFR2 and WDR11 are neighboring oncogene and tumor suppressor gene on human chromosome 10q26" International Journal of Oncology 22:1155-2737 (Exhibit 66).
Kawasaki and Taira (2004) "Induction of DNA methylation and gene silencing by short interfering RNAs in human cells" Nature 431:211-217 (Exhibit 67).
Kim et al. (2005) "Synthetic dsRNA Dicer substrates enhance RNAi potency and efficacy" Nature Biotechnology 23:222-226 (Exhibit 68).
Kohler and Milstein (1975) "Continuous cultures of fused cells secreting antibody of predefined specificity" Nature 256:495-497 (Exhibit 69).
Kosbor et al. (1983) "The production of monoclonal antibodies from human lymphocytes" Immunology Today 4:72 (Exhibit 70).
Kuschel, et al. (2002) "Variants in DNA double-strand break repair genes and breast cancer susceptibility" Human Molecular Genetics 11(12):1399-1407 (Exhibit 71).
Laan et al. (1997) Nature Genetics 17:435-438(Exhibit 72).
Lee, et al. (2005) "Genetic polymorphisms of ataxia telangiectasia mutated and breast cancer risk" Cancer Epidemiology, Biomarkers & Prevention 14(4):821-825 (Exhibit 73).
Lee et al. (2008) "The Role of Established Breast Cancer Susceptibility Loci in Mammographic Density in Young Women" Cancer, Epidemiology, Biomarkers & Prevention 17:258-260 (Exhibit 74).
Lesueur et al. (2005) "Allelic association of the human homologue of the mouse modifier Ptprj with breast cancer" Human Molecular Genetics 14:2349 (Exhibit 75).
Lichtenstein, et al. (2000) "Environmental and Heritable Factors in the Causation of Cancer—Analyses of Cohorts of Twins from Sweden, Denmark, and Finland" New England Journal of Medicine 343(2):78-85 (Exhibit 76).
Listgarten et al. (2004) "Predictive Models for Breast Cancer Susceptibility from Multiple Single Nucleotide Polymorphisms" Clinical Cancer Research 10(8):2725-2737 (Exhibit 77).
Martinez et al. (2002) "Single-Stranded Antisense siRNAs Guide Target RNA Cleavage in RNAi" Cell 110:563-574 (Exhibit 78).
Mattick and Makunin (2005) "Small regulatory RNAs in mammals" Hum. Mol. Genet. 14:R121-R132 (Exhibit 79).
McManus (2003) "MicroRNAs and cancer" Semin Cancer Biol. 13:253-288 (Exhibit 80).
McManus and Sharp (2002) "Gene Silencing in Mammals by Small Interfering RNAs" Nature Reviews Genetics 3:737-747 (Exhibit 81).
Meister et al. (2004) "Sequence-specific inhibition of microRNA and siRNA-induced RNA silencing" RNA 10:544-550 (Exhibit 82).
Meksem et al. (1995) "A high-resolution map of the vicinity of the R1 locus on chromosome V of potato based on RFLP and AFLP markers" Mol Gen Genet 249:74 (Exhibit 83).
Millikan et al. (Cancer Epidemiology, Biomarkers and Prevention 2005 vol. 14 p. 2326) (Exhibit 84).
Moffa, et al. (2004) "Transforming potential of alternatively spliced variants of fibroblast growth factor receptor 2 in human mammary epithelial cells" Molecular Cancer Research 2(11): 643-652 (Exhibit 85).
Morris et al. (2004) "Small Interfering RNA-Induced Transcriptional Gene Silencing in Human Cells" Science 305:1289-1292 (Exhibit 86).
Morrison et al. (1984) "Chimeric human antibody molecules: Mouse antigen-binding domains with human constant region domains" Proc. Natl. Acad. Sci. USA 81:6851-6855 (Exhibit 87).
Nelson et al. (2003) "The microRNA world: small is mighty" Trends Biochem. Sci. 28:534-540 (Exhibit 88).
U.S. Appl. No. 10/970,761, filed Oct. 20, 2004, Frazer.
U.S. Appl. No. 60/566,302, filed Apr. 28, 2004, Cox.
U.S. Appl. No. 60/590,534, filed Jul. 22, 2004, Cox.
May 5, 2011 Office Action issued in connection with U.S. Appl. No. 12/890,272 (Exhibit 1).
Jun. 3, 2011 Response filed in connection with U.S. Appl. No. 12/890,272 (Exhibit 2).
Jul. 8, 2011 Response, filed in connection with U.S. Appl. No. 12/890,272 (Exhibit 3).
Sep. 29, 2011 Office Action issued in connection with U.S. Appl. No. 12/890,272 (Exhibit 4).
Mar. 29, 2012 Response filed in connection with U.S. Appl. No. 12/890,272 (Exhibit 5).
Apr. 2, 2012 Applicant-Initiated Interview Summary issued in connection with U.S. Appl. No. 12/890,272 (Exhibit 6).
Apr. 23, 2012 Office Action issued in connection with U.S. Appl. No. 12/890,272 (Exhibit 7).
May 24, 2012 Response filed in connection with U.S. Appl. No. 12/890,272 (Exhibit 8).
May 24, 2012 Applicant-Initiated Interview Summary issued in connection with U.S. Appl. No. 12/890,272 (Exhibit 9).
Jun. 1, 2012 Response filed in connection with U.S. Appl. No. 12/890,272 (Exhibit 10).

(56) References Cited

OTHER PUBLICATIONS

Jun. 1, 2012 Advisory Action issued in connection with U.S. Appl. No. 12/890,272 (Exhibit 11).
Jun. 26, 2012 Response filed in connection with U.S. Appl. No. 12/890,272 (Exhibit 12).
Aug. 23, 2012 Office Action issued in connection with U.S. Appl. No. 12/890,272 (Exhibit 13).
Nov. 16, 2012 Applicant-Initiated Interview Summary, including attached Oct. 26, 2012 facsimile, issued in connection with U.S. Appl. No. 12/890,272 (Exhibit 14).
Nov. 21, 2012 Response filed in connection with U.S. Appl. No. 12/890,272 (Exhibit 15).
Jan. 9, 2013 Office Action issued in connection with U.S. Appl. No. 12/890,272 (Exhibit 16).
Feb. 13, 2013 Applicant-Initiated Interview Summary issued in connection with U.S. Appl. No. 12/890,272 (Exhibit 17).
Mar. 8, 2013 Response filed in connection with U.S. Appl. No. 12/890,272 (Exhibit 18).
Mar. 5, 2013 Applicant-Initiated Interview Summary, including attached Proposed Amendments to the Claims, issued in connection with U.S. Appl. No. 12/890,272 (Exhibit 19).
Jun. 20, 2013 Advisory Action issued in connection with U.S. Appl. No. 12/890,272 (Exhibit 20).
Dec. 18, 2013 Office Action issued in connection with U.S. Appl. No. 12/890,272 (Exhibit 21).
Feb. 4, 2014 Applicant-Initiated Interview Summary issued in connection with U.S. Appl. No. 12/890,272 (Exhibit 22).
Feb. 21, 2014 Response filed in connection with U.S. Appl. No. 12/890,272 (Exhibit 23).
Oct. 20, 2014 Office Action issued in connection with U.S. Appl. No. 12/890,272 (Exhibit 24).
Dec. 5, 2014 Applicant-Initiated Interview Summary issued in connection with U.S. Appl. No. 12/890,272 (Exhibit 25).
Jan. 12, 2015 Response filed in connection with U.S. Appl. No. 12/890,272 (Exhibit 26).
Apr. 24, 2015 Notice of Allowance issued in connection with U.S. Appl. No. 12/890,272 (Exhibit 27).
Jun. 11, 2012 Office Action issued in connection with U.S. Appl. No. 12/920,815 (Exhibit 28).
Jul. 11, 2012 Response filed in connection with U.S. Appl. No. 12/920,815 (Exhibit 29).
Sep. 21, 2012 Office Action issued in connection with U.S. Appl. No. 12/920,815 (Exhibit 30).
Feb. 21, 2013 Response filed in connection with U.S. Appl. No. 12/920,815 (Exhibit 31).
Jun. 24, 2013 Office Action issued in connection with U.S. Appl. No. 12/920,815 (Exhibit 32).
Dec. 23, 2013 Response filed in connection with U.S. Appl. No. 12/920,815 (Exhibit 33).
Apr. 20, 2015 Office Action issued in connection with U.S. Appl. No. 12/920,815 (Exhibit 34).
Oct. 20, 2015 Response filed in connection with U.S. Appl. No. 12/920,815 (Exhibit 35).
Jun. 14, 2016 Office Action issued in connection with U.S. Appl. No. 12/920,815 (Exhibit 36).
Dec. 14, 2016 Response filed in connection with U.S. Appl. No. 12/920,815 (Exhibit 37).
Jun. 19, 2017 Office Action issued in connection with U.S. Appl. No. 12/920,815 (Exhibit 38).
May 23, 2017 Supplemental Response filed in connection with U.S. Appl. No. 12/920,815 (Exhibit 39).
Mar. 22, 2017 Applicant-Initiated Interview Summary issued in connection with U.S. Appl. No. 12/920,815 (Exhibit 40).
Mar. 11, 2016 Supplemental Response filed in connection with U.S. Appl. No. 12/920,815 (Exhibit 41).
Mar. 7, 2016 Examiner-Initiated Interview Summary issued in connection with U.S. Appl. No. 12/920,815 (Exhibit 42).
Jan. 20, 2016 Examiner-Initiated Interview Summary issued in connection with U.S. Appl. No. 12/920,815 (Exhibit 43).
Dec. 18, 2015 Summary of Nov. 12, 2015 Examiner Interview filed in connection with U.S. Appl. No. 12/920,815 (Exhibit 44).
Nov. 18, 2015 Applicant-Initiated Interview Summary issued in connection with U.S. Appl. No. 12/920,815 (Exhibit 45).
Feb. 4, 2013 Applicant-Initiated Interview Summary issued in connection with U.S. Appl. No. 12/920,815 (Exhibit 46).
Jun. 7, 2016 Office Action, issued in connection with U.S. Appl. No. 14/738,639 (Exhibit 47).
Nov. 16, 2016 Response, filed in connection with U.S. Appl. No. 14/738,639 (Exhibit 48).
Dec. 1, 2016 Interview Summary, issued in connection with U.S. Appl. No. 14/738,639 (Exhibit 49).
Feb. 28, 2017 Summary of Examiner Interview and Communication Forwarding Terminal Disclaimer, filed in connection with U.S. Appl. No. 14/738,639 (Exhibit 50).
Mar. 7, 2017 Notice of Allowance, issued in connection with U.S. Appl. No. 14/738,639 (Exhibit 51).
Jun. 7, 2010 Office Action, issued in connection with U.S. Appl. No. 12/370,972 (Exhibit 52).
Dec. 6, 2010 Response, filed in connection with U.S. Appl. No. 12/370,972 (Exhibit 53).
Feb. 2, 2011 Final Office Action, issued in connection with U.S. Appl. No. 12/370,972 (Exhibit 54).
Jul. 5, 2011 Notice of Appeal, filed in connection with U.S. Appl. No. 12/370,972 (Exhibit 55).
Nov. 7, 2011 Response, filed in connection with U.S. Appl. No. 12/370,972 (Exhibit 56).
Jul. 18, 2013 Response, filed in connection with U.S. Appl. No. 12/370,972 (Exhibit 57).
Feb. 4, 2014 Applicant-Initiated Interview Summary issued in connection with U.S. Appl. No. 12/370,972 (Exhibit 58).
Feb. 21, 2014 Response, filed in connection with U.S. Appl. No. 12/370,972 (Exhibit 59).
Oct. 17, 2014 Office Action, issued in connection with U.S. Appl. No. 12/370,972 (Exhibit 60).
Dec. 8, 2014 Interview Summary, issued in connection with U.S. Appl. No. 12/370,972 (Exhibit 61).
Jan. 12, 2015 Response, filed in connection with U.S. Appl. No. 12/370,972 (Exhibit 62).
Apr. 10, 2015 Notice of Allowance, issued in connection with U.S. Appl. No. 12/370,972 (Exhibit 63).
Jun. 16, 2005 Response, filed in connection with U.S. Appl. No. 10/631,415 (Exhibit 64).
PCT International Search Report dated Dec. 6, 2007 in connection with PCT International Application No. PCT/US2006/045812, filed Nov. 29, 2006 (Exhibit 2).
English language translation of Israeli Office Action dated Jul. 14, 2010 in connection with Israeli Patent Application No. 191566 (Exhibit 8).
Response filed to Israeli Office Action filed Nov. 9, 2010 in connection with Israeli Patent Application No. 191566, including English language translation of transmittal letter (Exhibit 9).
Israeli Office Action dated Jun. 1, 2011 in connection with Israeli Patent Application No. 191566 (Exhibit 10).
Response filed to Israeli Office Action filed Oct. 2, 2011 in connection with Israeli Patent Application No. 191566 (Exhibit 11).
English language translation of Israeli Office Action issued Feb. 29, 2012 in connection with Israeli Patent Application No. 191566 (Exhibit 12).
English language translation of Response filed to Israeli Office Action dated Jun. 20, 2012 in connection with Israeli Patent Application No. 191566 (Exhibit 13).
European Search Opinion dated Oct. 13, 2009 in connection with European Patent Application No. 06838661.4 (Exhibit 14).
Response to Examination report of Feb. 12, 2010 in connection with European Patent Application No. 06838661.4 (Exhibit 15).
Response filed to European Examination Report filed Aug. 23, 2010 in connection with European Patent Application No. 06838661.4 (Exhibit 16).
Examination Report dated Feb. 17, 2012 in connection with European Patent Application No. 06838661.4 (Exhibit 17).

(56) References Cited

OTHER PUBLICATIONS

Response filed to European Examination Report on Feb. 22, 2012 in connection with European Patent Application No. 06838661.4 (Exhibit 18).
Apr. 9, 2018 Extended European Search Report issued by the European Patent Office (EPO) in connection with European Patent Application No. 15847907.1 (Exhibit 19).
Kaklamani et al. (2013) "Adiponectin pathway polymorphisms and risk of breast cancer in African Americans and Hispanics in the Women's Health Initiative", Breast Cancer Res Treat. 139(2):461-468 (Exhibit 20).
Australian Examiner's Report dated Jun. 29, 2011 in connection with Australian Application No. 2006320559 (Exhibit 21).
Response filed to Australian Examiner's Report filed on Oct. 18, 2011 in connection with Australian Application No. 2006320559 (Exhibit 22).
Second Australian Examiner's Report dated Nov. 17, 2011 in connection with Australian Application No. 2006320559 (Exhibit 23).
Response filed to Second Australian Examiner's Report filed Dec. 7, 2011 in connection with Australian Application No. 2006320559 (Exhibit 24).
English language translation of Notice from Chinese Patent Office dated Jun. 1, 2011 in connection with Chinese Patent Application No. 200680051710.0 (Exhibit 25).
Response filed to Chinese Notice dated Jul. 25, 2011 in connection with Chinese Patent Application No. 200680051710.0, including English Language claims (Exhibit 26).
English language translation of First Chinese Office Action dated Oct. 13, 2011 in connection with Chinese Patent Application No. 200680051710.0 (Exhibit 27).
Response filed to First Chinese Office Action dated Feb. 9, 2012 in connection with Chinese Patent Application No. 200680051710.0, including English Language claims (Exhibit 28).
English language translation of Second Chinese Office Action in connection with Chinese Patent Application No. 200680051710.0 (Exhibit 29).
Japanese Office Action dated Feb. 22, 2012 in connection with Japanese Patent Application No. 2008-543446, including English language translation (Exhibit 30).
Response filed to Japanese Office Action dated Aug. 24, 2012 in connection with Japanese Patent Application No. 2008-543446, including English Language claims (Exhibit 31).
Japanese Patent Application Publication No. JP 2005/532780, published Nov. 4, 2005 (Ralph et al.), corresponding to PCT International Publication No. WO 2003/025141 (Exhibit 32).
Japanese Patent Application Publication No. JP 2001/503276, published Mar. 13, 2001 (Jupe et al.) corresponding to PCT International Publication No. WO 1998/20167 (Exhibit 33).
Neuberger et al. (1984) "Recombinant antibodies possessing novel effector functions" Nature 312:604-608 (Exhibit 34).
Nishikura (2001) "A Short Primer on RNAi: RNA-Directed RNA Polymerase Acts as a Key Catalyst" Cell 107:415-418 (Exhibit 35).
Patil, et al. "Blocks of Limited Haplotype Diversity Revealed by High-Resolution Scanning of Human Chromosome 21" (2001) Science 294(5547):1719-1723 (Exhibit 36).
Peto, et al. (1999) "Prevalence of BRCA1 and BRCA2 Gene Mutations in Patients With Early-Onset Breast Cancer" Journal of the National Cancer Institute 91(11):943-949 (Exhibit 37).
Pharoah, et al. (2002) "Polygenic susceptibility to breast cancer and implications for prevention" Nature Genetics 31:33-36 (Exhibit 38).
Pritchard, et al. (2001) "Linkage disequilibrium in humans: models and data" American Journal of Human Genetics 69:1-14 (Exhibit 39).
Radford et al. (1995) Cancer Resarch (55) pp. 5180-5183 (Exhibit 40).
Rehmsmeier et al. (2004) "Fast and effective prediction of microRNA/target duplexes" RNA 10:1507-1517 (Exhibit 41).
Robins et al. (2005) "Incorporating structure to predict microRNA targets" Proc. Natl. Acad. Sci. 102:4006-4009 (Exhibit 42).
Sasieni (1997) "From genotypes to genes: doubling the sample size" Biometrics 53(4):1253-1261 (Exhibit 43).
Satagopan, et al., (2002) "Two-stage designs for gene-disease association studies" Biometrics 58:163-170 (Exhibit 44).
Scacheri et al. (2004) "Short interfering RNAs can induce unexpected and divergent changes in the levels of untargeted proteins in mammalian cells" Proc. Natl. Acad. Sci. USA 101:1892-1897 (Exhibit 45).
Schmith et al. (2003) "Pharmacogenetics and disease genetics of complex diseases" CMLS Cell. Mol. Life Sci. 60:1636-1646) (Exhibit 46).
Schramke and Allshire (2003) "Hairpin RNAs and Retrotransposon LTRs Effect RNAi and Chromatin-Based Gene Silencing" Science 301:1069-1074 (Exhibit 47).
Schwarz et al. (2002) "Evidence that siRNAs Function as Guides, Not Primers, in the *Drosophila* and Human RNAi Pathways" Mol. Cell 10:537-548 (Exhibit 48).
Schwarz and Zamore (2002) "Why do miRNAs live in the miRNP?" Genes & Dev. 16:1025-1031 (Exhibit 49).
Sempere et al. (2004) "Expression profiling of mammalian microRNAs uncovers a subset of brain-expressed microRNAs with possible roles in murine and human neuronal differentiation" Genome Biology 5:R13 (Exhibit 50).
Siolas et al. (2005) "Synthetic shRNAs as potent RNAi Triggers" Nature Biotechnology 23:227-231 (Exhibit 51).
Sprecher Institute "Breast Cancer in Women from Different Racial/Ethnic Groups Fact Sheet #47" Apr. 2003 envirocancer.cornell.edu/Factsheet/general/fs47.ethnicity.cfm (Exhibit 52).
Spurdle, Amanda B., et al. "Prohibitin 3' untranslated region polymorphism and breast cancer risk in Australian women." The Lancet 360.9337 (2002): 925-926 (Exhibit 53).
Stankovic, et al. (1998) "ATM mutations and phenotypes in ataxia-telangiectasia families in the British Isles: expression of mutant ATM and the risk of leukemia, lymphoma, and breast cancer" American Journal of Human Genetics 62:334-345 (Exhibit 54).
Stark et al. (2003) "Identification of *Drosophila* MicroRNA Targets" PLoS Biol. 1:E60 (Exhibit 55).
Stephens, et al. (2005) "A screen of the complete protein kinase gene family identifies diverse patterns of somatic mutations in human breast cancer" Nature Genetics 37:590-592 and supplemental information (Exhibit 56).
Takashi et al. (2001) "3. Byouti Kaiseki to SNP 1 Gan (Pathologic Analysis and SNP, 1 Cancer)", Ketsueki/Meneki/Shuyou, 6(4):353-359 (Exhibit 57).
Takeda et al. (1985) "Construction of chimaeric processed immunoglobulin genes containing mouse variable and human constant region sequences" Nature 314:452-454 (Exhibit 58).
Tang et al. (2003) "A biochemical framework for RNA silencing in plants" Genes & Dev. 17:49-63 (Exhibit 59).
Tang et al. (2005) "Genetic structure, self-identified race. Ethnicity and confounding in case-control association studies" Am. J. Hum. Genet. 76(2):268-275 (Exhibit 60).
Tannheimer, et al. (2000) "Characterization of fibroblast growth factor receptor 2 overexpression in the human breast cancer cell line SUM-52PE" Breast Cancer Research 2:311-320 (Exhibit 61).
Thompson, et al. (2002) "Evaluation of linkage of breast cancer to the putative BRCA3 locus on chromosome 13q21 in 128 multiple case families from the Breast Cancer Linkage Consortium" Proceedings of the National Academy of Sciences USA 99(2):827-831 (Exhibit 62).
Tischkoff, et al. (2004) "Implications of biogeography of human populations for 'race' and medicine" Nature Genetics 36:s21-s27 (Exhibit 63).
Titus-Ernstoff, et al. (1998) "Menstrual factors in relation to breast cancer risk" Cancer Epidemiology, Biomarkers & Prevention 7:783-789 (Exhibit 64).
Tuschl and Borkhardt (2002) "Small Interfering RNAs: A revolutionary Tool for the Analysis of Gene Function and Gene Therapy" Molecular Interventions 2:158-167 (Exhibit 65).
Uhlmann and Peyman (1990) "Antisense Oligonucleotides: A New Therapeutic Principle" Chem. Rev. 90:543 (Exhibit 66).

(56) References Cited

OTHER PUBLICATIONS

Van't Veer et al. (2002) "Gene expression profiling predicts clinical outcome of breast cancer" Nature: International Weekly Journal of Science 415(6871):530-536 (Exhibit 67).

Van de Vijver et al. (2002) "A Gene-expression signature as a predictor of survival in breast cancer" New England Journal of Medicine 347(25): 1999-2009 (Exhibit 68).

Vos et al. (1995) "AFLP: a new technique for DNA fingerprinting" Nucl Acids Res 23:4407 (Exhibit 69).

Wang et al. (2004) Cancer Research 64:64-71 (Exhibit 70).

Ward et al. (1989) "Binding activities of repertoire of single immunoglobulin variable domains secreted from *Echerichia coli*" Nature 334:544-546 (Exhibit 71).

Wall, et al. (2003) "Haplotype blocks and linkage disequilibrium in the human genome" Nature Reviews Genetics 4:587-597 (Exhibit 72).

Zamore (2001) "RNA interference: listening to the sound of silence" Nature Structural Biology 8:746-750 (Exhibit 73).

Zeng et al. (2003) "MicroRNAs and small interfering RNAs can inhibit mRNA expression by similar mechanisms" Proc. Natl. Acad. Sci. USA 100:9779-9784 (Exhibit 74).

Zhang, et al. (2002) "A dynamic programming algorithm for haplotype block partitioning" Proceedings of the National Academy of Sciences USA 99(11):7335-7339 (Exhibit 75).

*Enfish, LLC* v. *Microsoft Corp.*, No. 2015-1244 (Fed. Cir. May 12, 2016) (Exhibit 76).

NCBI Database ss22777675, https://www.ncbi.nlm.nih.gov/projects/SNP/snp_ref.cgi?rs=76452710, downloaded on Mar. 21, 2004 (Exhibit 77).

NCBI SNP Database rs 2981582, https://www.ncbi.nlm.nih.gov/projects/SNP/snp_ref.cgi?rs=2981582 downloaded Jun. 29, 2003 (Exhibit 78).

NCBI SNP Database ss 23920837 (rs889312), http://www.ncbi.nlm.nih.gov/projects/SNP/snp_ref.cgi?rs=889312, downloaded Aug. 20, 2004(Exhibit 79).

May 19, 2016 Memorandum from USPTO Deputy Commissioner for Patent Examination Policy to the Patent Examining Corps (Exhibit 80).

International Preliminary Report on Patentability, dated Dec. 6, 2011, in connection with PCT International Application No. PCT/AU2010/000675, of which the subject application is a national stage entry.

International Search Report, dated Aug. 13, 2010 in connection with PCT International Application No. PCT/AU2010/000675, of which the subject application is a national stage entry.

"Perlegen Builds Commercial Group to Support Upcoming MammaPLUS(™) Launch", <URL http://www.evaluatepharma.com/Universal/View.aspx?type-Story&id =184247> published on Apr. 28, 2009.

"Perlegen Introduces BREVAGen Breast Cancer Risk Stratification test" <http://www.medicalnewstoday.com/releases/165123.php> retrieved by the International Search Authority on Jun. 23, 2010 in connection with PCT International Application No. PCT/AU2010/000675.

Easton et al., "Genome-wide association study identifies novel breast cancer susceptibility loci" Nature (2007) 447(7148):1087-1093.

Ahmed et al., "Newly discovered breast cancer susceptibility loci on 3p24 and 17q23.2" Nature Genetics (2009) 41(5):585-590.

Antoniou et al. "A comprehensive model for familial breast cancer incorporating BRCA1, BRCA2 and other genes" British Journal of Cancer (2002) 86, 76-83.

Antoniou et al., "The BOADICEA model of genetic susceptibility to breast and ovarian cancer" British Journal of Cancer (2004) 91, 1580-1590.

Antoniou et al., "Common variants in LSP1, 2q25 and 8q24 and breast cancer risk for BRCA1 and BRCA2 mutation carriers" Human Genetics (2009) 18(22):4442-4456.

Barringer et al., "Blunt-end and single-strand ligations by *Escheria coli* ligase: influence on and in vitro amplification scheme" Gene (1990) 89, 117-122.

Beaucage and Caruthers, "Deoxynucleoside Phosphoramidites—A New Class of Key Intermediates for Deoxypolynucleotide Synthesis" Tetrahedron Letters (1981) 22(20):1859-1862.

Blok and Kramer, "Amplifiable hybridization proves containing a molecular switch" Molecular and Cellular Probes (1997) 11, 187-194.

Bonnet et al., "Thermodynamic basis of the enhanced specificity of structured DNA probes" PNAS (1999) 96:6171-6176.

Chee et al., "Accessing genetic information with high-density DNA arrays" Science 274,n5287 (1996):610+. Expanded Academic ASAP. Web. Oct. 18, 2010. pp. 1-8.

Cheng et al., "Long PCR" Product Review, Nature (1994) 369:684-685.

Chlebowski et al., "Predicting Risk of Breast Cancer in Postmenopausal Women by Hormone Receptor Status" J Natl Cancer Inst (2007) 99:1695-1705.

Claus et al., "Autosomal Dominant Inheritance of Early-Onset Breast Cancer" Cancer (1994) 73(3):643-651.

Claus et al., "Effect of BRCA1 and BRCA2 on the Association Between Breast Cancer Risk and Family History" Journal of the National Cancer Institute (1998) 90(23):1824-1829.

Cook et al., "The Effect of Including C-Reactive Protein in Cardiovascular Risk Prediction Models for Women" Annals of Internal Medicine (2006) 145:21-29.

Costantino et al., "Validation Studies for Models Projecting the Risk of Invasive and Total Breast Cancer Incidence" J Natl Cancer Inst (1999) 91:1541-8.

Devlin and Risch, "A Comparison of Linkage Disequilibrium Measures for Fine-Scale Mapping" Genomics (1995) 29:311-322.

Evans et al., "A new scoring system for the chances of identifying a BRCA1/2 mutation outperforms existing models including BRCAPRO" J Med Genet (2004) 41:474-480.

Fang et al., "Designing a Novel Molecular Beacon for Surface-Immobilized DNA Hybridization Studies" J Am Chem Soc (1999) 121:2921-2922.

Fodor, "Massively parallel genomics" Science 277.5324 (1997): 393+ Expanded Academic ASAP. Web. Sep. 28, 2010, pp. 1-3.

Gail et al., "Projecting Individualized Probabilities of Developing Breast Cancer for White Females Who are Being Examined Annually" J Natl Cancer Inst (1989) 81:1879-1886.

Gail et al., "Weighing the Risks and Benefits of Tamoxifen Treatment for Preventing Breast Cancer" J Natl Cancer Inst (1999) 91:1829-46.

Gail et al., "Projecting Individualized Absolute Invasive Breast Cancer Risk in African American Women" J Natl Cancer Inst (2007) 99:1782-92.

Gail, "Discriminatory Accuracy From Single-Nucleotide Polymorphisms in Models to Predict Breast Cancer Risk" J Natl Cancer Inst (2008) 100:1037-1041.

Gail, "Value of Adding Single-Nucleotide Polymorphism Genotypes to a Breast Cancer Risk Model" J Natl Cancer Inst (2009) 101:959-963.

Gold et al., "Genome-wide association study provides evidence for a breast cancer risk locus at 6q22.33" PNAS (2008) 105(11):24340-4345.

Guatelli et al., "Isothermal, in vitro amplification of nucleic acids by a multienzyme reaction modeled after retroviral replication" PNAS (1990) 87:1874-1878.

Hsuih et al., "Novel, Ligation-Dependent PCT Assay for Detection of Hepatitis C Virus in Serum" Journal of Clinical Microbiology (1996) 34(3):501-507.

Jonker et al., "Modeling Familial Clustered Breast Cancer Using Published Data" Cancer Epidemiology, Biomarkers & Prevention (2003) 12:1479-1485.

Kelemen et al., "Genetic Variation in the Chromosome 17q23 Amplicon and Breast Cancer Risk" Cancer Epidemiol Biomarkers Prev (2009) 18(6):1864-8.

Kostrikis, "Spectral genotyping of human alleles" Science 279.5354 (1998): 1228+. Expanded Academic ASAP. Web. Oct. 18, 2010, pp. 1-4.

(56) References Cited

OTHER PUBLICATIONS

Kwoh et al., "Transcription-based amplification system and detection of amplified human immunodeficiency virus type 1 with a bead-based sandwich hybridization format" PNAS (1989) 86:1173-1177.
Landegren et al., "A ligase-mediated gene detection technique" Science 241.4869 (1998): 1077+. Expanded Academic ASAP. Web. Sep. 28, 2010 pp. 1-2.
Leone et al., "Molecular beacon probes combined with amplification by NASBA enable homogeneous, real-time detection of RNA" Nucleic Acids Research 26(9):2150-2155
Lockhart, "Mutant yeast on Drugs" Nature Medicine (1998) 4(11):1235-1236.
Marras et al., "Multiplex detection of single-nucleotide variations using molecular beacons" Genetic Analysis: Biomolecular Engineering (1999) 14:151-156.
Mealiffe et al., "Assessment of Clinical Validity of a Breast Cancer Risk Model Combining Genetic and Clinical Information" J Natl Cancer Inst (2010) 102:1618-1627.
Needham-VanDevanter et al., "Characterization of an adduct between CC-1065 and a defined oligodeoxynucleotide duplex" Nucleic Acids Research (1984) 12(15):6159-6168.
Pencina et al., "Evaluating the added predictive ability of a new marker: From area under the ROC curve to reclassification and beyond" Statistics in Medicine (2008) 27:157-172.
Pepe and Janes, "Gauging the Performance if SNPs, Biomarkers, and Clinical Factors for Predicting Risk of Breast Cancer" J Natl Cancer Inst (2008) 100(14):978-979.
Peto and Mack, "High constant incidence in twins and other relatives of women with breast cancer" Nature Genetics (2000) 26:411-414.
Pharoah et al., "Polygenes, Risk Prediction, and Targeted Prevention of Breast Cancer" N Eng J Med (2008) 358:2796-803.
Rockhill et al., "Validation of the Gail et al. Model of Breast Cancer Risk Prediction and Implications for Chemoprevention" J Natl Cancer Inst (2001) 93:358-66.
Sapolsky et al., "High-throughput polymorphism screening and genotyping with high-density oligonucleotide arrays" Genetic Analysis: Biomolecular Engineering (1999) 14:187-192.
Service et al., "Microchip Arrays Put DNA on the Spot" Science 282.53388 (1998): 396. Expanded Academic ASAP. Web. Sep. 23, 2010. pp. 1-3.
Service et al., "Coming Soon: The Pocket DNA Sequencer" Science 282.5388 (1998): 399. Expanded Academic ASAP. Web. Sep. 28, 2010 pp. 1-3.
Slatkin and Excoffier, "Testing for linkage disequilibrium in genotypic data using the Expectation-Maximization algorithm" Heredity (1996) 76, 377-383.
Sokol et al., "Real time detection of DNA-RNA hybridization in living cells" PNAS (1998) 95:11538-11543.
Sooknanan and Malek, "NASBA A detection and amplification system uniquely suited for RNA" Biotechnology (1995) 13:563-564.
Stacey et al., "Common variants on chromosomes 2q35 and 16q12 confer susceptibility to estrogen receptor-positive breast cancer" Nature Genetics (2007) 39(7):865-869.
Stacey et al., "Common variants on chromosome 5p12 confer susceptibility to estrogen receptor-positive breast cancer" Nature Genetics (2008) 40(6):703-706.
Thomas et al., "A multistage genome-wide association study in breast cancer identifies two new risk alleles at 1p11.2 and 14q24.1 (RAD51L1)" Nature Genetics (2009) 41(4):579-584.
Turnbull et al., "Genome-wide association study identifies five new breast cancer susceptibility loci" Nature Genetics (2010) 42(6):504-507 and Online Methods.
Tyagi and Kramer, "Molecular Beacons: Probes that Fluoresce upon Hybridization" Nature Biotechnology (1996) 14:303-308.
Tyagi et al., "Multicolor molecular beacons for allele discrimination" Nature Biotechnology (1998) 16:49-53.
Tyrer et al., "A breast cancer prediction model incorporating familial and personal risk factors" Statistics in Medicine (2004) 23:1111-1130.
Van Asperen et al., "Risk Estimation for Healthy Women from Breast Cancer Families: New Insights and New Strategies" Cancer Epidemiology, Biomarkers & Prevention (2004) 13, 87-93.
Van Brunt, "Amplifying Genes: PCT and its Alternatives" Bio/Technology (1990) 8, pp. 291, 292 and 294.
Vet et al., "Multiplex detection of four pathogenic retroviruses using molecular beacons" PNAS (1999) 96: 6394-6399.
Wu and Wallace, "The Ligation Amplification Reaction (LAR)—Amplification of Specific DNA Sequences Using Sequential Rounds of Template-Dependent Ligation" Genomics (1989) 4, 560-569.
Zhang et al., "Automated and Integrated System for High-Throughput DNA Genotyping Directly from Blood" Anal Chem (1999) 71, 1138-1145.
"Breast cancer breakthrough", <URL http://au.news.yahoo.com/today-tonight/health/article/-/13691294/breast-cancer-breakthrough> published on May 15, 2012.
Extended European Search Report, dated Oct. 18, 2012 in connection with European Patent Application No. 10782820.4.
European Search Opinion, dated Oct. 18, 2012 in connection with European Patent Application No. 10782820.4.
Patent Examination Report No. 1, dated Oct. 9, 2012 in connection with Australian Patent Application No. 2010256343.
Anonymous, "Perlegen Builds Commercial Group to Support Upcoming MammaPLUS(™) Launch" Evaluatepharma Press Release, Apr. 28, 2009.
Anonymous, "Perlegen Introduces BRAVAGen™ Breast Cancer Risk Stratification Test" Medical News Today, Sep. 24, 2009.
Bondy et al. (1994) "Validation of a Breast Cancer Risk Assessment Model in Women With a Positive Family History" Journal of the National Cancer Institute, vol. 86, No. 8, pp. 620-625.
Costantino et al. (1999) "Validation Studies for Models Projecting the Risk of Invasive and Total Breast Cancer Incidence" Journal of the National Cancer Institute, vol. 91, No. 18, pp. 1541-1548.
Jupe et al. (2007) "The OncoVue (R) model for predicting breast cancer risk" Breast Cancer Research and Treatment vol. 106 No. Suppl. 1, p. S179.
Matsuno et al. (2011) "Projecting Individualized Absolute Invasive Breast Cancer Risk in Asian and Pacific Islander American Women" J Natl Cancer Inst 2011;103:951-961.
Schonfeld et al. (2010) "Effect of Changing Breast Cancer Incidence Rates on the Calibration of the Gail Model" J Clin Oncol 28, pp. 1-8.
Spiegelman et al. (1994) "Validation of the Gail et al. Model for Predicting Individual Breast Cancer Risk" Journal of the National Cancer Institute 68(8):600-607.
Zheng et al. (2010) "Genetic and Clinical Predictors for Breast Cancer Risk Assessment and Stratification Among Chinese Women" Journal of the National Cancer Institute 102(13):972-981.
Liu et al. (2006) "The role of Self-Defined Race/Ethnicity in Population Structure Control" Annals of Human Genetics 70:496-505.
Merriam-Webster Dictionary definition for "Caucasian," available from www.merriam-webster.com/medical/Caucasian, accessed Nov. 2, 2012.
U.S. Appl. No. 16/513,999, filed Jul. 17, 2019, Cox et al.
U.S. Appl. No. 16/480,516, filed Jul. 24, 2019, Allman.
Oct. 21, 2019 Office Action issued in connection with U.S. Appl. No. 15/515,826.
Nov. 30, 2018 Office Action issued in connection with U.S. Appl. No. 15/814,255.
May 2, 2019 Final Office Action issued in connection with U.S. Appl. No. 15/814,255.
Dec. 31, 2018 Office Action in connection with U.S. Appl. No. 15/616,679.
Fung et al. (2019) "Performance of Single-Nucleotide Polymorphisms in Breast Cancer Risk Prediction Models: A Systematic Review and Meta-analysis" Cancer Epidemiol. Biomarkers. Prev. 28(3):506-521.

(56) References Cited

OTHER PUBLICATIONS

Allman et al. (2015) "Should Women with a Projected 5-Year Risk of Developing Breast Cancer of 1.4% or Higher Be Offered Pharmacologic Risk Reduction?" World Congress on Controversies in Breast Cancer 22-24.
Hopper (2015) "Odds per Adjusted Standard Deviation: Comparing Strengths of Associations for Risk Factors Measured on Different Scales and Across Diseases and Populations" Am. J. Epidemiol. 182(10):863-867.
Millikan et al. (2005) "Polymorphisms in DNA Repair Genes, Medical Exposure to Ionizing Radiation, and Breast Cancer Risk" Cancer Epidemiol. Biomarkers. Prev. 14(10):2326-2334.
Pharoah et al. (2004) "Association Studies for Finding Cancer-Susceptibility Genetic Variants" Nature Reviews 4:850-860.
Bonnen et al. (2002) "Haplotype and Linkage Disequilibrium Architecture for Human Cancer-Associated Genes" Genome Research 12:1846-1853.
Collaborative Group in Hormonal Factors in Breast Cancer (2001) "Familial breast cancer: collaborative reanalysis of individual data from 52 epidemiological studies including 58,209 women with breast cancer and 101,986 women without the disease" The Lancet 358:1389-1399.
Ponder et al. (2005) "Polygenic Inherited Predisposition to Breast Cancer" Cold Spring Harbor Symposia on Quantitative Biology vol. LXX:35-41.
Nov. 25, 2013 Office Action, issued in connection with U.S. Appl. No. 12/370,972.
Breast Cancer. American Cancer Society. 2013, pp. 1-134. Downloaded from Cancer.org on Oct. 17, 2013.
Rodi et al, (2003) "A Strategy for the Rapid Discovery of Disease Markers Using the MassARRAYTM System." BioTechniques, 32:S62-S69.
Db SNP ss No. 23605537 (www.ncbi.nlm.nih.gov/projects/SNP/snp_ss.cgi?subsnp_id-23605537) Aug. 20, 2004.
Db SNP ss No. 23575498 (www.ncbi.nlm.nih.gov/SNP/snp_ss.cgi?subsnp_id=23575498) Aug. 20, 2004.
Db SNP ss No. 24561224 (www.ncbi.nlm.nih.gov/projects/SNP/snp_ref.cgi?rs=rs3817198) Aug. 20, 2004.
Armstrong et al. (2000) "Assessing the Risk of Breast Cancer. The New England Journal of Medicine," 342(8):564-571.
Jul. 9, 2013 Response filed in connection with U.S. Appl. No. 12/890,272.
Jul. 10, 2013 Interview Summary issued in connection with U.S. Appl. No. 12/890,272.
Advani and Morena-Aspitia (2014) Breast Cancer: Targets & Therapy; 6: 59-71.
American Cancer Society: (2013) Breast Cancer Facts & Figures 2013-2014. Atlanta (GA), American Cancer Society Inc, 12.
Brentall et al. (2014) British Journal of Cancer 110: 827-828.
Chen et al. (2004) Stat Appl Genet Mol Biol. 3: Article 21.
Claus et al. (1991) Am J Hum Genet. 48: 232-242.
Claus et al. (1993) Breast Cancer Res Treat. 28: 115-120.
Cuzick et al. (2014) Journal of Clinical Oncology 43:Abstract No. 1519.
Darabi et al. (2012) Breast Cancer Research 14: R25.
De la Cruz (2014) Prim Care Clin Office Pract; 41: 283-306.
Dite et al. (2013) Breast Cancer Res Treat. 139: 887-896.
Ellis et al. (2006) Genetic Epidemiology 30: 48-61.
Fodor (1997a) FASEB Journal 11:A879.
Fodor (1997b) Science 277: 393-395.
Garcia (2004) Pediatrics 113:1394.
Ho et al. (2013) The Malaysian Journal of Pathology 1: 33-43.
Mackarem et al. (2001) The Breast Journal 2001 vol. 7 p. 34.
Mahoney et al. (2008) Cancer J Clin; 58: 347-371.
Mazzola et al. (2014) Cancer Epidemiol Biomarkers Prev. 23: 1689-1695.
McCarthy et al. (2013) Breast Cancer Research & Treatment 138: 889-898.
Parmigiani et al. (1998) Am J Hum Genet. 62: 145-158.
Parmigiani et al. (2007) Ann Intern Med. 1479: 441-450.
Raskin et al. (2008) Cancer Epidemiol Biomarkers Prey Vo. 17 p. 1060.
Ruiz-Narvaez (2010) Breast Cancer Res Treat vol. 123 p. 525.
Saslow et al. (2007) CA Cancer J Clin. 57: 75-89.
Schwartz (2001) N. Engl. J. Med. 344(18):1392-1393.
Sorlie et al. (2001) Proc. Natl. Acad. Sci., 98: 10869-10874.
Visvanathan et al. (2009) Journal of Clinical Oncology. 27: 3235-3258.
WIRES: Questions and Answers. "Average risk of breast cancer and general information".

* cited by examiner

Fig. 3

| # | SNP | Genomic region | Chromosome | Position | Nearest Gene | Caucasian | African American | Hispanic |
|---|---|---|---|---|---|---|---|---|
| 1 | rs616488 | 1p36.22 | 1 | 10,566,215 | PEX14 | | | |
| 2 | rs11552449 | 1p13.2 | 1 | 114,448,389 | SYT6 | | | |
| 3 | rs11249433 | 1p11.2 | 1 | 121,280,613 | FCGR1B | | | |
| 4 | rs6678914 | 1q32.1 | 1 | 202,187,176 | LGR6 | | | |
| 5 | rs4245739 | 1q32.1 | 1 | 204,518,842 | MDM4 | | | |
| 6 | rs12710696 | 2p24.1 | 2 | 19,320,803 | OSR1 | | | |
| 7 | rs4849887 | 2q14.2 | 2 | 120,487,546 | INHBB | | | |
| 8 | rs2016394 | 2q31.1 | 2 | 172,972,971 | DLX2 | | | |
| 9 | rs1550623 | 2q31.1 | 2 | 174,212,894 | CDCA7 | | | |
| 10 | rs1045485 | 2q33.1 | 2 | 202,149,589 | CASP8 | | | |
| 11 | rs13387042 | 2q35 | 2 | 217,905,832 | TNP1 | | | |
| 12 | rs16857609 | 2q35 | 2 | 218,296,508 | TNS1 | | | |
| 13 | rs6762644 | 3p26.1 | 3 | 4,742,276 | ITPR1 | | | |
| 14 | rs4973768 | 3p24.1 | 3 | 27,416,013 | SLC4A7 | | | |
| 15 | rs12493607 | 3p24.1 | 3 | 30,682,939 | TGFBR2 | | | |
| 16 | rs9790517 | 4q24 | 4 | 106,084,778 | TET2 | | | |
| 17 | rs6828523 | 4q34.1 | 4 | 175,846,426 | ADAM29 | | | |
| 18 | rs10069690 | 5p15.33 | 5 | 1,279,790 | TERT | | | |
| 19 | rs10941679 | 5p12 | 5 | 44,706,498 | MRPS30 | | | |
| 20 | rs10472076 | 5q11.2 | 5 | 58,184,061 | RAB3C | | | |
| 21 | rs1353747 | 5q11.2 | 5 | 58,337,481 | PDE4D | | | |
| 22 | rs1432679 | 5q33.3 | 5 | 158,244,083 | EBF1 | | | |
| 23 | rs11242675 | 6p25.3 | 6 | 1,318,878 | FOXQ1 | | | |
| 24 | rs204247 | 6p23 | 6 | 13,722,523 | RANBP9 | | | |
| 25 | rs17529111 | 6q14 | 6 | 81418669 | FAM46A | | | |
| 26 | rs2046210 | 6q25.1 | 6 | 151,948,366 | C6orf97 | | | |
| 27 | rs720475 | 7q35 | 7 | 144,074,929 | ARHGEF5 | | | |
| 28 | rs9693444 | 8p12 | 8 | 29,509,616 | DUSP4 | | | |
| 29 | rs6472903 | 8q21.11 | 8 | 76,230,301 | HNF4G | | | |
| 30 | rs2943559 | 8q21.11 | 8 | 76,417,937 | HNF4G | | | |
| 31 | rs13281615 | 8q24.21 | 8 | 128,355,618 | POU5F1B | | | |
| 32 | rs11780156 | 8q24.21 | 8 | 129,194,641 | MYC | | | |
| 33 | rs1011970 | 9p21.3 | 9 | 22,062,134 | CDKN2B | | | |
| 34 | rs10759243 | 9q31.2 | 9 | 110,306,115 | KLF4 | | | |
| 35 | rs865686 | 9q31.2 | 9 | 110,888,478 | KLF4 | | | |
| 36 | rs2380205 | 10p15.1 | 10 | 5,886,734 | ANKRD16 | | | |
| 37 | rs7072776 | 10p12.31 | 10 | 22,032,942 | MLLT10 | | | |
| 38 | rs11814448 | 10p12.31 | 10 | 22,315,843 | DNAJC1 | | | |

| # | SNP | Locus | Chr | Position | Gene | Col A | Col B | Col C |
|---|---|---|---|---|---|---|---|---|
| 39 | rs10995190 | 10q21.2 | 10 | 64,278,682 | ZNF365 | ✕ | ✕ | ✕ |
| 40 | rs704010 | 10q22.3 | 10 | 80,841,148 | ZMIZ1 | ✕ | ✕ | ✕ |
| 41 | rs7904519 | 10q25.2 | 10 | 114,773,927 | TCF7L2 | ✕ | ✕ | ✕ |
| 42 | rs2981579 | 10q26.13 | 10 | 123,337,335 | FGFR2 | ✕ | ✕ | ✕ |
| 43 | rs11199914 | 10q26.12 | 10 | 123,093,901 | FGFR2 | ✕ | ✕ | ✕ |
| 44 | rs3817198 | 11p15.5 | 11 | 1,909,006 | LSP1 | ✕ | ✕ | ✕ |
| 45 | rs3903072 | 11q13.1 | 11 | 65,583,066 | SNX32 | ✕ | ✕ | ✕ |
| 46 | rs554219 | 11q13.3 | 11 | 69,331,642 | CCND1 | ✕ | ✕ | ✕ |
| 47 | rs75915166 | 11q13.3 | 11 | 69,379,161 | FGF3 | ✕ | ✕ | ✕ |
| 48 | rs11820646 | 11q24.3 | 11 | 129,461,171 | BARX2 | ✕ | ✕ | ✕ |
| 49 | rs12422552 | 12p13.1 | 12 | 14,413,931 | ATF7IP | ✕ | ✕ | ✕ |
| 50 | rs10771399 | 12p11.22 | 12 | 28,155,080 | PTHLH | ✕ | ✕ | ✕ |
| 51 | rs17356907 | 12q22 | 12 | 96,027,759 | NTN4 | ✕ | ✕ | ✕ |
| 52 | rs1292011 | 12q24.21 | 12 | 115,836,522 | TBX3 | ✕ | ✕ | ✕ |
| 53 | rs11571833 | 13q13.1 | 13 | 32,972,626 | BRCA2 | ✕ | ✕ | ✕ |
| 54 | rs2236007 | 14q13.3 | 14 | 37,132,769 | PAX9 | ✕ | ✕ | ✕ |
| 55 | rs999737 | 14q23 | 14 | 68567965 | RAD51L1 | ✕ | ✕ | ✕ |
| 56 | rs2588809 | 14q24.1 | 14 | 68,660,428 | RAD51B | ✕ | ✕ | ✕ |
| 57 | rs941764 | 14q32.11 | 14 | 91,841,069 | CCDC88C | ✕ | ✕ | ✕ |
| 58 | rs3803662 | 16q12.1 | 16 | 52,586,341 | TOX3 | ✕ | ✕ | ✕ |
| 59 | rs17817449 | 16q12.2 | 16 | 53,813,367 | FTO | ✕ | ✕ | ✕ |
| 60 | rs11075995 | 16q12.2 | 16 | 53,855,291 | FTO | ✕ | ✕ | ✕ |
| 61 | rs13329835 | 16q23.2 | 16 | 80,650,805 | CDYL2 | ✕ | ✕ | ✕ |
| 62 | rs6504950 | 17q22 | 17 | 53,056,471 | STXBP4 | ✕ | ✕ | ✕ |
| 63 | rs527616 | 18q11.2 | 18 | 24,337,424 | AQP4 | ✕ | ✕ | ✕ |
| 64 | rs1436904 | 18q11.2 | 18 | 24,570,667 | CHST9 | ✕ | ✕ | ✕ |
| 65 | rs8170 | 19p13.11 | 19 | 17,389,704 | BABAM1 | ✕ | ✕ | ✕ |
| 66 | rs4808801 | 19p13.11 | 19 | 18,571,141 | ELL | ✕ | ✕ | ✕ |
| 67 | rs3760982 | 19q13.31 | 19 | 44,286,513 | KCNN4 | ✕ | ✕ | ✕ |
| 68 | rs2823093 | 21q21.1 | 21 | 16,520,832 | NRIP1 | ✕ | ✕ | ✕ |
| 69 | rs132390 | 22q12.2 | 22 | 29,621,477 | EMID1 | ✕ | ✕ | ✕ |
| 70 | rs6001930 | 22q13.1 | 22 | 40,876,234 | SGSM3 | ✕ | ✕ | ✕ |
| 71 | rs7696175 | 4p14 | 4 | 38819365 | TLR1 |  |  | ▦ |
| 72 | rs4415084 | 5p12 | 5 | 44662413 | FGF10 |  | ▨ | ▦ |
| 73 | rs7726159 | 5p15.33 | 5 | 1,282,204 | TERT | ■ |  | ▦ |
| 74 | rs2736108 | 5p15.33 | 5 | 1,297,373 | TERT | ■ |  | ▦ |
| 75 | rs889312 | 5q11.2 | 5 | 56,031,884 | MAP3K1 |  | ▨ |  |
| 76 | rs2067980 | 5q11.2 | 5 | 44982215 | MRPS30 |  |  | ▦ |
| 77 | rs2180341 | 6q22.3 | 6 | 127279485 | RNF146 |  |  | ▦ |
| 78 | rs9485370 | 6q25 | 6 | 149285665 | TAB2 |  | ▨ |  |

(Fig. 3 continued)

| 79 | RS12662670 | 6q25.1 | 6 | 151,597,721 | ESR1 | ■ | | ▦ |
| 80 | rs3757318 | 6q25.1 | 6 | 151,914,113 | C6orf97 | | ╱╱ | |
| 81 | rs17157903 | 7q22 | 7 | 103987589 | RELN | | | ▦ |
| 82 | rs10822013 | 10q21.2 | 10 | 62492218 | ZNF365 | | ╱╱ | |
| 83 | rs2981582 | 10q26 | 10 | 121592803 | FGFR2 | | ╱╱ | |
| 84 | rs614367 | 11q13.3 | 11 | 69513996 | CCND1 | | ╱╱ | |
| 85 | rs78540526 | 11q13.3 | 11 | 69,516,650 | CCND1 | ■ | | ▦ |
| 86 | rs2363956 | 19P13 | 19 | 17,283,315 | ANKLE1 | ■ | | |
| 87 | rs2284378 | 20q11.22 | 20 | 32,588,095 | DYNLRB1 | | ╱╱ | |
| 88 | rs17879961 | 22q12.1 | 22 | 28,725,099 | CHEK2157T | ■ | | ▦ |
| Total | | | | | | 77 | 78 | 82 |

Legend

| | |
|---|---|
| ✕ | Common to Caucasian, African American and Hispanic |
| ■ | Caucasian |
| ╱╱ | African American |
| ▦ | Hispanic |

(Fig. 3 continued)

Fig. 4

| # | SNP | Genomic region | Chromo-some | Position | Nearest Gene | Cauc-asian | African American | Hispanic |
|---|---|---|---|---|---|---|---|---|
| 1 | rs616488 | 1p36.22 | 1 | 10,566,215 | PEX14 | | | |
| 2 | rs11552449 | 1p13.2 | 1 | 114,448,389 | SYT6 | | | |
| 3 | rs11249433 | 1p11.2 | 1 | 121,280,613 | FCGR1B | | | |
| 4 | rs6678914 | 1q32.1 | 1 | 202,187,176 | LGR6 | | | |
| 5 | rs4245739 | 1q32.1 | 1 | 204,518,842 | MDM4 | | | |
| 6 | rs12710696 | 2p24.1 | 2 | 19,320,803 | OSR1 | | | |
| 7 | rs4849887 | 2q14.2 | 2 | 120,487,546 | INHBB | | | |
| 8 | rs2016394 | 2q31.1 | 2 | 172,972,971 | DLX2 | | | |
| 9 | rs1550623 | 2q31.1 | 2 | 174,212,894 | CDCA7 | | | |
| 10 | rs1045485 | 2q33.1 | 2 | 202,149,589 | CASP8 | | | |
| 11 | rs13387042 | 2q35 | 2 | 217,905,832 | TNP1 | | | |
| 12 | rs16857609 | 2q35 | 2 | 218,296,508 | TNS1 | | | |
| 13 | rs6762644 | 3p26.1 | 3 | 4,742,276 | ITPR1 | | | |
| 14 | rs4973768 | 3p24.1 | 3 | 27,416,013 | SLC4A7 | | | |
| 15 | rs12493607 | 3p24.1 | 3 | 30,682,939 | TGFBR2 | | | |
| 16 | rs9790517 | 4q24 | 4 | 106,084,778 | TET2 | | | |
| 17 | rs6828523 | 4q34.1 | 4 | 175,846,426 | ADAM29 | | | |
| 18 | rs10069690 | 5p15.33 | 5 | 1,279,790 | TERT | | | |
| 19 | rs10941679 | 5p12 | 5 | 44,706,498 | MRPS30 | | | |
| 20 | rs10472076 | 5q11.2 | 5 | 58,184,061 | RAB3C | | | |
| 21 | rs1353747 | 5q11.2 | 5 | 58,337,481 | PDE4D | | | |
| 22 | rs1432679 | 5q33.3 | 5 | 158,244,083 | EBF1 | | | |
| 23 | rs11242675 | 6p25.3 | 6 | 1,318,878 | FOXQ1 | | | |
| 24 | rs204247 | 6p23 | 6 | 13,722,523 | RANBP9 | | | |
| 25 | rs17529111 | 6q14 | 6 | 81418669 | FAM46A | | | |
| 26 | rs2046210 | 6q25.1 | 6 | 151,948,366 | C6orf97 | | | |
| 27 | rs720475 | 7q35 | 7 | 144,074,929 | ARHGEF5 | | | |
| 28 | rs9693444 | 8p12 | 8 | 29,509,616 | DUSP4 | | | |
| 29 | rs6472903 | 8q21.11 | 8 | 76,230,301 | HNF4G | | | |
| 30 | rs2943559 | 8q21.11 | 8 | 76,417,937 | HNF4G | | | |
| 31 | rs13281615 | 8q24.21 | 8 | 128,355,618 | POU5F1B | | | |
| 32 | rs11780156 | 8q24.21 | 8 | 129,194,641 | MYC | | | |
| 33 | rs1011970 | 9p21.3 | 9 | 22,062,134 | CDKN2B | | | |
| 34 | rs10759243 | 9q31.2 | 9 | 110,306,115 | KLF4 | | | |
| 35 | rs865686 | 9q31.2 | 9 | 110,888,478 | KLF4 | | | |
| 36 | rs2380205 | 10p15.1 | 10 | 5,886,734 | ANKRD16 | | | |
| 37 | rs7072776 | 10p12.31 | 10 | 22,032,942 | MLLT10 | | | |
| 38 | rs11814448 | 10p12.31 | 10 | 22,315,843 | DNAJC1 | | | |

| | | | | | | |
|---|---|---|---|---|---|---|
| 39 | rs10995190 | 10q21.2 | 10 | 64,278,682 | ZNF365 | |
| 40 | rs704010 | 10q22.3 | 10 | 80,841,148 | ZMIZ1 | |
| 41 | rs7904519 | 10q25.2 | 10 | 114,773,927 | TCF7L2 | |
| 42 | rs2981579 | 10q26.13 | 10 | 123,337,335 | FGFR2 | |
| 43 | rs11199914 | 10q26.12 | 10 | 123,093,901 | FGFR2 | |
| 44 | rs3817198 | 11p15.5 | 11 | 1,909,006 | LSP1 | |
| 45 | rs3903072 | 11q13.1 | 11 | 65,583,066 | SNX32 | |
| 46 | rs554219 | 11q13.3 | 11 | 69,331,642 | CCND1 | |
| 47 | rs75915166 | 11q13.3 | 11 | 69,379,161 | FGF3 | |
| 48 | rs11820646 | 11q24.3 | 11 | 129,461,171 | BARX2 | |
| 49 | rs12422552 | 12p13.1 | 12 | 14,413,931 | ATF7IP | |
| 50 | rs10771399 | 12p11.22 | 12 | 28,155,080 | PTHLH | |
| 51 | rs17356907 | 12q22 | 12 | 96,027,759 | NTN4 | |
| 52 | rs1292011 | 12q24.21 | 12 | 115,836,522 | TBX3 | |
| 53 | rs11571833 | 13q13.1 | 13 | 32,972,626 | BRCA2 | |
| 54 | rs2236007 | 14q13.3 | 14 | 37,132,769 | PAX9 | |
| 55 | rs999737 | 14q23 | 14 | 68567965 | RAD51L1 | |
| 56 | rs2588809 | 14q24.1 | 14 | 68,660,428 | RAD51B | |
| 57 | rs941764 | 14q32.11 | 14 | 91,841,069 | CCDC88C | |
| 58 | rs3803662 | 16q12.1 | 16 | 52,586,341 | TOX3 | |
| 59 | rs17817449 | 16q12.2 | 16 | 53,813,367 | FTO | |
| 60 | rs11075995 | 16q12.2 | 16 | 53,855,291 | FTO | |
| 61 | rs13329835 | 16q23.2 | 16 | 80,650,805 | CDYL2 | |
| 62 | rs6504950 | 17q22 | 17 | 53,056,471 | STXBP4 | |
| 63 | rs527616 | 18q11.2 | 18 | 24,337,424 | AQP4 | |
| 64 | rs1436904 | 18q11.2 | 18 | 24,570,667 | CHST9 | |
| 65 | rs8170 | 19p13.11 | 19 | 17,389,704 | BABAM1 | |
| 66 | rs4808801 | 19p13.11 | 19 | 18,571,141 | ELL | |
| 67 | rs3760982 | 19q13.31 | 19 | 44,286,513 | KCNN4 | |
| 68 | rs2823093 | 21q21.1 | 21 | 16,520,832 | NRIP1 | |
| 69 | rs132390 | 22q12.2 | 22 | 29,621,477 | EMID1 | |
| 70 | rs6001930 | 22q13.1 | 22 | 40,876,234 | SGSM3 | |

Legend

| | |
|---|---|
| ⊠ | Common to Caucasian, African American and Hispanic |
| ■ | Caucasian |
| ╲ | African American |
| ╬ | Hispanic |

(Fig. 4 continued)

Fig. 5

| SNP | Genomic region | Chromo-some | Position | Nearest Gene | Caucasian | African American | Hispanic |
|---|---|---|---|---|---|---|---|
| rs7696175 | 4p14 | 4 | 38819365 | TLR1 | | | ■ |
| rs4415084 | 5p12 | 5 | 44662413 | FGF10 | | ■ | |
| rs7726159 | 5p15.33 | 5 | 1,282,204 | TERT | ■ | | ■ |
| rs2736108 | 5p15.33 | 5 | 1,297,373 | TERT | ■ | | ■ |
| rs889312 | 5q11.2 | 5 | 56,031,884 | MAP3K1 | | ■ | |
| rs2067980 | 5q11.2 | 5 | 44982215 | MRPS30 | | | ■ |
| rs2180341 | 6q22.3 | 6 | 127279485 | RNF146 | | | ■ |
| rs9485370 | 6q25 | 6 | 149285665 | TAB2 | | ■ | |
| RS12662670 | 6q25.1 | 6 | 151,597,721 | ESR1 | ■ | | ■ |
| rs3757318 | 6q25.1 | 6 | 151,914,113 | C6orf97 | | ■ | |
| rs17157903 | 7q22 | 7 | 103987589 | RELN | | | ■ |
| rs10822013 | 10q21.2 | 10 | 62492218 | ZNF365 | | ■ | |
| rs2981582 | 10q26 | 10 | 121592803 | FGFR2 | | ■ | |
| rs614367 | 11q13.3 | 11 | 69513996 | CCND1 | | ■ | |
| rs78540526 | 11q13.3 | 11 | 69,516,650 | CCND1 | ■ | | ■ |
| rs2363956 | 19P13 | 19 | 17,283,315 | ANKLE1 | | | ■ |
| rs2284378 | 20q11.22 | 20 | 32,588,095 | DYNLRB1 | | ■ | |
| rs17879961 | 22q12.1 | 22 | 28,725,099 | CHEK2157T | ■ | | ■ |

Legend:
- Common to Caucasian, African American and Hispanic
- Caucasian
- African American
- Hispanic

Fig. 6

| SNP | | | | Caucasian genotype | Caucasian | African American genotype | African American | Hispanic genotype | Hispanic |
|---|---|---|---|---|---|---|---|---|---|
| rs616488 | AA | GA | GG | C | 1.039618 | A | 1.008205 | H | 1.035308 |
| rs11552449 | CC | TC | TT | C | 1.051833 | | | H | 0.962701 |
| rs11249433 | AA | GA | GG | C | 1.117892 | A | 0.982653 | H | 1.194769 |
| rs6678914 | AA | AG | GG | C | 0.987091 | A | 1 | H | 0.915171 |
| rs4245739 | AA | CA | CC | C | 1.01382 | A | 0.98412 | H | 1.039425 |
| rs12710696 | CC | CT | TT | C | 1.049692 | A | 1.055409 | H | 1.166034 |
| rs4849887 | TT | TC | CC | C | 0.857621 | A | 0.808706 | H | 0.829796 |
| rs2016394 | TT | TC | CC | C | 0.997323 | A | 0.978295 | H | 0.975891 |
| rs1550623 | AA | GA | GG | C | 0.908137 | A | 0.871808 | H | 0.878429 |
| rs1045485 | CC | CG | GG | C | 0.938736 | A | 0.998587 | | |
| rs13387042 | AA | GA | GG | C | 0.993331 | A | 0.948939 | H | 1.01897 |
| rs16857609 | CC | TC | TT | C | 1.107487 | A | 1.26368 | H | 0.925313 |
| rs6762644 | AA | GA | GG | C | 0.949146 | A | 0.95554 | H | 1 |
| rs4973768 | CC | TC | TT | C | 1.00338 | A | 1.010683 | H | 0.99415 |
| rs12493607 | CC | CG | GG | C | 0.963974 | A | 1.069587 | H | 0.98049 |
| rs7696175 | CC | CT | TT | | | | | H | 0.889419 |
| rs9790517 | CC | TC | TT | C | 1.025289 | A | 0.898013 | H | 0.975968 |
| rs6828523 | AA | AC | CC | C | 1.025003 | A | 1 | H | 1.047208 |
| rs10069690 | CC | TC | TT | C | 0.987534 | A | 0.866783 | H | 0.959287 |
| rs7726159 | CC | AC | AA | C | 1.011211 | | | | |
| rs2736108 | CC | TC | TT | C | 0.912448 | | | | |
| rs4415084 | CC | CT | TT | | | A | 0.88832 | | |
| rs10941679 | AA | GA | GG | C | 1.055621 | A | 1.022746 | H | 1.033912 |
| rs2067980 | AA | AG | GG | | | | | H | 0.958607 |
| rs889312 | AA | CA | CC | C | 0.93726 | A | 0.955353 | H | 0.908413 |
| rs10472076 | CC | CT | TT | C | 1.009498 | A | 0.977169 | H | 0.996367 |
| rs1353747 | GG | GT | TT | C | 1.015122 | A | 1.000396 | H | 0.992839 |
| rs1432679 | CC | CT | TT | C | 1.075619 | A | 1.028053 | H | 1.063017 |
| rs11242675 | CC | CT | TT | C | 0.98634 | A | 0.997989 | H | 0.989997 |
| rs204247 | AA | GA | GG | C | 1.056916 | A | 1.171088 | H | 0.988385 |
| rs17529111 | CC | GA | TT | C | 1.072022 | A | 0.981572 | | |

| | | | | | | | | | |
|---|---|---|---|---|---|---|---|---|---|
| rs2180341 | AA | AG | GG | | | | | H | 0.98952 |
| rs9485370 | GG | GT | TT | | | | | | |
| rs12662670 | GG | GT | TT | C | 1.271798 | | | | |
| rs140068132 | AA | AG | GG | | | | | H | 0.64565 |
| rs3757318 | GG | GA | AA | | | A | 1.221864 | | |
| rs2046210 | AA | AG | GG | C | 1.062128 | A | 0.991968 | H | 1.086778 |
| rs17157903 | CC | CT | TT | | | | | H | 0.898805 |
| rs720475 | AA | AG | GG | C | 1.027974 | A | 0.99758 | H | 0.981073 |
| rs9693444 | AA | AC | CC | C | 1.099367 | A | 1.075326 | H | 1.013401 |
| rs6472903 | GG | GT | TT | C | 0.941869 | A | 0.984248 | H | 0.983538 |
| rs2943559 | AA | GA | GG | C | 1.260936 | A | 1.03779 | H | 1.291322 |
| rs13281615 | AA | GA | GG | C | 0.926426 | A | 1.067791 | H | 0.910495 |
| rs11780156 | CC | TC | TT | C | 1.045846 | A | 0.717489 | H | 0.987094 |
| rs1011970 | GG | TG | TT | C | 1.084334 | A | 1.020439 | H | 1 |
| rs10759243 | CC | AC | AA | C | 0.959028 | A | 0.976811 | H | 0.904272 |
| rs865686 | GG | GT | TT | C | 0.972037 | A | 0.996429 | H | 0.957381 |
| rs2380205 | CC | TC | TT | C | 0.974259 | A | 1.017014 | H | 1.027348 |
| rs7072776 | AA | AG | GG | C | 1.082781 | A | 1.040416 | H | 1.026394 |
| rs11814448 | AA | CA | CC | C | 1.207448 | A | 0.991047 | H | 1.138045 |
| rs10822013 | CC | TC | TT | | | | | | |
| rs10995190 | AA | AG | GG | C | 0.768167 | A | 1.034045 | H | 0.85433 |
| rs704010 | CC | TC | TT | C | 1.01525 | A | 0.984326 | H | 1.016022 |
| rs7904519 | AA | AG | GG | C | 1.062365 | A | 1.052608 | | |
| rs2981582 | AA | AG | GG | | | A | 1.0504 | H | 1.245195 |
| rs11199914 | CC | TC | TT | C | 0.977163 | A | 0.998551 | H | 1.00117 |
| rs2981579 | AA | AG | GG | C | 0.825006 | A | 0.817208 | H | 0.911712 |
| rs3817198 | CC | CT | TT | C | 1.102875 | A | 0.966964 | H | 1.031305 |
| rs3903072 | GG | TG | TT | C | 0.995744 | A | 1.006438 | H | 1 |
| rs554219 | CC | CG | GG | C | 1.228619 | A | 1 | | |
| rs75915166 | AA | AC | CC | C | 1.045421 | A | 2.046497 | | |
| rs614367 | CC | CT | TT | | | A | 0.970062 | | |
| rs78540526 | CC | TC | TT | C | 1.367753 | | | | |
| rs11820646 | CC | TC | TT | C | 1.036821 | A | 0.991081 | H | 1.056268 |
| rs12422552 | CC | CG | GG | C | 1.015361 | A | 1.003476 | H | 1.082454 |
| rs10771399 | AA | GA | GG | C | 0.769715 | A | 0.715272 | H | 0.8386 |
| rs17356907 | AA | GA | GG | C | 1.057703 | A | 1.008286 | H | 1.007441 |
| rs1292011 | AA | GA | GG | C | 0.985492 | A | 0.996833 | H | 0.990975 |
| rs11571833 | AA | TA | TT | C | 1.583253 | A | 1.0003 | | |
| rs2236007 | AA | AG | GG | C | 0.876031 | A | 1.215585 | H | 0.896463 |

(Fig. 6 continued)

| | | | | | | | | | |
|---|---|---|---|---|---|---|---|---|---|
| rs999737 | CC | TC | TT | C | 0.957111 | A | 0.973708 | H | 0.943739 |
| rs2588809 | CC | TC | TT | C | 1.113946 | A | 1.014209 | H | 1.119679 |
| rs941764 | AA | GA | GG | C | 0.958115 | A | 0.873439 | H | 0.888152 |
| rs3803662 | AA | AG | GG | C | 1.093586 | A | 1.000176 | H | 1.042648 |
| rs17817449 | GG | GT | TT | C | 1.058443 | A | 1.039212 | H | 1.016399 |
| rs11075995 | AA | AT | TT | C | 0.982496 | A | 1.116585 | H | 1.210334 |
| rs13329835 | AA | GA | GG | C | 1.040798 | A | 0.978846 | H | 1.070623 |
| rs6504950 | AA | AG | GG | C | 1.03801 | A | 1.040832 | H | 1.007493 |
| rs527616 | CC | CG | GG | C | 0.946903 | A | 0.99431 | H | 0.968908 |
| rs1436904 | TT | GT | GG | C | 0.988372 | A | 1.010075 | H | 0.993221 |
| rs2363956 | GG | TG | TT | C | 1.026921 | | | H | 1.008453 |
| rs8170 | AA | AG | GG | C | 1.051206 | A | 1.216084 | H | 1.053933 |
| rs4808801 | AA | GA | GG | C | 0.979005 | A | 1.003367 | H | 0.966099 |
| rs3760982 | AA | AG | GG | C | 0.951001 | A | 1 | H | 0.98693 |
| rs2284378 | CC | CT | TT | | | A | 0.981073 | | |
| rs2823093 | AA | AG | GG | C | 0.964855 | A | 0.995657 | H | 1.054888 |
| rs17879961 | GG | GA | AA | C | 0.996378 | | | | |
| rs132390 | CC | CT | TT | C | 1.220497 | A | 0.784156 | | |
| rs6001930 | CC | CT | TT | C | 1.101661 | A | 1.014717 | H | 1.1273 |
| | | | | Product | 5.749988 | | 1.085822 | | 0.674828 |

(Fig. 6 continued)

METHODS FOR ASSESSING RISK OF DEVELOPING BREAST CANCER

CROSS-REFERENCE TO RELATED APPLICATIONS

This application is a continuation of PCT International Application No. PCT/AU2015/050583, filed Sep. 29, 2015, which claims the priority of Australian Application No. 2014903898, filed Sep. 30, 2014, the contents of each of which are hereby incorporated by reference in their entirety into this application.

REFERENCE TO SEQUENCE LISTING

This application incorporates-by-reference nucleotide and/or amino acid sequences which are present in the file named "160419_88199_Sequence_Listing_DH.txt", which is 3.08 kilobytes in size, and which was created Apr. 18, 2016 in the IBM-PC machine format, having an operating system compatibility with MS-Windows, which is contained in the text file filed Apr. 19, 2016 as part of this application.

TECHNICAL FIELD

The present disclosure relates to methods and systems for assessing the risk of a human female subject for de eloping a breast cancer. In particular, the present disclosure relates to combining clinical risk assessment and genetic risk assessment to improve risk analysis.

BACKGROUND OF THE INVENTION

It is estimated that in the USA approximately one in eight women will develop breast cancer in their lifetime. In 2013 it was predicted that over 230.000 women would be diagnosed with invasive breast cancer and almost 40.000 would die from the disease (ACS Breast Cancer Facts & FIGS. 2013-14). There is therefore a compelling reason to predict which women will develop disease, and to apply measures to prevent it.

A wide body of research has focused on phenotypic risk factors including age, family history, reproductive history, and benign breast disease. Various combinations of these risk factors have been compiled into the two most commonly used risk prediction algorithms; the Gail Model (appropriate for the general population) (also known as the Breast Cancer Risk Assessment Tool: BCRAT) and the Tyrer-Cuzick Model (appropriate for women with a stronger family history).

Breast cancer, like other common cancers, shows familial clustering. Numerous epidemiological studies have demonstrated that, the disease is approximately twice as common in first degree relatives of breast cancer patients. Family studies, and particularly twin studies, suggest that most if not all of this clustering has a genetic basis.

Several breast cancer susceptibility genes have already been identified, most importantly BRCA1 and BRCA2. Mutations in these genes confer a high risk of breast cancer (of the order of 65% and 45%, respectively, by age 70). Mutation screening of population-based series of breast cancer cases has shown that only about 15% of the familial risk of breast cancer can be explained by mutations in these genes. The other known breast cancer susceptibility genes (TP53, PTEN, ATM, CHEK2) make only small contributions to the familial risk (because the predisposing mutations are rare and/or confer only small risks). In total therefore, the known breast cancer susceptibility genes have been estimated to account for no more than 20% of the familial risk.

Genetic variation in risk may result from rare highly-penetrant mutations (such as those in BRCA1 and BRCA2) or from variants conferring more moderate risks. Several lines of evidence suggest strongly that high penetrance mutations are not major contributors to the residual familial risk of breast cancer. Firstly, mutation screening of multiple case families has found that the large majority of cases with a very strong family history (for example four or more affected relatives) harbor mutations in BRCA1 or BRCA2. Secondly, despite extensive efforts over the past nine years, genetic linkage studies have not identified any further linked loci. Thirdly, segregation analyses of large series of breast cancer families have found, after adjusting for BRCA1 and BRCA2, no evidence for a further major dominant breast cancer susceptibility allele.

Germline genetic testing for mutations in BRCA1 and BRCA2 is now routine in genetic medicine and allows for the identification of individuals at significantly increased risk for breast and other cancers. However, such mutations are relatively rare in the general population and account for approximately 10% of all breast cancer cases in the US (approximately half of which are due to BRCA1/2 mutations). The remaining 80% of sporadic breast cancers and those familial cancers for which no causative mutation is known have to be defined by other genetic/clinical markers common to the population at large.

The first commercially available test for assessing the risk of developing breast cancer which relies on the detection of low penetrance polymorphisms was the BREVAGen test described in WO 2010/139006. This test relies on the detection of 7 or 10 single nucleotide polymorphisms. However, there is the need for improved breast cancer risk assessment tests, particularly for non-Caucasian females.

SUMMARY OF THE INVENTION

The present inventors have identified SNP's within the genome that are useful for assessing the risk of a human female subject developing a breast cancer phenotype. Surprisingly, a selection of these SNP's remain informative across a plurality of ethnic backgrounds. These findings suggest that the SNP's of the present disclosure may be used in a method assessing the risk of a human female subject developing a breast cancer phenotype. In particular, these results suggest that such methods may be suitably robust to account for ethnic genotype variation.

Accordingly, in one aspect the present disclosure relates to a method for assessing the risk of a human female subject for developing a breast cancer comprising:

performing a clinical risk assessment of the female subject:

performing a genetic risk assessment of the female subject, wherein the genetic risk assessment involves detecting, in a biological sample derived from the female subject, at least 72 single nucleotide polymorphisms associated with a breast cancer, wherein at least 67 of the single nucleotide polymorphisms are selected from Table 7, or a single nucleotide polymorphism in linkage disequilibrium with one or more thereof, and the remaining single nucleotide polymorphisms are selected from Table 6, or a single nucleotide polymorphism in linkage disequilibrium with one or more thereof; and combining the clinical risk assessment with the genetic risk assessment to obtain the risk of a human female subject for developing breast cancer.

One of skill in the art will appreciate that the combined clinical risk assessment and genetic risk assessment defines the subjects overall risk for developing a breast cancer. Thus, the methods of the invention assess overall risk.

In an embodiment, the methods of the present disclosure determine the absolute risk of a human female subject for developing breast cancer.

In another embodiment, the methods of the present disclosure determine the relative risk of a human female subject for developing breast cancer.

The female can be of any race such as Caucasian, Negroid, Australoid. or Mongoloid. In an embodiment, the female is post-menopausal.

In an embodiment, the female is Caucasian. In a further embodiment, the method comprises detecting at least 72 single nucleotide polymorphisms shown in Table 9, or a single nucleotide polymorphism in linkage disequilibrium with one or more thereof.

In an additional embodiment, the method comprises detecting at least the 77 single nucleotide polymorphisms shown in Table 9, or a single nucleotide polymorphism in linkage disequilibrium with one or more thereof.

In another embodiment, the female is Negroid. In a further embodiment, the female is African-American. In a further embodiment, the method comprises detecting at least 74 single nucleotide polymorphisms shown in Table 10, or a single nucleotide polymorphism in linkage disequilibrium with one or more thereof.

In an additional embodiment, the method comprises detecting at least the 78 single nucleotide polymorphisms shown in Table 10, or a single nucleotide polymorphism in linkage disequilibrium with one or more thereof.

In another embodiment, the female is Hispanic. In a further embodiment, the method of the present disclosure comprises detecting at least 78 single nucleotide polymorphisms shown in Table 11, or a single nucleotide polymorphism in linkage disequilibrium with one or more thereof.

In an additional embodiment, the method comprises detecting at least the 82 single nucleotide polymorphisms shown in Table 11, or a single nucleotide polymorphism in linkage disequilibrium with one or more thereof.

In an embodiment, combining the clinical risk assessment with the genetic risk assessment comprises multiplying the risk assessments to provide the risk score.

In an embodiment, performing the clinical risk assessment uses a model selected from a group consisting of the Gail Model, the Claus Model, Claus Tables, BOADICEA, the Jonker Model, the Claus Extended Formula, the Tyrer-Cuzick Model, BRCAPRO, and the Manchester Scoring System.

In a further embodiment, performing the clinical risk assessment includes obtaining information from the female on one or more of the following: medical history of breast cancer, ductal carcinoma or lobular carcinoma, age, age of first menstrual period, age at which she first gave birth, family history of breast cancer, results of previous breast biopsies, breast density, and race/ethnicity.

In one embodiment, the clinical risk assessment is obtained using the Gail Model. In an embodiment when the Gail Model is used, the subject is 35 years of age or older.

In an embodiment, the Gail Model provides a Gail Lifetime risk score.

In an embodiment, the Gail Model provides a Gail 5-year risk score.

In an alternate embodiment, the clinical risk assessment is obtained using the Tyrer-Cuzick Model.

In an embodiment, when the Tyrer-Cuzick Model is used, the subject is 20 years of age or older.

In an embodiment, the methods of the present disclosure comprise detecting at least 73, 74, 75, 76, 77, 78, 79, 80, 81, 82 single nucleotide polymorphisms associated with a breast cancer, wherein at least 67 of the single nucleotide polymorphisms are selected from Table 7, or a single nucleotide polymorphism in linkage disequilibrium with one or more thereof and the remaining single nucleotide polymorphisms are selected from Table 6, or a single nucleotide polymorphism in linkage disequilibrium with one or more thereof.

In an embodiment, the female has had a biopsy of the breast.

In an embodiment, the female has not had breast cancer, lobular carcinoma or ductal carcinoma.

In an embodiment, the results of the clinical risk assessment indicate that the female should be subjected to more frequent screening and/or prophylactic anti-breast cancer therapy.

In a further embodiment, if it is determined the subject has a risk of developing breast cancer, the subject is more likely to be responsive to oestrogen inhibition therapy than non-responsive.

In an embodiment, the breast cancer is estrogen receptive positive or estrogen receptor negative.

In an embodiment, a single nucleotide polymorphism in linkage disequilibrium has linkage disequilibrium above 0.9.

In another embodiment, a single nucleotide polymorphism in linkage disequilibrium has linkage disequilibrium of 1.

In an embodiment, the net reclassification improvement of the methods of the present disclosure is greater than 0.01.

In a further embodiment, the net reclassification improvement of the methods of the present disclosure is greater than 0.05.

In yet another embodiment, the net reclassification improvement of the methods of the present disclosure is greater than 0.1.

In another embodiment, the 5-year risk determined by the clinical risk assessment is between about 1.5% to about 2%.

In another aspect, the present disclosure relates to a kit comprising at least 72 sets of primers for amplifying 72 or more nucleic acids, wherein the 72 or more nucleic acids comprise a single nucleotide polymorphism, wherein at least 67 of the sets of primers amplify nucleic acids comprising a single nucleotide polymorphism selected from Table 7, or a single nucleotide polymorphism in linkage disequilibrium with one or more thereof, and the remaining sets of primers amplify nucleic acids comprising a single nucleotide polymorphism selected from Table 6, or a single nucleotide polymorphism in linkage disequilibrium with one or more thereof.

In another aspect, the present disclosure relates to a genetic array comprising at least 72 sets of probes for hybridising to 72 or more nucleic acids, wherein the 72 or more nucleic acids comprise a single nucleotide polymorphism, wherein at least 67 of the probes hybridise to nucleic acids comprising a single nucleotide polymorphism selected from Table 7, or a single nucleotide polymorphism in linkage disequilibrium with one or more thereof, and the remaining probes hybridise to nucleic acids comprising a single nucleotide polymorphism selected from Table 6, or a single nucleotide polymorphism in linkage disequilibrium with one or more thereof.

In another aspect, the present disclosure relates to a method for determining the need for routine diagnostic testing of a human female subject for breast cancer comprising assessing the risk of the subject for developing breast cancer using the disclosed methods.

Screening is recommended for women with an approximately 20-25% lifetime risk of breast cancer (Saslow et al., 2007). Thus, in an embodiment, a risk score greater than about 20% lifetime risk indicates that the subject should be enrolled in a screening breast MRI and mammography program.

In another aspect, the present disclosure relates to a method of screening for breast cancer in a human female subject, the method comprising assessing the risk of the subject for developing breast cancer using the disclosed methods, and routinely screening for breast cancer in the subject if they are assessed as having a risk for developing breast cancer. For example, screening for breast cancer can involve enrolling the subject in a screening breast MRI and mammography program.

In another aspect, the present disclosure relates to a method for determining the need of a human female subject for prophylactic anti-breast cancer therapy comprising assessing the risk of the subject for developing breast cancer using the disclosed methods.

Pharmacological intervention is recommended in women with a risk score greater than about 1.66% 5-year risk (Visvanathan et al., 2009). Thus, in an embodiment, an risk score greater than about 1.66% 5-year risk indicates that a chemopreventative should be offered to the subject. For example, estrogen receptor therapy could be offered to the subject. Various exemplary estrogen receptor therapies are discussed further below.

In another aspect, the present disclosure relates to a method for preventing breast cancer in a human female subject the method comprising assessing the risk of the subject for developing a breast cancer using the disclosed methods, and administering an anti-breast cancer therapy to the subject if they are assessed as having a risk for developing breast cancer.

In one embodiment, the therapy inhibits oestrogen.

In a further aspect, the present disclosure relates to an anti-breast cancer therapy for use in preventing breast cancer in a human female subject at risk thereof, wherein the subject is assessed as having a risk for developing breast cancer according to the method of the present disclosure.

In another aspect, the present disclosure relates to a method for stratifying a group of human female subjects for a clinical trial of a candidate therapy, the method comprising assessing the individual risk of the subjects for developing breast cancer using the disclosed methods, and using the results of the assessment to select subjects more likely to be responsive to the therapy.

In another aspect, the present invention provides for the use of probes or at least 72 sets of primers for preparing a kit or system for assessing the risk of a human female subject for developing a breast cancer phenotype comprising:

performing a clinical risk assessment of the female subject;

performing a genetic risk assessment of the female subject, wherein the genetic risk assessment involves detecting, in a biological sample derived from the female subject, at least 72 single nucleotide polymorphisms associated with a breast cancer, wherein at least 67 of the single nucleotide polymorphisms are selected from Table 7, or a single nucleotide polymorphism in linkage disequilibrium with one or more thereof, and the remaining single nucleotide polymorphisms are selected from Table 6, or a single nucleotide polymorphism in linkage disequilibrium with one or more thereof; and combining the clinical risk assessment with the genetic risk assessment to obtain the risk of a human female subject for developing breast cancer.

In another aspect, the present disclosure relates to a computer implemented method for assessing the risk of a human female subject for developing breast cancer, the method operable in a computing system comprising a processor and a memory, the method comprising:

receiving clinical risk data and genetic risk data for the female subject, wherein the genetic risk data was obtained by detecting, in a biological sample derived from the female subject, at least 72 single nucleotide polymorphisms associated with breast cancer, wherein at least 67 of the single nucleotide polymorphisms are selected from Table 7, or a single nucleotide polymorphism in linkage disequilibrium with one or more thereof, and the remaining single nucleotide polymorphisms are selected from Table 6, or a single nucleotide polymorphism in linkage disequilibrium with one or more thereof;

processing the data to combine the clinical risk data with the genetic risk data to obtain the risk of a human female subject for developing breast cancer:

outputting the risk of a human female subject for developing breast cancer.

In one embodiment, the clinical risk data and genetic risk data for the female subject is received from a user interface coupled to the computing system.

In another embodiment, the clinical risk data and genetic risk data for the female subject is received from a remote device across a wireless communications network.

In another embodiment, outputting comprises outputting information to a user interface coupled to the computing system.

In another embodiment, outputting comprises transmitting information to a remote device across a wireless communications network.

In another embodiment, the present disclosure relates to a system configured to perform the disclosed methods.

In another embodiment, the present disclosure relates to a system for assessing the risk of a human female subject for developing breast cancer comprising:

system instructions for performing a clinical risk assessment of the female subject:

system instructions for performing a genetic risk assessment of the female subject according to the present disclosure; and system instructions for combining the clinical risk assessment with the genetic risk assessment to obtain the risk of a human female subject for developing breast cancer.

As will be apparent, at least some features of the methods, kits and systems can be used together in combination. For example, systems for identifying correlations between breast cancer susceptibility and polymorphisms can be used for practicing the methods herein. Kits can be used for practicing the methods herein. Thus, described features of the systems, methods and kits can be applied to the different systems, methods and kits herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1: depicts patients integrated lifetime risk.

Figure 2:
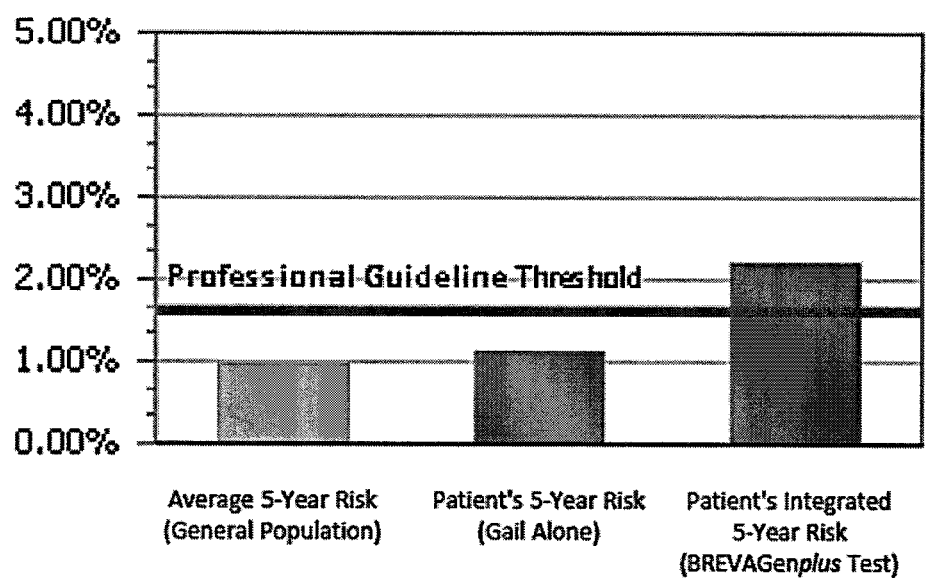

FIG. 2: depicts patients integrated 5 year risk.

FIG. 3: depicts SNPs indicative of breast cancer risk (n=88).

FIG. 4: depicts SNPs common across Caucasians. African American and Hispanic populations (n=70).

FIG. 5: depicts SNPs not common across Caucasians. African American and Hispanic populations (n=18).

FIG. 6: depicts analysis of hypothetical genotypes from three women of different ethnicity and calculation of genetic risk.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, breast cancer analysis, molecular genetics, immunology, immunohistochemistry, protein chemistry, and biochemistry).

Unless otherwise indicated, the molecular, and immunological techniques utilized in the present disclosure are standard procedures, well known to those skilled in the art. Such techniques are described and explained throughout the literature in sources such as, J. Perbal, A Practical Guide to Molecular Cloning. John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach. Volumes 1 and 2. IRL Press (1991). D. M. Glover and B. D. Flames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

It is to be understood that this disclosure is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a." "an" and "the," for example, optionally include plural referents unless the content clearly dictates otherwise. Thus, for example, reference to "a probe" optionally includes a plurality of probe molecules; similarly, depending on the context, use of the term "a nucleic acid" optionally includes, as a practical matter, many copies of that nucleic acid molecule.

As used herein, the term "about", unless stated to the contrary, refers to +/−10%, more preferably +/−5%, more preferably +/−1%, of the designated value.

As used herein, the term "breast cancer" encompasses any type of breast cancer that can develop in a female subject. For example, the breast cancer may be characterised as Luminal A (ER+ and/or PR+, HER2−, low Ki67), Luminal B (ER+ and/or PR+, HER2+(or HER2− with high Ki67), Triple negative/basal-like (ER−, PR−, HER2−) or HER2 type (ER−, PR−, HER2+). In another example, the breast cancer may be resistant to therapy or therapies such as alkylating agents, platinum agents, taxanes. *vinca* agents, anti-estrogen drugs, aromatase inhibitors, ovarian suppression agents, endocrine/hormonal agents, bisphophonate therapy agents or targeted biological therapy agents. As used herein. "breast cancer" also encompasses a phenotype that displays a predisposition towards developing breast cancer in an individual. A phenotype that displays a predisposition for breast cancer, can, for example, show a higher likelihood that the cancer will develop in an individual with the phenotype than in members of a relevant general population under a given set of environmental conditions (diet, physical activity regime, geographic location, etc.).

As used herein. "biological sample" refers to any sample comprising nucleic acids, especially DNA, from or derived from a human patient. e.g., bodily fluids (blood, saliva, urine etc.), biopsy, tissue, and/or waste from the patient. Thus, tissue biopsies, stool, sputum, saliva, blood, lymph, or the like can easily be screened for SNPs, as can essentially any tissue of interest that contains the appropriate nucleic acids. In one embodiment, the biological sample is a cheek cell sample. These samples are typically taken, following informed consent, from a patient by standard medical laboratory methods. The sample may be in a form taken directly from the patient, or may be at least partially processed (purified) to remove at least some non-nucleic acid material.

A "polymorphism" is a locus that is variable; that is, within a population, the nucleotide sequence at a polymorphism has more than one version or allele. One example of a polymorphism is a "single nucleotide polymorphism", which is a polymorphism at a single nucleotide position in a genome (the nucleotide at the specified position varies between individuals or populations).

As used herein, the term "SNP" or "single nucleotide polymorphism" refers to a genetic variation between individuals: e.g., a single nitrogenous base position in the DNA of organisms that is variable. As used herein. "SNPs" is the plural of SNP. Of course, when one refers to DNA herein, such reference may include derivatives of the DNA such as amplicons. RNA transcripts thereof, etc.

The term "allele" refers to one of to or more different nucleotide sequences that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. An allele "positively" correlates with a trait when it is linked to it and when presence of the allele is an indicator that the trait or trait form will occur in an individual comprising the allele. An allele "negatively" correlates with a trait when it is linked to it and when presence of the allele is an indicator that a trait or trait form will not occur in an individual comprising the allele.

A marker polymorphism or allele is "correlated" or "associated" with a specified phenotype (breast cancer susceptibility, etc.) when it can be statistically linked (positively or negatively) to the phenotype. Methods for determining whether a polymorphism or allele is statistically linked are known to those in the art. That is, the specified polymorphism occurs more commonly in a case population (e.g., breast cancer patients) than in a control population (e.g., individuals that do not have breast cancer). This correlation is often inferred as being causal in nature, but it need not be, simple genetic linkage to (association with) a locus for a trait that underlies the phenotype is sufficient for correlation/ association to occur.

The phrase "linkage disequilibrium" (LD) is used to describe the statistical correlation between two neighbouring polymorphic genotypes. Typically, LD refers to the correlation between the alleles of a random gamete at the two loci, assuming Hardy-Weinberg equilibrium (statistical independence) between gametes. LD is quantified with either Lewontin's parameter of association (D') or with Pearson correlation coefficient (r) (Devlin and Risch, 1995). Two loci with a LD value of 1 are said to be in complete LD. At the other extreme, two loci with a LD value of 0 are termed to be in linkage equilibrium. Linkage disequilibrium is calculated following the application of the expectation maximization algorithm (EM) for the estimation of haplotype frequencies (Slatkin and Excoffier, 1996). LD values according to the present disclosure for neighbouring genotypes/loci are selected above 0.1, preferably, above 0.2, more preferable above 0.5, more preferably, above 0.6, still more preferably, above 0.7, preferably, above 0.8, more preferably above 0.0, ideally about 1.0.

Another way one of skill in the art can readily identify SNPs in linkage disequilibrium with the SNPs of the present disclosure is determining the LOD score for two loci. LOD stands for "logarithm of the odds", a statistical estimate of whether two genes, or a gene and a disease gene, are likely to be located near each other on a chromosome and are therefore likely to be inherited. A LOD score of between about 2-3 or higher is generally understood to mean that two genes are located close to each other on the chromosome. Various examples of SNPs in linkage disequilibrium with the SNPs of the present disclosure are shown in Tables 1 to 4. The present inventors have found that many of the SNPs in linkage disequilibrium with the SNPs of the present disclosure have a LOD score of between about 2-50. Accordingly, in an embodiment. LOD values according to the present disclosure for neighbouring genotypes/loci are selected at least above 2, at least above 3, at least above 4, at least above 5, at least above 6, at least above 7, at least above 8, at least above 9, at least above 10, at least above 20 at least above 30, at least above 40, at least above 50.

In another embodiment, SNPs in linkage disequilibrium with the SNPs of the present disclosure can have a specified genetic recombination distance of less than or equal to about 20 centimorgan (cM) or less. For example, 15 cM or less, 10 cM or less, 9 cM or less, 8 cM or less, 7 cM or less, 6 cM or less, 5 cM or less, 4 cM or less, 3 cM or less, 2 cM or less, 1 cM or less, 0.75 cM or less, 0.5 cM or less, 0.25 cM or less, or 0.1 cM or less. For example, two linked loci within a single chromosome segment can undergo recombination during meiosis with each other at a frequency of less than or equal to about 20%, about 19%, about 18%, about 17%, about 16%, about 15%, about 14%, about 13%, about 12%, about 1%, about 10%, about 9%, about 8%, about 7%, about 6%, about 5%, about 4%, about 3%, about 2%, about 1%, about 0.75%, about 0.5%, about 0.25%, or about 0.1% or less.

In another embodiment, SNPs in linkage disequilibrium with the SNPs of the present disclosure are within at least 100 kb (which correlates in humans to about 0.1 cM, depending on local recombination rate), at least 50 kb, at least 20 kb or less of each other.

For example, one approach for the identification of surrogate markers for a particular SNP involves a simple strategy that presumes that SNPs surrounding the target SNP are in linkage disequilibrium and can therefore provide information about disease susceptibility. Thus, as described herein, surrogate markers can therefore be identified from publicly available databases, such as HAPMAP, by searching for SNPs fulfilling certain criteria which have been found in the scientific community to be suitable for the selection of surrogate marker candidates (see, for example, the legends of Tables 1 to 4).

"Allele frequency" refers to the frequency (proportion or percentage) at which an allele is present at a locus within an individual, within a line or within a population of lines. For example, for an allele "A." diploid individuals of genotype "AA." "Aa." or "aa" have allele frequencies of 1.0, 0.5, or 0.0, respectively. One can estimate the allele frequency within a line or population (e.g., cases or controls) by averaging the allele frequencies of a sample of individuals from that line or population. Similarly, one can calculate the allele frequency within a population of lines by averaging the allele frequencies of lines that make up the population.

In an embodiment, the term "allele frequency" is used to define the minor allele frequency (MAF). MAF refers to the frequency at which the least common allele occurs in a given population.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal position or region. For example, a polymorphic locus is a position or region where a polymorphic nucleic acid, trait determinant, gene or marker is located. In a further example, a "gene locus" is a specific chromosome location (region) in the genome of a species where a specific gene can be found.

A "marker." "molecular marker" or "marker nucleic acid" refers to a nucleotide sequence or encoded product thereof (e.g., a protein) used as a point of reference when identifying a locus or a linked locus. A marker can be derived from genomic nucleotide sequence or from expressed nucleotide sequences (e.g., from an RNA, nRNA, mRNA, a cDNA, etc.), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus. e.g., a nucleic acid probe that is complementary to a marker locus sequence. Nucleic acids are "complementary" when they specifically hybridize in solution. e.g., according to Watson-Crick base pairing rules. A "marker locus" is a locus that can be used to track the presence of a second linked locus. e.g., a linked or correlated locus that encodes or contributes to the population variation of a phenotypic trait. For example, a marker locus can be used to monitor segregation of alleles at a locus, such as a QTL, that are genetically or physically linked to the marker locus. Thus, a "marker allele." alternatively an "allele of a marker locus" is one of a plurality of polymorphic nucleotide sequences found at a marker locus in a population that is polymorphic for the marker locus. Each of the identified markers is expected to be in close physical and genetic proximity (resulting in physical and/or genetic linkage) to a genetic element. e.g., a QTL, that contributes to the relevant phenotype. Markers corresponding to genetic polymorphisms between members of a population can be detected by methods well-established in the art. These include. e.g., PCR-based sequence specific amplification methods, detection of restriction fragment length polymorphisms (RFLP), detection of isozyme markers, detection of allele specific hybridization (ASH), detection of single nucleotide extension, detection of amplified variable sequences of the genome, detection of self-sustained sequence replication, detection of simple sequence repeats (SSRs), detection of single nucleotide polymorphisms (SNPs), or detection of amplified fragment length polymorphisms (AFLPs).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., b transcription) methods.

An "amplicon" is an amplified nucleic acid, e.g., a nucleic acid that is produced by amplifying a template nucleic acid by any available amplification method (e.g., PCR, LCR, transcription, or the like).

A "gene" is one or more sequence(s) of nucleotides in a genome that together encode one or more expressed molecules, e.g., an RNA, or polypeptide. The gene can include coding sequences that are transcribed into RNA which may then be translated into a polypeptide sequence, and can include associated structural or regulator) sequences that aid in replication or expression of the gene.

A "genotype" is the genetic constitution of an individual (or group of individuals) at one or more genetic loci. Genotype is defined by the allele(s) of one or more known loci of the individual, typically, the compilation of alleles inherited from its parents.

A "haplotype" is the genotype of an individual at a plurality of genetic loci on a single DNA strand. Typically, the genetic loci described by a haplotype are physically and genetically linked, i.e., on the same chromosome strand.

A "set" of markers, probes or primers refers to a collection or group of markers probes, primers, or the data derived therefrom, used for a common purpose. e.g., identifying an individual with a specified genotype (e.g., risk of developing breast cancer). Frequently, data corresponding to the markers, probes or primers, or derived from their use, is stored in an electronic medium. While each of the members of a set possess utility with respect to the specified purpose, individual markers selected from the set as well as subsets including some, but not all of the markers, are also effective in achieving the specified purpose.

The polymorphisms and genes, and corresponding marker probes, amplicons or primers described above can be embodied in any system herein, either in the form of physical nucleic acids, or in the form of system instructions that include sequence information for the nucleic acids. For example, the system can include primers or amplicons corresponding to (or that amplify a portion of) a gene or polymorphism described herein. As in the methods above, the set of marker probes or primers optionally detects a plurality of polymorphisms in a plurality of said genes or genetic loci. Thus, for example, the set of marker probes or primers detects at least one polymorphism in each of these polymorphisms or genes, or any other polymorphism, gene or locus defined herein. Any such probe or primer can include a nucleotide sequence of any such polymorphism or gene, or a complementary nucleic acid thereof, or a transcribed product thereof (e.g., a nRNA or mRNA form produced from a genomic sequence. e.g., by transcription or splicing).

As used herein. "Receiver operating characteristic curves" refer to a graphical plot of the sensitivity vs. (1—specificity) for a binary classifier system as its discrimination threshold is varied. The ROC can also be represented equivalently by plotting the fraction of true positives (TPR=true positive rate) vs. the fraction of false positives (FPR=false positive rate). Also known as a Relative Operating Characteristic curve, because it is a comparison of two operating characteristics (TPR & FPR) as the criterion changes. ROC analysis provides tools to select possibly optimal models and to discard suboptimal ones independently from (and prior to specifying) the cost context or the class distribution. Methods of using in the context of the disclosure will be clear to those skilled in the art.

As used herein, the term "combining the clinical risk assessment with the genetic risk assessment to obtain the risk" refers to any suitable mathematical analysis relying on the results of the two assessments. For example, the results of the clinical risk assessment and the genetic risk assessment may be added, more preferably multiplied.

As used herein, the terms "routinely screening for breast cancer" and "more frequent screening" are relative terms, and are based on a comparison to the level of screening recommended to a subject who has no identified risk of developing breast cancer.

Ethnic Genotype Variation

It is known to those of skill in the art that genotypic variation exists between different populations. This phenomenon is referred to as human genetic variation. Human genetic variation is often observed between populations from different ethnic backgrounds. Such variation is rarely consistent and is often directed by various combinations of environmental and lifestyle factors. As a result of genetic variation, it is often difficult to identify a population of genetic markers such as SNPs that remain informative across various populations such as populations from different ethnic backgrounds.

Surprisingly, the present inventors have identified a selection of SNPs that are common to at least three ethnic backgrounds that remain informative for assessing the risk for developing breast cancer.

Accordingly, it is envisaged that the methods of the present disclosure can be used for assessing the risk or developing breast cancer in human female subjects from various ethnic backgrounds. For example, the female can be classified as Caucasoid, Australoid, Mongoloid and Negroid based on physical anthropology.

In an embodiment, the human female subject can be Caucasian, African American, Hispanic, Asian, Indian, or Latino. In a preferred embodiment, the human female subject is Caucasian, African American or Hispanic.

In one embodiment, the human female subject is Caucasian and at least 72, at least 73, at least 74, at least 75, at least 76, at least 77, single nucleotide polymorphisms selected from Table 9, or a single nucleotide polymorphism in linkage disequilibrium therewith are assessed. Alternatively, at least 77 single nucleotide polymorphisms selected from Table 9 or a single nucleotide polymorphism in linkage disequilibrium there with are assessed.

In another embodiment, the human female subject can be Negroid and at least 74, at least 75, at least 76, at least 77, at least 78, single nucleotide polymorphisms selected from Table 10, or a single nucleotide polymorphism in linkage disequilibrium therewith are assessed. Alternatively, at least 78 single nucleotide polymorphisms selected from Table 10 or a single nucleotide polymorphism in linkage disequilibrium therewith are assessed.

In another embodiment, the human female subject can be African American and at least 74, at least 75, at least 76, at least 77, at least 78, single nucleotide polymorphisms selected from Table 10, or a single nucleotide polymorphism in linkage disequilibrium therewith are assessed. Alternatively, at least 78 single nucleotide polymorphisms selected from Table 10 or a single nucleotide polymorphism in linkage disequilibrium therewith are assessed.

In a further embodiment, the human female subject can be Hispanic and at least 78, at least 79, at least 80, at least 81, at least 82, single nucleotide polymorphisms selected from Table 11, or a single nucleotide polymorphism in linkage disequilibrium therewith are assessed. Alternatively, at least 82 single nucleotide polymorphisms selected from Table 11 or a single nucleotide polymorphism in linkage disequilibrium therewith are assessed.

It is well known that over time there has been blending of different ethnic origins. However, in practice this does not influence the ability of a skilled person to practice the invention.

A female of predominantly European origin, either direct or indirect through ancestry, with white skin is considered Caucasian in the context of the present disclosure. A Caucasian may have, for example, at least 75% Caucasian ancestry (for example, but not limited to, the female having at least three Caucasian grandparents).

A female of predominantly central or southern African origin, either direct or indirect through ancestry, is considered Negroid in the context of the present disclosure. A Negroid may have, for example, at least 75% Negroid ancestry. An American female with predominantly Negroid ancestry and black skin is considered African American in the context of the present disclosure. An African American may have, for example, at least 75% Negroid ancestry. Similar principle applies to, for example, females of Negroid ancestry living in other countries (for example Great Britain, Canada of The Netherlands)

A female predominantly originating from Spain or a Spanish-speaking country, such as a country of Central or Southern America, either direct or indirect through ancestry, is considered Hispanic in the context of the present disclosure. An Hispanic may have, for example, at least 75% Hispanic ancestry.

The present inventors have found that the invention can readily be practiced based on what race/ancestry the subject considers themselves to be. Thus, in an embodiment, the ethnicity of the human female subject is self-reported by the subject.

As an example, female subjects can be asked to identify their ethnicity in response to this question: "To what ethnic group do you belong?"

In another example, the ethnicity of the female subject is derived from medical records after obtaining the appropriate consent from the subject or from the opinion or observations of a clinician.

Naturally, in cases where there is no predominant ancestry, for example 50% Caucasian and 50% Negroid, the invention can still be practiced by focussing on the common polymorphisms provided in Table 7.

Clinical Risk Assessment

Any suitable clinical risk assessment procedure can be used in the present disclosure. Preferably, the clinical risk assessment does not involve genotyping the female at one or more loci.

In an embodiment, the clinical risk assessment procedure includes obtaining information from the female on one or more of the following: medical history of breast cancer, ductal carcinoma or lobular carcinoma, age, menstrual history such as age of first menstrual period, age at which she first gave birth, family history of breast cancer or other cancer including the age of the relative at the time of diagnosis, results of previous breast biopsies, use of oral contraceptives, body mass index, alcohol consumption history, smoking history, exercise history, diet and race/ethnicity.

In an embodiment, the clinical risk assessment at least takes into consideration the age, number of previous breast biopsies and known history among first degree relatives.

In an embodiment the clinical risk assessment procedure provides an estimate of the risk of the human female subject developing breast cancer during the next 5-year period (i.e. 5-year risk).

In an embodiment the 5-year risk determined by the clinical risk assessment is between about 1% to about 3%.

In another embodiment the 5-year risk determined by the clinical risk assessment is between about 1.5% to about 2%.

In an embodiment the clinical risk assessment procedure provides an estimate of the risk of the human female subject developing breast cancer up to age 90 (i.e. lifetime risk).

In an embodiment the lifetime risk determined by the clinical risk assessment is between about 15% to about 30%.

In another embodiment the 5-year risk determined by the clinical risk assessment is between about 20% to about 25%.

Examples of clinical risk assessment procedures include, but are not limited to, the Gail Model (BCRAT) (Gail et al., 1989, 1999 and 2007: Costantino et al., 1999; Rockhill et al., 2001), the Claus model (Claus et al., 1994 and 1998), Claus Tables. BOADICEA (Antoniou et al., 2002 and 2004), BRCAPRO (Parmigiani et al., 2007), the Jonker Model (Jonker et al., 2003), the Claus Extended Formula (van Asperen et al., 2004), the Tyrer-Cuzick Model (Tyrer et al., 2004), the Manchester Scoring System (Evans et al., 2004) and the like.

In an example, the clinical risk assessment procedure is the Gail Model. Such procedures can be used to estimate the 5-year risk or lifetime risk of a human female subject. The Gail Model is a statistical model which forms the basis of a breast cancer risk assessment tool, named after Dr. Mitchell Gail, Senior Investigator in the Biostatistics Branch of NCI's Division of Cancer Epidemiology and Genetics. The model uses a woman's own personal medical history (number of previous breast biopsies and the presence of atypical hyperplasia in any previous breast biopsy specimen), her own reproductive history (age at the start of menstruation and age at the first live birth of a child), and the history of breast cancer among her first-degree relatives (mother, sisters, daughters) to estimate her risk of developing invasive breast cancer over specific periods of time. Data from the Breast Cancer Detection Demonstration Project (BCDDP), which was a joint NCI and American Cancer Society breast cancer screening study that involved 280.000 women aged 35 to 74 years, and from NCI's Surveillance. Epidemiology. and End Results (SEER) Program were used in developing the model. Estimates for African American women were based on data from the Women's Contraceptive and Reproductive Experiences (CARE) Study and from SEER data.

CARE participants included 1.607 women with invasive breast cancer and 1.637 without.

The Gail model has been tested in large populations of white women and has been shown to provide accurate estimates of breast cancer risk. In other words, the model has been "validated" for white women. It has also been tested in data from the Women's Health Initiative for African American women, and the model performs well, but may underestimate risk in African American women with previous biopsies. The model has also been validated for Hispanic women, Asian American women and Native American women.

In another example, the clinical risk assessment procedure is the Tyrer-Cuzick model. The Tyrer-Cuzick model incorporates both genetic and non-genetic factors (Tyrer et al., 2004). Nonetheless, the Tyrer-Cuzick model is considered separate from the genetic risk assessment outlined in the present disclosure. The Tyrer-Cuzick uses a three-generation pedigree to estimate the likelihood that an individual carries either a BRCA1/BRCA2 mutation or a hypothetical low-penetrance gene. In addition, the model incorporates personal risk factors, such as parity, body mass index, height, and age at menarche, menopause, HRT use, and first live birth.

In another example, the clinical risk assessment procedure is the BOADICEA model. The BOADICEA model was designed with the use of segregation analysis in which susceptibility is explained by mutations in BRCA1 and BRCA2 as well as a polygenic component that reflects the multiplicative effect of multiple genes, which individually have small effects on breast cancer risk (Antoniou et al., 2002 and 2004). This algorithm allows for prediction of BRCA1 BRCA2 mutation probabilities and for cancer risk estimation in individuals with a family history of breast cancer.

In another example, the clinical risk assessment procedure is the BRCAPRO model. The BRCAPRO Model is a Bayesian model that incorporates published BRCA1 and BRCA2 mutation frequencies. Cancer penetrance in mutation carriers, cancer status (affected, unaffected, unknown) and age of the patient's first-degree and second degree relatives (Parmigiani et al., 1998). This algorithm allows for prediction of BRCA1/BRCA2 mutation probabilities and for cancer risk estimation in individuals with a family history of breast cancer.

In another example, the clinical risk assessment procedure is the Claus model. The Claus Model provides an assessment of hereditary risk of developing breast cancer. The model as developed using data from the Cancer and Steroid Hormone Study. The model originally only included data on family history of breast cancer (Claus et al., 1991), but was later updated to include data on family history of ovarian cancer (Claus et al., 1993). In practice, lifetime risk estimates are usually derived from so-called Claus Tables (Claus et al., 1994). The model was further modified to incorporate information on bilateral disease, ovarian cancer, and three or more affected relatives and termed the "Claus Extended Model" (van Asperen et al., 2004).

Genetic Risk Assessment

In one aspect, the methods of the present disclosure relate to assessing the risk of a female subject for developing breast cancer by performing a genetic risk assessment. In another aspect, these methods can also incorporate a clinical risk assessment to provide a combined risk for developing breast cancer.

The genetic risk assessment is performed by analysing the genotype of the subject at 72 or more loci for single nucleotide polymorphisms associated with breast cancer. As the skilled addressee will appreciate, each SNP which increases the risk of developing breast cancer has an odds ratio of association with breast cancer of greater than 1.0, more preferably greater than 1.02. Examples of such SNPs include, but are not limited to, those provided in Tables 6 to 11, or a single nucleotide polymorphism in linkage disequilibrium with one or more thereof.

As the skilled addressee will appreciate, each SNP which decreases the risk of developing breast cancer has an odds ratio of association with breast cancer of less than 1.0. In an embodiment, the odds ratio is less than 0.98.

In an embodiment, when performing the methods of the present disclosure at least 67 of the single nucleotide polymorphisms are selected from Table 7 or a single nucleotide polymorphism in linkage disequilibrium with one or more thereof and the remaining single nucleotide polymorphisms are selected from Table 6, or a single nucleotide polymorphism in linkage disequilibrium with one or more thereof. In another embodiment, when performing the methods of the present disclosure at least 68, at least 69, at least 70 of the single nucleotide polymorphisms are selected from Table 7 or a single nucleotide polymorphism in linkage disequilibrium with one or more thereof and the remaining single nucleotide polymorphisms are selected from Table 6, or a single nucleotide polymorphism in linkage disequilibrium with one or more thereof.

SNPs in linkage disequilibrium with those specifically mentioned herein are easily identified by those of skill in the art. Examples of such SNPs include rs1219648 and rs2420946 which are in strong linkage disequilibrium with rs2981582 (further possible examples provided in Table 1), rs12443621 and rs8051542 which are in strong linkage disequilibrium with SNP rs3803662 (further possible examples provided in Table 2), and rs10941679 which is in strong linkage disequilibrium with SNP rs4415084 (further possible examples provided in Table 3). In addition, examples of SNPs in linkage disequilibrium with rs13387042 provided in Table 4. Such linked polymorphisms for the other SNPs listed in Table 6 can very easily be identified by the skilled person using the HAPMAP database.

In one embodiment, at least 72, at least 73, at least 74, at least 75, at least 76, at least 78, at least 79, at least 80, at least 81, at least 82, at least 83, at least 84, at least 85, at least 86, at least 87, at least 88 of single nucleotide polymorphisms shown in Table 6, or a single nucleotide polymorphism in linkage disequilibrium with one or more thereof are assessed. In further embodiments, at least 67, at least 68, at least 69, at least 70, shown in Table 7, or a single nucleotide polymorphism in linkage disequilibrium with one or more thereof are assessed.

In further embodiments, at least 70, at least 71, at least 72, at least 73, at least 74, at least 75, at least 76, at least 78, at least 79, at least 80, at least 81, at least 82, at least 83, at least 84, at least 85, at least 86, at least 87, at least 88 single nucleotide polymorphisms are assessed, wherein at least 67, at least 68, at least 69, at least 70, shown in Table 7, or a single nucleotide polymorphism in linkage disequilibrium with one or more thereof are assessed, with any remaining SNPs being selected from Table 6, or a single nucleotide polymorphism in linkage disequilibrium with one or more thereof.

TABLE 1

Surrogate markers for SNP rs2981582. Markers with a r2 greater than 0.05 to rs2981582 in the HAPMAP dataset (hapmap.ncbi.nlm.nih.gov) in a 1 Mbp interval flanking the marker was selected. Shown is the name of the correlated SNP, values for r2 and D' to rs2981582 and the corresponding LOD value, as well as the position of the surrogate marker in NCB Build 36.

| DbSNP rsID | Position | Correlated SNP | Location | D' | $r^2$ | LOD |
|---|---|---|---|---|---|---|
| rs2981582 | 123342307 | rs3135715 | 123344716 | 1.000 | 0.368 | 15.02 |
| rs2981582 | 123342307 | rs7899765 | 123345678 | 1.000 | 0.053 | 2.44 |
| rs2981582 | 123342307 | rs1047111 | 123347551 | 0.938 | 0.226 | 9.11 |
| rs2981582 | 123342307 | rs1219639 | 123348302 | 1.000 | 0.143 | 6.53 |
| rs2981582 | 123342307 | rs10886955 | 123360344 | 0.908 | 0.131 | 5.42 |
| rs2981582 | 123342307 | rs1631281 | 123380775 | 0.906 | 0.124 | 5.33 |
| rs2981582 | 123342307 | rs3104685 | 123381354 | 0.896 | 0.108 | 4.58 |
| rs2981582 | 123342307 | rs1909670 | 123386718 | 1.000 | 0.135 | 6.12 |
| rs2981582 | 123342307 | rs7917459 | 123392364 | 1.000 | 0.135 | 6.42 |
| rs2981582 | 123342307 | rs17102382 | 123393846 | 1.000 | 0.135 | 6.42 |
| rs2981582 | 123342307 | rs10788196 | 123407625 | 1.000 | 0.202 | 9.18 |
| rs2981582 | 123342307 | rs2935717 | 123426236 | 0.926 | 0.165 | 7.30 |
| rs2981582 | 123342307 | rs3104688 | 123426455 | 0.820 | 0.051 | 2.07 |
| rs2981582 | 123342307 | rs4752578 | 123426514 | 1.000 | 0.106 | 5.15 |
| rs2981582 | 123342307 | rs1696803 | 123426940 | 0.926 | 0.168 | 7.33 |
| rs2981582 | 123342307 | rs12262574 | 123428112 | 1.000 | 0.143 | 7.39 |
| rs2981582 | 123342307 | rs4752579 | 123431182 | 1.000 | 0.106 | 5.15 |
| rs2981582 | 123342307 | rs12358208 | 123460953 | 0.761 | 0.077 | 2.46 |
| rs2981582 | 123342307 | rs17102484 | 123462020 | 0.758 | 0.065 | 2.39 |
| rs2981582 | 123342307 | rs2936859 | 123469277 | 0.260 | 0.052 | 1.56 |
| rs2981582 | 123342307 | rs10160140 | 123541979 | 0.590 | 0.016 | 0.40 |

TABLE 2

Surrogate markers for SNP rs3803662. Markers with a r2 greater than 0.05 to rs3803662 in the HAPMAP dataset (hapmap.ncbi.nlm.nih.gov) in a 1 Mbp interval flanking the marker was selected. Shown is the name of the correlated SNP, values for r2 and D' to rs3803662 and the corresponding LOD value, as well as the position of the surrogate marker in NCB Build 36.

| DbSNP rsID | Position | Correlated SNP | Location | D' | $r^2$ | LOD |
|---|---|---|---|---|---|---|
| rs3803662 | 51143842 | rs4784227 | 51156689 | 0.968 | 0.881 | 31.08 |
| rs3803662 | 51143842 | rs3112572 | 51157948 | 1.000 | 0.055 | 1.64 |
| rs3803662 | 51143842 | rs3104747 | 51159425 | 1.000 | 0.055 | 1.64 |
| rs3803662 | 51143842 | rs3104748 | 51159860 | 1.000 | 0.055 | 1.64 |
| rs3803662 | 51143842 | rs3104750 | 51159990 | 1.000 | 0.055 | 1.64 |
| rs3803662 | 51143842 | rs3104758 | 51166534 | 1.000 | 0.055 | 1.64 |
| rs3803662 | 51143842 | rs3104759 | 51167030 | 1.000 | 0.055 | 1.64 |
| rs3803662 | 51143842 | rs9708611 | 51170166 | 1.000 | 0.169 | 4.56 |
| rs3803662 | 51143842 | rs12935019 | 51170538 | 1.000 | 0.088 | 4.04 |
| rs3803662 | 51143842 | rs4784230 | 51175614 | 1.000 | 0.085 | 4.19 |
| rs3803662 | 51143842 | rs11645620 | 51176454 | 1.000 | 0.085 | 4.19 |
| rs3803662 | 51143842 | rs3112633 | 51178078 | 1.000 | 0.085 | 4.19 |
| rs3803662 | 51143842 | rs3104766 | 51182036 | 0.766 | 0.239 | 7.55 |
| rs3803662 | 51143842 | rs3104767 | 51182239 | 0.626 | 0.167 | 4.88 |
| rs3803662 | 51143842 | rs3112625 | 51183053 | 0.671 | 0.188 | 5.62 |
| rs3803662 | 51143842 | rs12920540 | 51183114 | 0.676 | 0.195 | 5.84 |
| rs3803662 | 51143842 | rs3104774 | 51187203 | 0.671 | 0.188 | 5.62 |
| rs3803662 | 51143842 | rs7203671 | 51187646 | 0.671 | 0.188 | 5.62 |
| rs3803662 | 51143842 | rs3112617 | 51189218 | 0.666 | 0.177 | 5.44 |
| rs3803662 | 51143842 | rs11075551 | 51189465 | 0.666 | 0.177 | 5.44 |
| rs3803662 | 51143842 | rs12929797 | 51190445 | 0.676 | 0.19 | 5.87 |
| rs3803662 | 51143842 | rs3104780 | 51191415 | 0.671 | 0.184 | 5.65 |
| rs3803662 | 51143842 | rs12922061 | 51192501 | 0.832 | 0.631 | 19.14 |
| rs3803662 | 51143842 | rs3112612 | 51192665 | 0.671 | 0.184 | 5.65 |
| rs3803662 | 51143842 | rs3104784 | 51193866 | 0.666 | 0.177 | 5.44 |
| rs3803662 | 51143842 | rs12597685 | 51195281 | 0.671 | 0.184 | 5.65 |
| rs3803662 | 51143842 | rs3104788 | 51196004 | 0.666 | 0.177 | 5.44 |
| rs3803662 | 51143842 | rs3104800 | 51203877 | 0.625 | 0.17 | 4.99 |
| rs3803662 | 51143842 | rs3112609 | 51206232 | 0.599 | 0.163 | 4.86 |
| rs3803662 | 51143842 | rs3112600 | 51214089 | 0.311 | 0.016 | 0.57 |
| rs3803662 | 51143842 | rs3104807 | 51215026 | 0.302 | 0.014 | 0.52 |
| rs3803662 | 51143842 | rs3112594 | 51229030 | 0.522 | 0.065 | 1.56 |
| rs3803662 | 51143842 | rs4288991 | 51230665 | 0.238 | 0.052 | 1.53 |
| rs3803662 | 51143842 | rs3104820 | 51233304 | 0.528 | 0.069 | 1.60 |
| rs3803662 | 51143842 | rs3104824 | 51236594 | 0.362 | 0.067 | 1.93 |

TABLE 2-continued

Surrogate markers for SNP rs3803662. Markers with a r2 greater than 0.05 to rs3803662 in the HAPMAP dataset (hapmap.ncbi.nlm.nih.gov) in a 1 Mbp interval flanking the marker was selected. Shown is the name of the correlated SNP, values for r2 and D' to rs3803662 and the corresponding LOD value, as well as the position of the surrogate marker in NCB Build 36.

| DbSNP rsID | Position | Correlated SNP | Location | D' | r² | LOD |
|---|---|---|---|---|---|---|
| rs3803662 | 51143842 | rs3104826 | 51237406 | 0.362 | 0.067 | 1.93 |
| rs3803662 | 51143842 | rs3112588 | 51238502 | 0.354 | 0.062 | 1.80 |

TABLE 3

Surrogate markers for SNP rs4415084. Markers with a r2 greater than 0.05 to rs4415084 in the HAPMAP dataset (hapmap.ncbi.nlm.nih.gov) in a 1 Mbp interval flanking the marker was selected. Shown is the name of the correlated SNP, values for r2 and D' to rs4415084 and the corresponding LOD value, as well as the position of the surrogate marker in NCB Build 36.

| DbSNP rsID | Position | Correlated SNP | Location | D' | r² | LOD |
|---|---|---|---|---|---|---|
| rs4415084 | 44698272 | rs12522626 | 44721455 | 1.000 | 1.0 | 47.37 |
| rs4415084 | 44698272 | rs4571480 | 44722945 | 1.000 | 0.976 | 40.54 |
| rs4415084 | 44698272 | rs6451770 | 44727152 | 1.000 | 0.978 | 44.88 |
| rs4415084 | 44698272 | rs920328 | 44734808 | 1.000 | 0.893 | 39.00 |
| rs4415084 | 44698272 | rs920329 | 44738264 | 1.000 | 1.0 | 47.37 |
| rs4415084 | 44698272 | rs2218081 | 44740897 | 1.000 | 1.0 | 47.37 |
| rs4415084 | 44698272 | rs16901937 | 44744898 | 1.000 | 0.978 | 45.06 |
| rs4415084 | 44698272 | rs11747159 | 44773467 | 0.948 | 0.747 | 28.79 |
| rs4415084 | 44698272 | rs2330572 | 44776746 | 0.952 | 0.845 | 34.31 |
| rs4415084 | 44698272 | rs994793 | 44779004 | 0.952 | 0.848 | 34.49 |
| rs4415084 | 44698272 | rs1438827 | 44787713 | 0.948 | 0.749 | 29.76 |
| rs4415084 | 44698272 | rs7712949 | 44806102 | 0.948 | 0.746 | 29.19 |
| rs4415084 | 44698272 | rs11746980 | 44813635 | 0.952 | 0.848 | 34.49 |
| rs4415084 | 44698272 | rs16901964 | 44819012 | 0.949 | 0.768 | 30.54 |
| rs4415084 | 44698272 | rs727305 | 44831799 | 0.972 | 0.746 | 27.65 |
| rs4415084 | 44698272 | rs10462081 | 44836422 | 0.948 | 0.749 | 29.76 |
| rs4415084 | 44698272 | rs13183209 | 44839506 | 0.925 | 0.746 | 28.55 |
| rs4415084 | 44698272 | rs13159598 | 44841683 | 0.952 | 0.848 | 34.19 |
| rs4415084 | 44698272 | rs3761650 | 44844113 | 0.947 | 0.744 | 28.68 |
| rs4415084 | 44698272 | rs13174122 | 44846497 | 0.971 | 0.735 | 26.70 |
| rs4415084 | 44698272 | rs11746506 | 44848323 | 0.973 | 0.764 | 29.24 |
| rs4415084 | 44698272 | rs7720787 | 44853066 | 0.952 | 0.845 | 34.31 |
| rs4415084 | 44698272 | rs9637783 | 44855403 | 0.948 | 0.748 | 29.16 |
| rs4415084 | 44698272 | rs4457089 | 44857493 | 0.948 | 0.762 | 29.70 |
| rs4415084 | 44698272 | rs6896350 | 44868328 | 0.948 | 0.764 | 29.46 |
| rs4415084 | 44698272 | rs1371025 | 44869990 | 0.973 | 0.785 | 30.69 |
| rs4415084 | 44698272 | rs4596389 | 44872313 | 0.948 | 0.749 | 29.76 |
| rs4415084 | 44698272 | rs6451775 | 44872545 | 0.948 | 0.746 | 29.19 |
| rs4415084 | 44698272 | rs729599 | 44878017 | 0.948 | 0.748 | 29.16 |
| rs4415084 | 44698272 | rs987394 | 44882135 | 0.948 | 0.749 | 29.76 |
| rs4415084 | 44698272 | rs4440370 | 44889109 | 0.948 | 0.748 | 29.16 |
| rs4415084 | 44698272 | rs7703497 | 44892785 | 0.948 | 0.749 | 29.76 |
| rs4415084 | 44698272 | rs13362132 | 44894017 | 0.952 | 0.827 | 34.09 |
| rs4415084 | 44698272 | rs1438821 | 44894208 | 0.951 | 0.844 | 34.52 |

TABLE 4

Surrogate markers for SNP rs13387042. Markers with a r2 greater than 0.05 to rs13387042 in the HAPMAP dataset (hapmap.ncbi.nlm.nih.gov) in a 1 Mbp interval flanking the marker was selected. Shown is the name of the correlated SNP, values for r2 and D' to rs13387042 and the corresponding LOD value, as well as the position of the surrogate marker in NCB Build 36.

| DbSNP rsID | Position | Correlated SNP | Location | D' | r² | LOD |
|---|---|---|---|---|---|---|
| rs13387042 | 217614077 | rs4621152 | 217617230 | 0.865 | 0.364 | 15.30 |
| rs13387042 | 217614077 | rs6721996 | 217617708 | 1.000 | 0.979 | 50.46 |
| rs13387042 | 217614077 | rs12694403 | 217623659 | 0.955 | 0.33 | 14.24 |
| rs13387042 | 217614077 | rs17778427 | 217631258 | 1.000 | 0.351 | 16.12 |
| rs13387042 | 217614077 | rs17835044 | 217631850 | 1.000 | 0.351 | 16.12 |
| rs13387042 | 217614077 | rs7588345 | 217632061 | 1.000 | 0.193 | 8.93 |
| rs13387042 | 217614077 | rs7562029 | 217632506 | 1.000 | 0.413 | 20.33 |

TABLE 4-continued

Surrogate markers for SNP rs13387042. Markers with a r2 greater than 0.05 to rs13387042 in the HAPMAP dataset (hapmap.ncbi.nlm.nih.gov) in a 1 Mbp interval flanking the marker was selected. Shown is the name of the correlated SNP, values for r2 and D' to rs13387042 and the corresponding LOD value, as well as the position of the surrogate marker in NCB Build 36.

| DbSNP rsID | Position | Correlated SNP | Location | D' | r² | LOD |
| --- | --- | --- | --- | --- | --- | --- |
| rs13387042 | 217614077 | rs13000023 | 217632639 | 0.949 | 0.287 | 12.20 |
| rs13387042 | 217614077 | rs13409592 | 217634573 | 0.933 | 0.192 | 7.69 |
| rs13387042 | 217614077 | rs2372957 | 217635302 | 0.855 | 0.168 | 5.97 |
| rs13387042 | 217614077 | rs16856888 | 217638914 | 0.363 | 0.101 | 3.31 |
| rs13387042 | 217614077 | rs16856890 | 217639976 | 0.371 | 0.101 | 3.29 |
| rs13387042 | 217614077 | rs7598926 | 217640464 | 0.382 | 0.109 | 3.60 |
| rs13387042 | 217614077 | rs6734010 | 217643676 | 0.543 | 0.217 | 7.90 |
| rs13387042 | 217614077 | rs13022815 | 217644369 | 0.800 | 0.319 | 12.94 |
| rs13387042 | 217614077 | rs16856893 | 217645298 | 0.739 | 0.109 | 3.45 |
| rs13387042 | 217614077 | rs13011060 | 217646422 | 0.956 | 0.352 | 14.71 |
| rs13387042 | 217614077 | rs4674132 | 217646764 | 0.802 | 0.327 | 13.10 |
| rs13387042 | 217614077 | rs16825211 | 217647249 | 0.912 | 0.326 | 12.95 |
| rs13387042 | 217614077 | rs41521045 | 217647581 | 0.903 | 0.112 | 4.70 |
| rs13387042 | 217614077 | rs2372960 | 217650960 | 0.678 | 0.058 | 2.12 |
| rs13387042 | 217614077 | rs2372967 | 217676158 | 0.326 | 0.052 | 1.97 |
| rs13387042 | 217614077 | rs3843337 | 217677680 | 0.326 | 0.052 | 1.97 |
| rs13387042 | 217614077 | rs2372972 | 217679386 | 0.375 | 0.062 | 2.28 |
| rs13387042 | 217614077 | rs9677455 | 217680497 | 0.375 | 0.062 | 2.28 |
| rs13387042 | 217614077 | rs12464728 | 217686802 | 0.478 | 0.073 | 2.54 |

In one embodiment, the methods of the present disclosure encompass assessing all of the SNPs shown in Fable 6 or a single nucleotide polymorphism in linkage disequilibrium with one or more thereof.

Table 6 and Table 7 recite overlapping SNPs. It will be appreciated that when selecting SNPs for assessment the same SNP will not be selected twice. For convenience, the SNPs in Table 6 have been separated into Tables 7 and 8. Table 7 lists SNPs common across Caucasians, African American and Hispanic populations. Table 8 lists SNPs that are not common across Caucasians, African American and Hispanic populations.

In a further embodiment, between 72 and 88, between 73 and 87, between 74 and 86, between 75 and 85, between 76 and 87, between 75 and 86, between 76 and 85, between 77 and 84, between 78 and 83, between 79 and 82, between 80 and 81 single nucleotide polymorphisms are assessed, wherein at least 60, at least 61, at least 62, at least 63, at least 64, at least 65, at least 66, at least 67, at least 68, at least 69, at least 70, of the SNPs shown in Table 7, or a single nucleotide polymorphism in linkage disequilibrium with one or more thereof are assessed, with any remaining SNPs being selected from Table 6, or a single nucleotide polymorphism in linkage disequilibrium with one or more thereof In an embodiment, the number of SNPs assessed is based on the net reclassification improvement in risk prediction calculated using net reclassification index (NRI) (Pencina et al., 2008).

In an embodiment, the net reclassification improvement of the methods of the present disclosure is greater than 0.01.

In a further embodiment, the net reclassification improvement of the methods of the present disclosure is greater than 0.05.

In yet another embodiment the net reclassification improvement of the methods of the present disclosure is greater than 0.1.

Calculating Composite SNP Relative Risk "SNP Risk"

An individual's composite SNP relative risk score ("SNP risk") can be defined as the product of genotype relative risk values for each SNPs assessed. A log-additive risk model can then be used to define three genotypes AA, AB, and BB for a single SNP having relative risk values of 1, OR, and $OR^2$, under a rare disease model, where OR is the previously reported disease odds ratio for the high-risk allele, B, vs the low-risk allele, A. If the B allele has frequency (p), then these genotypes have population frequencies of $(1-p)^2$, $2p(1-p)$, and $p^2$, assuming Hardy-Weinberg equilibrium. The genotype relative risk values for each SNP can then be scaled so that based on these frequencies the average relative risk in the population is 1. Specifically, given the unsealed population average relative risk:

$$(\mu)=(1-p)^2+2p(1-p)OR+p^2OR^2$$

Adjusted risk values $1/\mu$, $OR/\mu$, and $OR^2/\mu$ are used for AA, AB, and BB genotypes.

Missing genotypes are assigned a relative risk of 1.

Similar calculations can be performed for non-SNP polymorphisms.

Combined Clinical Assessment×Genetic Risk Score

In combining the clinical risk assessment with the genetic risk assessment to obtain the "risk" of a human female subject for developing breast cancer, the following formula can be used:

[Risk (i.e. Clinical Evaluation×SNP risk)]=[Clinical Evaluation risk]×$SNP_1$×$SNP_2$×$SNP_3$×$SNP_4$× $SNP_5$×$SNP_6$×$SNP_7$×$SNP_8$. . . . ×$SNP_{72}$ etc.

This example relates to when the polymorphisms are SNPs but similar procedures can be used for non-SNP polymorphisms.

Where Clinical Evaluation is the risk score provided by the clinical evaluation, and $SNP_1$ to $SNP_{72}$ are relative risk scores for the individual SNPs, each scaled to have a population average of 1 as outlined above. Because the SNP risk scores have been "centred" to have a population average risk of 1, if one assumes independence among the SNPs, then the population average risk across all genotypes for the combined score is consistent with the underlying Clinical Evaluation risk estimate.

In an embodiment the risk of a human female subject for developing breast cancer is calculated by [Clinical Evaluation 5-year risk]×$SNP_1$×$SNP_2$×$SNP_3$×$SNP_4$×$SNP_5$×$SNP_6$× $SNP_7$,×$SNP_8$. . . . ×$SNP_{72}$ etc.

In another embodiment the risk of a human female subject for developing breast cancer is calculated by [Clinical Evaluation risk]×$SNP_1$×$SNP_2$×$SNP_3$×$SNP_4$×$SNP_5$×$SNP_6$× $SNP_7$, $SNP_8$. . . . ×$SNP_{72}$ etc.

In another embodiment the risk of a human female subject for developing breast cancer is calculated by [Clinical Evaluation lifetime risk]×$SNP_1$×$SNP_2$×$SNP_3$×$SNP_4$× $SNP_5$×$SNP_6$×$SNP_7$,×$SNP_8$. . . . ×$SNP_{72}$ etc.

In an embodiment, the Clinical Evaluation is performed using the Gail model to provide a Gail Risk Score. In this embodiment, the risk (i.e. combined 5-year Gail×SNP risk) score is provided by:

[Risk (i.e. Gail 5-year risk×SNP risk)]=[Gail 5-year risk]×$SNP_1$×$SNP_2$×$SNP_3$×$SNP_4$×$SNP_5$×$SNP_6$× $SNP_7$,×$SNP_8$. . . . ×$SNP_{72}$ etc.

In an embodiment, the risk [Gail 5-year risk×SNP risk] is used to determine whether estrogen receptor therapy should be offered to a subject to reduce the subjects risk. In this embodiment, the threshold level of risk is preferably (GAIL index>1.66% for 5-year risk).

In another embodiment, the risk score is determined by combined Gail lifetime risk×SNP risk provided by:

[Risk (i.e. Gail lifetime risk×SNP risk)]=[Gail lifetime risk]×$SNP_1$×$SNP_2$×$SNP_3$×$SNP_4$×$SNP_5$× $SNP_6$×$SNP_7$,$SNP_8$. . . . ×$SNP_{72}$ etc.

In a further embodiment, the risk [Gail lifetime risk×SNP risk] is used to determine whether a subject should be enrolled screening breast MRI and mammography program. In this embodiment, the threshold level is preferably greater than about (20% lifetime risk).

In an embodiment the methods of the present disclosure comprise combining the clinical risk assessment with the genetic risk assessment to obtain the risk of a human female subject for developing breast cancer.

It is envisaged that the "risk" of a human female subject for developing breast cancer can be provided as a relative risk (or risk ratio) or an absolute risk as required.

In an embodiment, the clinical risk assessment is combined with the genetic risk assessment to obtain the "relative risk" of a human female subject for developing breast cancer. Relative risk (or risk ratio), measured as the incidence of a disease in individuals with a particular characteristic (or exposure) divided by the incidence of the disease in individuals without the characteristic, indicates whether that particular exposure increases or decreases risk. Relative risk is helpful to identify characteristics that are associated with a disease, but by itself is not particularly helpful in guiding screening decisions because the frequency of the risk (incidence) is cancelled out.

In another embodiment, the clinical risk assessment is combined with the genetic risk assessment to obtain the "absolute risk" of a human female subject for developing breast cancer. Absolute risk is the numerical probability of a human female subject developing breast cancer within a specified period (e.g. 5, 10, 15, 20 or more years). It reflects a human female subjects risk of developing breast cancer in so far as it does not consider various risk factors in isolation.

Treatment

After performing the methods of the present disclosure treatment may be prescribed or administered to the subject.

One of skill in the art will appreciate that breast cancer is a heterogeneous disease with distinct clinical outcomes (Sorlie et al., 2001). For example, it is discussed in the art that breast cancer may be estrogen receptor positive or estrogen receptor negative.

In one embodiment, it is not envisaged that the methods of the present disclosure be limited to assessing the risk of developing a particular type or subtype of breast cancer. For example, it is envisaged that the methods of the present disclosure can be used to assess the risk of developing estrogen receptor positive or estrogen receptor negative breast cancer.

In another embodiment, the methods of the present disclosure are used to assess the risk of developing estrogen receptor positive breast cancer.

In another embodiment, the methods of the present disclosure are used to assess the risk of developing estrogen receptor negative breast cancer.

In another embodiment, the methods of the present disclosure are used to assess the risk of developing metastatic breast cancer.

In an example, a therapy that inhibits oestrogen is prescribed or administered to the subject.

In another example, a chemopreventative is prescribed or administered to the subject.

There are two main classes of drugs currently utilized for breast cancer chemoprevention:
(1) Selective Estrogen Receptor Modulators (SERMs) which block estrogen molecules from binding to their associated cellular receptor. This class of drugs includes for example Tamoxifen and Raloxifene.
(2) Aromatase Inhibitors which inhibit the conversion of androgens into estrogens by the aromatase enzyme 1e reducing the production of estrogens.
This class of drugs includes for example Exemestane, Letrozole, Anastrozole, Vorozole, Formestane, Fadrozole.

In an example, a SERM or an aromatase inhibitor is prescribed or administered to the subject.

In an example, Tamoxiln, Raloxifene, Exemestane, Letrozole, Anastrozole, Vorozole, Formestane or Fadrozole is prescribed or administered to a subject.

In an embodiment, the methods of the present disclosure are used to assess the risk of a human female subject for developing breast cancer and administering a treatment appropriate for the risk of developing breast cancer. For example, when performing the methods of the present disclosure indicates a high risk of breast cancer an aggressive chemopreventative treatment regimen can be established. In contrast, when performing the methods of the present disclosure indicates a moderate risk of breast cancer a less aggressive chemopreventative treatment regimen can be established. Alternatively, when performing the methods of the present disclosure indicates a low risk of breast cancer a chemopreventative treatment regimen need not be established. It is envisaged that the methods of the present disclosure can be performed over time so that the treatment regimen can be modified in accordance with the subjects risk of developing breast cancer.

Marker Detection Strategies

Amplification primers for amplifying markers (e.g., marker loci) and suitable probes to detect such markers or to genotype a sample with respect to multiple marker alleles, can be used in the disclosure. For example, primer selection for long-range PCR is described in U.S. Ser. No. 10/042,406 and U.S. Ser. No. 10/236,480; for short-range PCR, U.S. Ser. No. 10/341,832 provides guidance with respect to primer selection. Also, there are publicly available programs such as "Oligo" available for primer design. With such available primer selection and design software, the publicly available human genome sequence and the polymorphism locations, one of skill can construct primers to amplify the SNPs to practice the disclosure. Further, it will be appreciated that the precise probe to be used for detection of a nucleic acid comprising a SNP (e.g., an amplicon comprising the SNP) can vary. e.g., any probe that can identify the region of a marker amplicon to be detected can be used in conjunction with the present disclosure. Further, the configuration of the detection probes can, of course, vary. Thus, the disclosure is not limited to the sequences recited herein.

Indeed, it will be appreciated that amplification is not a requirement for marker detection, for example one can directly detect unamplified genomic DNA simply by performing a Southern blot on a sample of genomic DNA.

Typically, molecular markers are detected by any established method available in the art, including, without limitation, allele specific hybridization (ASH), detection of single nucleotide extension, array hybridization (optionally including ASH), or other methods for detecting single nucleotide polymorphisms (SNPs), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, and single-strand conformation polymorphisms (SSCP) detection.

Examples of oligonucleotide primers useful for amplifying nucleic acids comprising SNPs associated with breast cancer are provided in Table 5. As the skilled person will appreciate, the sequence of the genomic region to which these oligonucleotides hybridize can be used to design primers which are longer at the 5' and/or 3' end, possibly shorter at the 5' and/or 3' (as long as the truncated version can still be used for amplification), which have one or a few nucleotide differences (but nonetheless can still be used for amplification), or which share no sequence similarity with those provided but which are designed based on genomic sequences close to where the specifically provided oligonucleotides hybridize and which can still be used for amplification.

TABLE 5

Examples of oligonucleotide primers useful for the disclosure.

| Name | Sequence |
| --- | --- |
| rs889312_for | TATGGGAAGGAGTCGTTGAG (SEQ ID NO: 1) |
| rs6504950_for | CTGAATCACTCCTTGCCAAC (SEQ ID NO: 2) |
| rs4973768_for | CAAAATGATCTGACTACTCC (SEQ ID NO: 3) |
| rs4415084_for | TGACCAGTGCTGTATGTATC (SEQ ID NO: 4) |
| rs3817198_for | TCTCACCTGATACCAGATTC (SEQ ID NO: 5) |
| rs3803662_for | TCTCTCCTTAATGCCTCTAT (SEQ ID NO: 6) |
| rs2981582_for | ACTGCTGCGGGTTCCTAAAG (SEQ ID NO: 7) |

TABLE 5 -continued

Examples of oligonucleotide primers useful for the disclosure.

| Name | Sequence |
| --- | --- |
| rs13387042_for | GGAAGATTCGATTCAACAAGG (SEQ ID NO: 8) |
| rs13281615_for | GGTAACTATGAATCTCATC (SEQ ID NO: 9) |
| rs11249433_for | AAAAAGCAGAGAAAGCAGGG (SEQ ID NO: 10) |
| rs889312_rev | AGATGATCTCTGAGATGCCC (SEQ ID NO: 11) |
| rs6504950_rev | CCAGGGTTTGTCTACCAAAG (SEQ ID NO: 12) |
| rs4973768_rev | AATCACTTAAAACAAGCAG (SEQ ID NO: 13) |
| rs4415084_rev | CACATACCTCTACCTCTAGC (SEQ ID NO: 14) |
| rs3817198_rev | TTCCCTAGTGGAGCAGTGG (SEQ ID NO: 15) |
| rs3803662_rev | CTTTCTTCGCAAATGGGTGG (SEQ ID NO: 16) |
| rs2981582_rev | GCACTCATCGCCACTTAATG (SEQ ID NO: 17) |
| rs13387042_rev | GAACAGCTAAACCAGAACAG (SEQ ID NO: 18) |
| rs13281615_rev | ATCACTCTTATTTCTCCCCC (SEQ ID NO: 19) |
| rs11249433_rev | TGAGTCACTGTGCTAAGGAG (SEQ ID NO: 20) |

In some embodiments, the primers of the disclosure are radiolabelled, or labelled by any suitable means (e.g., using a non-radioactive fluorescent tag), to allow for rapid visualization of differently sized amplicons following an amplification reaction without any additional labelling step or visualization step. In some embodiments, the primers are not labelled, and the amplicons are visualized following their size resolution, e.g., following agarose or acrylamide gel electrophoresis. In some embodiments, ethidium bromide staining of the PCR amplicons following size resolution allows visualization of the different size amplicons.

It is not intended that the primers of the disclosure be limited to generating an amplicon of any particular size. For example, the primers used to amplify the marker loci and alleles herein are not limited to amplifying the entire region of the relevant locus, or any subregion thereof. The primers can generate an amplicon of any suitable length for detection. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Amplicons of any size can be detected using the various technologies described herein. Differences in base composition or size can be detected by conventional methods such as electrophoresis.

Some techniques for detecting genetic markers utilize hybridization of a probe nucleic acid to nucleic acids corresponding to the genetic marker (e.g., amplified nucleic acids produced using genomic DNA as a template). Hybridization formats, including, but not limited to: solution phase, solid phase, mixed phase, or in situ hybridization assays are useful for allele detection. An extensive guide to the hybridization of nucleic acids is found in Tijssen (1993) Laboratory Techniques in Biochemistry and Molecular Biology—Hybridization with Nucleic Acid Probes Elsevier, New York, as well as in Sambrook et al. (supra).

PCR detection using dual-labelled fluorogenic oligonucleotide probes, commonly referred to as "TaqMan™" probes, can also be performed according to the present disclosure. These probes are composed of short (e.g., 20-25 base) oligodeoxynucleotides that are labelled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes). Further details regarding dual-label probe strategies can be found, e.g., in WO 92/02638.

Other similar methods include e.g. fluorescence resonance energy transfer between two adjacently hybridized probes, e.g., using the "LightCycler®" format described in U.S. Pat. No. 6,174,670.

Array-based detection can be performed using commercially available arrays. e.g., from Affymetrix (Santa Clara, Calif.) or other manufacturers. Reviews regarding the operation of nucleic acid arrays include Sapolsky et al. (1999); Lockhart (1998); Fodor (1997a): Fodor (1997b) and Chee et al. (1996). Array based detection is one preferred method for identification markers of the disclosure in samples, due to the inherently high-throughput nature of array based detection.

The nucleic acid sample to be analyzed is isolated, amplified and, typically, labelled with biotin and/or a fluorescent reporter group. The labelled nucleic acid sample is then incubated with the array using a fluidics station and hybridization oven. The array can be washed and or stained or counter-stained, as appropriate to the detection method. After hybridization, washing and staining, the array is inserted into a scanner, where patterns of hybridization are detected. The hybridization data are collected as light emitted from the fluorescent reporter groups already incorporated into the labelled nucleic acid, which is now bound to the probe array. Probes that most clearly match the labelled nucleic acid produce stronger signals than those that have mismatches. Since the sequence and position of each probe on the array are known, by complementarity, the identity of the nucleic acid sample applied to the probe array can be identified.

Correlating Markers to Phenotypes

These correlations can be performed by any method that can identify a relationship between an allele and a phenotype, or a combination of alleles and a combination of phenotypes. For example, alleles in genes or loci defined herein can be correlated with one or more breast cancer phenotypes. Most typically, these methods involve referencing a look up table that comprises correlations between alleles of the polymorphism and the phenotype. The table can include data for multiple allele-phenotype relationships and can take account of additive or other higher order effects of multiple allele-phenotype relationships. e.g., through the use of statistical tools such as principle component analysis, heuristic algorithms, etc.

Correlation of a marker to a phenotype optionally includes performing one or more statistical tests for correlation. Many statistical tests are known, and most are computer-implemented for ease of analysis. A variety of statistical methods of determining associations/correlations between phenotypic traits and biological markers are known and can be applied to the present disclosure. Hartl (1981) A Primer of Population Genetics Washington University. Saint Louis Sinauer Associates. Inc. Sunderland, Mass. ISBN: 0-087893-271-2. A variety of appropriate statistical models are described in Lynch and Walsh (1998) Genetics and Analysis of Quantitative Traits. Sinauer Associates. Inc. Sunderland Mass. ISBN 0-87893-481-2. These models can, for example, provide for correlations between genotypic and phenotypic values, characterize the influence of a locus on a phenotype, sort out the relationship between environment and genotype, determine dominance or penetrance of genes, determine maternal and other epigenetic effects, determine principle components in an analysis (via principle component analysis, or "PCA"), and the like. The references cited in these texts provides considerable further detail on statistical models for correlating markers and phenotype.

In addition to standard statistical methods for determining correlation, other methods that determine correlations by pattern recognition and training, such as the use of genetic algorithms, can be used to determine correlations between markers and phenotypes. This is particularly useful when identifying higher order correlations between multiple alleles and multiple phenotypes. To illustrate, neural network approaches can be coupled to genetic algorithm-type programming for heuristic development of a structure-function data space model that determines correlations between genetic information and phenotypic outcomes.

In any case, essentially any statistical test can be applied in a computer implemented model, by standard programming methods, or using any of a variety of "off the shelf" software packages that perform such statistical analyses, including, for example, those noted above and those that are commercially available, e.g., from Partek Incorporated (St. Peters, Mo.: www.partek.com). e.g., that provide software for pattern recognition (e.g., which provide Partek Pro 2000 Pattern Recognition Software).

Additional details regarding association studies can be found in U.S. Ser. No. 10/106,097, U.S. Ser. No. 10/042, 819, U.S. Ser. No. 10/286,417, U.S. Ser. No. 10/768,788, U.S. Ser. No. 10/447,685, U.S. Ser. No. 10/970,761, and U.S. Pat. No. 7,127,355.

Systems for performing the above correlations are also a feature of the disclosure. Typically, the system will include system instructions that correlate the presence or absence of an allele (whether detected directly or, e.g., through expression levels) with a predicted phenotype.

Optionally, the system instructions can also include software that accepts diagnostic information associated with any detected allele information, e.g., a diagnosis that a subject with the relevant allele has a particular phenotype. This software can be heuristic in nature, using such inputted associations to improve the accuracy of the look up tables and/or interpretation of the look up tables by the system. A variety of such approaches, including neural networks. Marko, modelling, and other statistical analysis are described above.

Polymorphic Profiling

The disclosure provides methods of determining the polymorphic profile of an individual at the SNPs outlined in the present disclosure (Table 6) or SNPs in linkage disequilibrium with one or more thereof.

The polymorphic profile constitutes the polymorphic forms occupying the various polymorphic sites in an individual. In a diploid genome, two polymorphic forms, the same or different from each other, usually occupy each polymorphic site. Thus, the polymorphic profile at sites X and Y can be represented in the form X (x1, x1), and Y (y1, y2), wherein x1, x1 represents two copies of allele x1 occupying site X and y1, y2 represent heterozygous alleles occupying site Y.

The polymorphic profile of an individual can be scored by comparison with the polymorphic forms associated with resistance or susceptibility to breast cancer occurring at each site. The comparison can be performed on at least. e.g., 1, 2, 5, 10, 25, 50, or all of the polymorphic sites, and optionally, others in linkage disequilibrium with them. The polymorphic sites can be analyzed in combination with other polymorphic sites.

Polymorphic profiling is useful, for example, in selecting agents to affect treatment or prophylaxis of breast cancer in a given individual. Individuals having similar polymorphic profiles are likely to respond to agents in a similar way.

Polymorphic profiling is also useful for stratifying individuals in clinical trials of agents being tested for capacity to treat breast cancer or related conditions. Such trials are performed on treated or control populations having similar or identical polymorphic profiles (see EP 99965095.5), for example, a polymorphic profile indicating an individual has an increased risk of developing breast cancer. Use of genetically matched populations eliminates or reduces variation in treatment outcome due to genetic factors, leading to a more accurate assessment of the efficacy of a potential drug.

Polymorphic profiling is also useful for excluding individuals with no predisposition to breast cancer from clinical trials. Including such individuals in the trial increases the size of the population needed to achieve a statistically significant result. Individuals with no predisposition to breast cancer can be identified by determining the numbers of resistances and susceptibility alleles in a polymorphic profile as described above. For example, if a subject is genotyped at ten sites in ten genes of the disclosure associated with breast cancer, twenty alleles are determined in total. If over 50% and alternatively over 60% or 75% percent of these are resistance genes, the individual is unlikely to develop breast cancer and can be excluded from the trial.

In other embodiments, stratifying individuals in clinical trials may be accomplished using polymorphic profiling in combination with other stratification methods, including, but not limited to, family history, risk models (e.g., Gail Score, Claus model), clinical phenotypes (e.g., atypical lesions, breast density), and specific candidate biomarkers.

Computer Implemented Method

It is envisaged that the methods of the present disclosure may be implemented by a system such as a computer implemented method. For example, the system may be a computer system comprising one or a plurality of processors which may operate together (referred to for convenience as "processor") connected to a memory. The memory may be a non-transitory computer readable medium, such as a hard drive, a solid state disk or CD-ROM. Software, that is executable instructions or program code, such as program code grouped into code modules, may be stored on the memory, and may, when executed by the processor, cause the computer system to perform functions such as determining that a task is to be performed to assist a user to determine the risk of a human female subject for developing breast cancer; receiving data indicating the clinical risk and genetic risk of the female subject developing breast cancer, wherein the genetic risk was derived by detecting, in a biological sample derived from the female subject, at least 72 single nucleotide polymorphisms associated with breast cancer, wherein at least 67 of the single nucleotide polymorphisms are selected from Table 7, or a single nucleotide polymorphism in linkage disequilibrium with one or more thereof and the remaining single nucleotide polymorphisms are selected from Table 6, or a single nucleotide polymorphism in linkage disequilibrium with one or more thereof: processing the data to combine the clinical risk with the genetic risk assessment to obtain the risk of a human female subject for developing breast cancer; outputting the risk of a human female subject for developing breast cancer.

For example, the memory may comprise program code which when executed by the processor causes the system to determine at least 72 single nucleotide polymorphisms associated with breast cancer, wherein at least 67 of the single nucleotide polymorphisms are selected from Table 7, or a single nucleotide polymorphism in linkage disequilibrium with one or more thereof and the remaining single nucleotide polymorphisms are selected from Table 6, or a single nucleotide polymorphism in linkage disequilibrium with one or more thereof, or receive data indicating at least 72 single nucleotide polymorphisms associated with breast cancer, wherein at least 67 of the single nucleotide polymorphisms are selected from Table 7, or a single nucleotide polymorphism in linkage disequilibrium with one or more thereof and the remaining single nucleotide polymorphisms are selected from Table 6, or a single nucleotide polymorphism in linkage disequilibrium with one or more thereof; process the data to combine the clinical risk with the genetic risk assessment to obtain the risk of a human female subject for developing breast cancer; report the risk of a human female subject for developing breast cancer.

In another embodiment, the system may be coupled to a user interface to enable the system to receive information from a user and/or to output or display information. For example, the user interface may comprise a graphical user interface, a voice user interface or a touchscreen.

In an embodiment, the program code may causes the system to determine the "SNP risk".

In an embodiment, the program code may causes the system to determine Combined Clinical assessment×Genetic Risk (for example SNP risk).

In an embodiment, the system may be configured to communicate with at least one remote device or server across a communications network such as a wireless communications network. For example, the system may be configured to receive information from the device or server across the communications network and to transmit information to the same or a different device or server across the communications network. In other embodiments, the system may be isolated from direct user interaction.

In another embodiment, performing the methods of the present disclosure to assess the risk of a human female subject for developing breast cancer, enables establishment of a diagnostic or prognostic rule based on the the clinical risk and genetic risk of the female subject developing breast cancer. For example, the diagnostic or prognostic rule can be based on the Combined Clinical assessment×SNP Risk Score relative to a control, standard or threshold level of risk.

In an embodiment, the threshold level of risk is the level recommended by the American Cancer Society (ACS) guidelines for screening breast MRI and mammography. In this example, the threshold level is preferably greater than about (20% lifetime risk).

In another embodiment, the threshold level of risk is the level recommended American Society of Clinical Oncology (ASCO) for offering an estrogen receptor therapy to reduce a subjects risk. In this embodiment, the threshold level of risk is preferably (GAIL index>1.66% for 5-year risk).

In another embodiment, the diagnostic or prognostic rule is based on the application of a statistical and machine learning algorithm. Such an algorithm uses relationships between a population of SNPs and disease status observed in training data (with known disease status) to infer relationships which are then used to determine the risk of a human female subject for developing breast cancer in subjects with an unknown risk. An algorithm is employed which provides an risk of a human female subject developing breast cancer. The algorithm performs a multivariate or univariate analysis function.

Kits and Products

In an embodiment, the present invention provides a kit comprising at least 72 sets of primers for amplifying 72 or more nucleic acids, wherein the 72 or more nucleic acids comprise a single nucleotide polymorphism selected from Table 6, or a single nucleotide polymorphism in linkage disequilibrium with one or more thereof.

In an embodiment, at least 67, at least 68, at least 69, at least 70 sets of the primers amplify nucleic acids comprising a single nucleotide polymorphism selected from Table 7, or a single nucleotide polymorphism in linkage disequilibrium thereof.

Examples of primers suitable for a kit of the invention are provided in Fable 5.

However, as would be appreciated by those of skill in the an, once a SNP is identified, primers can be designed to amplify the SNP as a matter of routine. Various software programs are freely available that can suggest suitable primers for amplifying SNPs of interest.

Again, it would be known to those of skill in the art that PCR primers of a PCR primer pair can be designed to specifically amplify a region of interest from human DNA. In the context of the present disclosure, the region of interest contains the single-base variation (e.g. single-nucleotide polymorphism, SNP) which shall be genotyped.

Each PCR primer of a PCR primer pair can be placed adjacent to a particular single-base variation on opposing sites of the DNA sequence variation. Furthermore, PCR primers can been designed to avoid any known DNA sequence variation and repetitive DNA sequences in their PCR primer binding sites.

The kit may further comprise other reagents required to perform an amplification reaction such as a buffer, nucleotides and/or a polymerase, as well as reagents for extracting nucleic acids from a sample.

Array based detection is one preferred method for assessing the SNPs of the disclosure in samples, due to the inherently high-throughput nature of array based detection.

A variety of probe arrays have been described in the literature and can be used in the context of the present disclosure for detection of SNPs that can be correlated to breast cancer. For example, DNA probe array chips are used in one embodiment of the disclosure. The recognition of sample DNA by the set of DNA probes takes place through DNA hybridization. When a DNA sample hybridizes with an array of DNA probes, the sample binds to those probes that are complementary to the sample DNA sequence. By evaluating to which probes the sample DNA for an individual hybridizes more strongly, it is possible to determine whether a known sequence of nucleic acid is present or not in the sample, thereby determining whether a marker found in the nucleic acid is present.

In an embodiment, the present invention provides a genetic array comprising at least 72 sets of probes for hybridising to 72 or more nucleic acids, wherein the 72 or more nucleic acids comprise a single nucleotide polymorphism selected from Table 6, or a single nucleotide polymorphism in linkage disequilibrium with one or more thereof.

In an embodiment, at least 67, at least 68, at least 69, at least 70 sets of the probes hybridise to nucleic acids comprising a single nucleotide polymorphism selected from Table 7, or a single nucleotide polymorphism in linkage disequilibrium thereof.

EXAMPLES

Example 1—SNPs Indicative of Breast Cancer Risk

SNPs indicative of breast cancer risk are shown in Table 6. 88 SNPs have been identified in total. 77 SNPs are informative in Caucasians. 78 SNPs are informative in African Americans and 82 are informative in Hispanics. 70 SNPs are informative in Caucasians, African Americans and Hispanics (indicated by horizontal stripe pattern; see also Table 7). The remaining 18 SNPs (see Table 8) are informative in either Caucasians (indicated by dark trellis pattern; see also Table 9), African Americans (indicated by downward diagonal stripe pattern: see also Table 10) and/or Hispanics (indicated by light grid pattern: see also Table 11).

TABLE 9

Caucasian SNPs (n = 77). Alleles represented as major/minor (eg for rs616488 A is the common allele and G less common). OR minor allele numbers below 1 means the minor allele is not the risk allele, whereas when above 1 the minor allele is the risk allele.

| SNP | Chromosome | Alleles | Minor allele frequency | OR Minor Allele | μ | Adjusted Risk Score | | |
|---|---|---|---|---|---|---|---|---|
| rs616488 | 1 | A/G | 0.33 | 0.9417 | 0.96 | AA 1.04 | GA 0.98 | GG 0.92 |
| rs11552449 | 1 | C/T | 0.17 | 1.0810 | 1.03 | CC 0.97 | TC 1.05 | TT 1.14 |
| rs11249433 | 1 | A/G | 0.40 | 1.0993 | 1.08 | AA 0.93 | GA 1.02 | GG 1.12 |
| rs6678914 | 1 | G/A | 0.414 | 0.9890 | 0.99 | GG 1.01 | AG 1.00 | AA 0.99 |

TABLE 9-continued

Caucasian SNPs (n = 77). Alleles represented as major/minor (eg for rs616488 A is the common allele and G less common). OR minor allele numbers below 1 means the minor allele is not the risk allele, whereas when above 1 the minor allele is the risk allele.

| SNP | Chromosome | Alleles | Minor allele frequency | OR Minor Allele | μ | Adjusted Risk Score | | |
|---|---|---|---|---|---|---|---|---|
| rs4245739 | 1 | A/C | 0.258 | 1.0291 | 1.02 | AA 0.99 | CA 1.01 | CC 1.04 |
| rs12710696 | 2 | G/A | 0.357 | 1.0387 | 1.03 | GG 0.97 | AG 1.01 | AA 1.05 |
| rs4849887 | 2 | C/T | 0.098 | 0.9187 | 0.98 | CC 1.02 | TC 0.93 | TT 0.86 |
| rs2016394 | 2 | G/A | 0.48 | 0.9504 | 0.95 | GG 1.05 | AG 1.00 | AA 0.95 |
| rs1550623 | 2 | A/G | 0.16 | 0.9445 | 0.98 | AA 1.02 | GA 0.96 | GG 0.91 |
| rs1045485 | 2 | G/C | 0.13 | 0.9644 | 0.99 | GG 1.01 | CG 0.97 | CC 0.94 |
| rs13387042 | 2 | A/G | 0.49 | 0.8794 | 0.89 | AA 1.13 | GA 0.99 | GG 0.87 |
| rs16857609 | 2 | C/T | 0.26 | 1.0721 | 1.04 | CC 0.96 | TC 1.03 | TT 1.11 |
| rs6762644 | 3 | A/G | 0.4 | 1.0661 | 1.04 | AA 0.95 | GA 1.01 | GG 1.08 |
| rs4973768 | 3 | C/T | 0.47 | 1.0938 | 1.09 | CC 0.92 | TC 1.00 | TT 1.10 |
| rs12493607 | 3 | G/C | 0.35 | 1.0529 | 1.04 | GG 0.96 | CG 1.01 | CC 1.07 |
| rs7696175 | 4 | | | | | | | |
| rs9790517 | 4 | C/T | 0.23 | 1.0481 | 1.02 | CC 0.98 | TC 1.03 | TT 1.07 |
| rs6828523 | 4 | C/A | 0.13 | 0.9056 | 0.98 | CC 1.03 | AC 0.93 | AA 0.84 |
| rs4415084 | 5 | | | | | | | |
| rs10069690 | 5 | C/T | 0.26 | 1.0242 | 1.01 | CC 0.99 | TC 1.01 | TT 1.04 |
| rs7726159 | 5 | C/A | 0.338 | 1.0359 | 1.02 | CC 0.98 | AC 1.01 | AA 1.05 |
| rs2736108 | 5 | C/T | 0.292 | 0.9379 | 0.96 | CC 1.04 | TC 0.97 | TT 0.91 |
| rs10941679 | 5 | A/G | 0.25 | 1.1198 | 1.06 | AA 0.94 | GA 1.06 | GG 1.18 |
| rs889312 | 5 | A/C | 0.28 | 1.1176 | 1.07 | AA 0.94 | CA 1.05 | CC 1.17 |
| rs10472076 | 5 | T/C | 0.38 | 1.0419 | 1.03 | TT 0.97 | CT 1.01 | CC 1.05 |
| rs2067980 | 5 | | | | | | | |
| rs1353747 | 5 | T/G | 0.095 | 0.9213 | 0.99 | TT 1.02 | GT 0.94 | GG 0.86 |
| rs1432679 | 5 | A/G | 0.43 | 1.0670 | 1.06 | AA 0.94 | GA 1.01 | GG 1.08 |
| rs11242675 | 6 | T/C | 0.39 | 0.9429 | 0.96 | TT 1.05 | CT 0.99 | CC 0.93 |
| rs204247 | 6 | A/G | 0.43 | 1.0503 | 1.04 | AA 0.96 | GA 1.01 | GG 1.06 |
| rs17529111 | 6 | A/G | 0.218 | 1.0457 | 1.02 | AA 0.98 | GA 1.03 | GG 1.07 |
| rs2180341 | 6 | | | | | | | |
| rs9485370 | 6 | | | | | | | |
| rs12662670 | 6 | T/G | 0.073 | 1.1392 | 1.02 | TT 0.98 | GT 1.12 | GG 1.27 |
| rs3757318 | 6 | | | | | | | |
| rs2046210 | 6 | G/A | 0.34 | 1.0471 | 1.03 | GG 0.97 | AG 1.01 | AA 1.06 |
| rs17157903 | 7 | | | | | | | |
| rs720475 | 7 | G/A | 0.25 | 0.9452 | 0.97 | GG 1.03 | AG 0.97 | AA 0.92 |
| rs9693444 | 8 | C/A | 0.32 | 1.0730 | 1.05 | CC 0.95 | AC 1.02 | AA 1.10 |
| rs6472903 | 8 | T/G | 0.18 | 0.9124 | 0.97 | TT 1.03 | GT 0.94 | GG 0.86 |
| rs2943559 | 8 | A/G | 0.07 | 1.1334 | 1.02 | AA 0.98 | GA 1.11 | GG 1.26 |
| rs13281615 | 8 | A/G | 0.41 | 1.0950 | 1.08 | AA 0.93 | GA 1.01 | GG 1.11 |
| rs11780156 | 8 | C/T | 0.16 | 1.0691 | 1.02 | CC 0.98 | TC 1.05 | TT 1.12 |
| rs1011970 | 9 | G/T | 0.17 | 1.0502 | 1.02 | GG 0.98 | TG 1.03 | TT 1.08 |
| rs10759243 | 9 | C/A | 0.39 | 1.0542 | 1.04 | CC 0.96 | AC 1.01 | AA 1.07 |
| rs865686 | 9 | T/G | 0.38 | 0.8985 | 0.92 | TT 1.08 | GT 0.97 | GG 0.87 |
| rs2380205 | 10 | C/T | 0.44 | 0.9771 | 0.98 | CC 1.02 | TC 1.00 | TT 0.97 |
| rs7072776 | 10 | G/A | 0.29 | 1.0581 | 1.03 | GG 0.97 | AG 1.02 | AA 1.08 |
| rs11814448 | 10 | A/C | 0.02 | 1.2180 | 1.01 | AA 0.99 | CA 1.21 | CC 1.47 |
| rs10822013 | 10 | | | | | | | |
| rs10995190 | 10 | G/A | 0.16 | 0.8563 | 0.95 | GG 1.05 | AG 0.90 | AA 0.77 |
| rs704010 | 10 | C/T | 0.38 | 1.06991 | .05 | CC 0.95 | TC 1.02 | TT 1.09 |
| rs7904519 | 10 | A/G | 0.46 | 1.0584 | 1.05 | AA 0.95 | GA 1.00 | GG 1.06 |
| rs2981579 | 10 | G/A | 0.4 | 1.2524 | 1.21 | GG 0.83 | AG 1.03 | AA 1.29 |
| rs2981582 | 10 | | | | | | | |
| rs11199914 | 10 | C/T | 0.32 | 0.9400 | 0.96 | CC 1.04 | TC 0.98 | TT 0.92 |
| rs3817198 | 11 | T/C | 0.31 | 1.0744 | 1.05 | TT 0.96 | CT 1.03 | CC 1.10 |
| rs3903072 | 11 | G/T | 0.47 | 0.9442 | 0.95 | GG 1.05 | TG 1.00 | TT 0.94 |
| rs554219 | 11 | C/G | 0.112 | 1.1238 | 1.03 | CC 0.97 | GC 1.09 | GG 1.23 |
| rs614367 | 11 | | | | | | | |
| rs78540526 | 11 | C/T | 0.032 | 1.1761 | 1.01 | CC 0.99 | TC 1.16 | TT 1.37 |
| rs75915166 | 11 | C/A | 0.059 | 1.0239 | 1.00 | CC 1.00 | AC 1.02 | AA 1.05 |
| rs11820646 | 11 | C/T | 0.41 | 0.9563 | 0.96 | CC 1.04 | TC 0.99 | TT 0.95 |
| rs12422552 | 12 | G/C | 0.26 | 1.0327 | 1.02 | GG 0.98 | CG 1.02 | CC 1.05 |
| rs10771399 | 12 | A/G | 0.12 | 0.8629 | 0.97 | AA 1.03 | GA 0.89 | GG 0.77 |
| rs17356907 | 12 | A/G | 0.3 | 0.9078 | 0.95 | AA 1.06 | GA 0.96 | GG 0.87 |
| rs1292011 | 12 | A/G | 0.42 | 0.9219 | 0.94 | AA 1.07 | GA 0.99 | GG 0.91 |
| rs11571833 | 13 | A/T | 0.008 | 1.2609 | 1.00 | AA 1.00 | TA 1.26 | TT 1.58 |
| rs2236007 | 14 | G/A | 0.21 | 0.9203 | 0.97 | GG 1.03 | AG 0.95 | AA 0.88 |
| rs999737 | 14 | C/T | 0.23 | 0.9239 | 0.97 | CC 1.04 | TC 0.96 | TT 0.88 |
| rs2588809 | 14 | C/T | 0.16 | 1.0667 | 1.02 | CC 0.98 | TC 1.04 | TT 1.11 |
| rs941764 | 14 | A/G | 0.34 | 1.0636 | 1.04 | AA 0.96 | GA 1.02 | GG 1.08 |
| rs3803662 | 16 | G/A | 0.26 | 1.2257 | 1.12 | GG 0.89 | AG 1.09 | AA 1.34 |
| rs17817449 | 16 | T/G | 0.4 | 0.9300 | 0.94 | TT 1.06 | GT 0.98 | GG 0.92 |
| rs11075995 | 16 | A/T | 0.241 | 1.0368 | 1.02 | AA 0.98 | TA 1.02 | TT 1.06 |
| rs13329835 | 16 | A/G | 0.22 | 1.0758 | 1.03 | AA 0.97 | GA 1.04 | GG 1.12 |

TABLE 9-continued

Caucasian SNPs (n = 77). Alleles represented as major/minor (eg for rs616488 A is the common allele and G less common). OR minor allele numbers below 1 means the minor allele is not the risk allele, whereas when above 1 the minor allele is the risk allele.

| SNP | Chromosome | Alleles | Minor allele frequency | OR Minor Allele | μ | Adjusted Risk Score | | |
|---|---|---|---|---|---|---|---|---|
| rs6504950 | 17 | G/A | 0.28 | 0.9340 | 0.96 | GG 1.04 | AG 0.97 | AA 0.91 |
| rs527616 | 18 | G/C | 0.38 | 0.9573 | 0.97 | GG 1.03 | CG 0.99 | CC 0.95 |
| rs1436904 | 18 | T/G | 0.4 | 0.9466 | 0.96 | TT 1.04 | GT 0.99 | GG 0.94 |
| rs2363956 | 19 | G/T | 0.487 | 1.0264 | 1.03 | GG 0.97 | TG 1.00 | TT 1.03 |
| rs8170 | 19 | G/A | 0.19 | 1.0314 | 1.01 | GG 0.99 | AG 1.02 | AA 1.05 |
| rs4808801 | 19 | A/G | 035 | 0.9349 | 0.95 | AA 1.05 | GA 0.98 | GG 0.92 |
| rs3760982 | 19 | G/A | 0.46 | 1.0553 | 1.05 | GG 0.95 | AG 1.00 | AA 1.06 |
| rs2284378 | 20 | | | | | | | |
| rs2823093 | 21 | G/A | 0.27 | 0.9274 | 0.96 | GG 1.04 | AG 0.96 | AA 0.89 |
| rs17879961 | 22 | A/G | 0.005 | 1.3632 | 1.00 | AA 1.00 | GA 1.36 | GG 1.85 |
| rs132390 | 22 | T/C | 0.036 | 1.1091 | 1.01 | TT 0.99 | CT 1.10 | CC 1.22 |
| rs6001930 | 22 | T/C | 0.11 | 1.1345 | 1.03 | TT 0.97 | CT 1.10 | CC 1.25 |

TABLE 10

African American SNPs (n = 78). Alleles represented as risk/reference (non-risk) (eg for rs616488 A is the risk allele).

| SNP | Chromosome | Alleles | Risk allele frequency | OR Risk Allele | μ | Adjusted Risk Score | | |
|---|---|---|---|---|---|---|---|---|
| rs616488 | 1 | A/G | 0.86 | 1.03 | 1.05 | AA 0.95 | AG 0.98 | GG 1.01 |
| rs11552449 | 1 | C/T | 0.037 | 0.9 | 0.99 | CC 1.01 | CT 0.91 | TT 0.82 |
| rs11249433 | 1 | A/G | 0.13 | 0.99 | 1.00 | AA 1.00 | AG 0.99 | GG 0.98 |
| rs6678914 | 1 | G/A | 0.66 | 1 | 1.00 | GG 1.00 | GA 1.00 | AA 1.00 |
| rs4245739 | 1 | A/C | 0.24 | 0.97 | 0.99 | AA 1.01 | AC 0.98 | CC 0.95 |
| rs12710696 | 2 | G/A | 0.53 | 1.06 | 1.06 | GG 0.94 | GA 1.00 | AA 1.06 |
| rs4849887 | 2 | C/T | 0.7 | 1.16 | 1.24 | CC 0.81 | CT 0.94 | TT 1.09 |
| rs2016394 | 2 | G/A | 0.72 | 1.05 | 1.07 | GG 0.93 | GA 0.98 | AA 1.03 |
| rs1550623 | 2 | A/G | 0.71 | 1.1 | 1.15 | AA 0.87 | AG 0.96 | GG 1.05 |
| rs1045485 | 2 | G/C | 0.93 | 0.99 | 0.98 | GG 1.02 | GC 1.01 | CC 1.00 |
| rs13387042 | 2 | A/G | 0.72 | 1.12 | 1.18 | AA 0.85 | AG 0.95 | GG 1.06 |
| rs16857609 | 2 | C/T | 0.24 | 1.17 | 1.08 | CC 0.92 | CT 1.08 | TT 1.26 |
| rs6762644 | 3 | A/G | 0.46 | 1.05 | 1.05 | AA 0.96 | AG 1.00 | GG 1.05 |
| rs4973768 | 3 | C/T | 0.36 | 1.04 | 1.03 | CC 0.97 | CT 1.01 | TT 1.05 |
| rs12493607 | 3 | G/C | 0.14 | 1.04 | 1.01 | GG 0.99 | GC 1.03 | CC 1.07 |
| rs7696175 | 4 | | | | | | | |
| rs9790517 | 4 | C/T | 0.084 | 0.88 | 0.98 | CC 1.02 | CT 0.90 | TT 0.79 |
| rs6828523 | 4 | C/A | 0.65 | 1 | 1.00 | CC 1.00 | CA 1.00 | AA 1.00 |
| rs4415084 | 5 | C/T | 0.61 | 1.1 | 1.13 | CC 0.89 | CT 0.98 | TT 1.07 |
| rs10069690 | 5 | C/T | 0.57 | 1.13 | 1.15 | CC 0.87 | CT 0.98 | TT 1.11 |
| rs7726159 | 5 | | | | | | | |
| rs2736108 | 5 | | | | | | | |
| rs10941679 | 5 | A/G | 0.21 | 1.04 | 1.02 | AA 0.98 | AG 1.02 | GG 1.06 |
| rs889312 | 5 | A/C | 0.33 | 1.07 | 1.05 | AA 0.96 | AC 1.02 | CC 1.09 |
| rs10472076 | 5 | T/C | 0.28 | 0.95 | 0.97 | TT 1.03 | TC 0.98 | CC 0.93 |
| rs2067980 | 5 | | | | | | | |
| rs1353747 | 5 | T/G | 0.98 | 1.01 | 1.02 | TT 0.98 | TG 0.99 | GG 1.00 |
| rs1432679 | 5 | A/G | 0.79 | 1.07 | 1.11 | AA 0.90 | AG 0.96 | GG 1.03 |
| rs11242675 | 6 | T/C | 0.51 | 1.06 | 1.06 | TT 0.94 | TC 1.00 | CC 1.06 |
| rs204247 | 6 | A/G | 0.34 | 1.13 | 1.09 | AA 0.92 | AG 1.04 | GG 1.17 |
| rs17529111 | 6 | A/G | 0.075 | 0.99 | 1.00 | AA 1.00 | AG 0.99 | GG 0.98 |
| rs2180341 | 6 | | | | | | | |
| rs9485370 | 6 | G/T | 0.78 | 1.13 | 1.21 | GG 0.82 | GT 0.93 | TT 1.05 |
| rs12662670 | 6 | | | | | | | |
| rs3757318 | 6 | G/A | 0.038 | 1.11 | 1.01 | GG 0.99 | GA 1.10 | AA 1.22 |
| rs2046210 | 6 | G/A | 0.6 | 0.99 | 0.99 | GG 1.01 | GA 1.00 | AA 0.99 |
| rs17157903 | 7 | | | | | | | |
| rs720475 | 7 | G/A | 0.88 | 0.99 | 0.98 | GG 1.02 | GA 1.01 | AA 1.00 |
| rs9693444 | 8 | C/A | 0.37 | 1.06 | 1.04 | CC 0.96 | CA 1.01 | AA 1.08 |
| rs6472903 | 8 | T/G | 0.9 | 1.02 | 1.04 | TT 0.96 | TG 0.98 | GG 1.00 |
| rs2943559 | 8 | A/G | 0.22 | 1.07 | 1.03 | AA 0.97 | AG 1.04 | GG 1.11 |
| rs13281615 | 8 | A/G | 0.43 | 1.06 | 1.05 | AA 0.95 | AG 1.01 | GG 1.07 |
| rs11780156 | 8 | C/T | 0.052 | 0.84 | 0.98 | CC 1.02 | CT 0.85 | TT 0.72 |
| rs1011970 | 9 | G/T | 0.32 | 1.06 | 1.04 | GG 0.96 | GT 1.02 | TT 1.08 |
| rs10759243 | 9 | C/A | 0.59 | 1.02 | 1.02 | CC 0.98 | CA 1.00 | AA 1.02 |
| rs865686 | 9 | T/G | 0.51 | 1.09 | 1.09 | TT 0.91 | TG 1.00 | GG 1.09 |
| rs2380205 | 10 | C/T | 0.42 | 0.98 | 0.98 | CC 1.02 | CT 1.00 | TT 0.98 |

TABLE 10-continued

African American SNPs (n = 78). Alleles represented as risk/reference (non-risk) (eg for rs616488 A is the risk allele).

| SNP | Chromosome | Alleles | Risk allele frequency | OR Risk Allele | μ | Adjusted Risk Score | | |
|---|---|---|---|---|---|---|---|---|
| rs7072776 | 10 | G/A | 0.49 | 1.04 | 1.04 | GG 0.96 | GA 1.00 | AA 1.04 |
| rs11814448 | 10 | A/C | 0.61 | 1.04 | 1.05 | AA 0.95 | AC 0.99 | CC 1.03 |
| rs10822013 | 10 | T/C | 0.23 | 1 | 1.00 | TT 1.00 | TC 1.00 | CC 1.00 |
| rs10995190 | 10 | G/A | 0.83 | 0.98 | 0.97 | GG 1.03 | GA 1.01 | AA 0.99 |
| rs704010 | 10 | C/T | 0.11 | 0.98 | 1.00 | CC 1.00 | CT 0.98 | TT 0.96 |
| rs7904519 | 10 | A/G | 0.78 | 1.13 | 1.21 | AA 0.82 | AG 0.93 | GG 1.05 |
| rs2981579 | 10 | G/A | 0.59 | 1.18 | 1.22 | GG 0.82 | GA 0.96 | AA 1.14 |
| rs2981582 | 10 | G/A | 0.49 | 1.05 | 1.05 | GG 0.95 | GA 1.00 | AA 1.05 |
| rs11199914 | 10 | C/T | 0.48 | 0.97 | 0.97 | CC 1.03 | CT 1.00 | TT 0.97 |
| rs3817198 | 11 | T/C | 0.17 | 0.98 | 0.99 | TT 1.01 | TC 0.99 | CC 0.97 |
| rs3903072 | 11 | G/T | 0.82 | 0.99 | 0.98 | GG 1.02 | GT 1.01 | TT 1.00 |
| rs554219 | 11 | C/G | 0.22 | 1 | 1.00 | CC 1.00 | CG 1.00 | GG 1.00 |
| rs614367 | 11 | G/A | 0.13 | 0.96 | 0.99 | GG 1.01 | GA 0.97 | AA 0.93 |
| rs78540526 | 11 | | | | | | | |
| rs75915166 | 11 | C/A | 0.015 | 1.44 | 1.01 | CC 0.99 | CA 1.42 | AA 2.05 |
| rs11820646 | 11 | C/T | 0.78 | 0.98 | 0.97 | CC 1.03 | CT 1.01 | TT 0.99 |
| rs12422552 | 12 | G/C | 0.41 | 1.02 | 1.02 | GG 0.98 | GC 1.00 | CC 1.02 |
| rs10771399 | 12 | A/G | 0.96 | 1.19 | 1.40 | AA 0.72 | AG 0.85 | GG 1.01 |
| rs17356907 | 12 | A/G | 0.79 | 1.02 | 1.03 | AA 0.97 | AG 0.99 | GG 1.01 |
| rs1292011 | 12 | A/G | 0.55 | 1.03 | 1.03 | AA 0.97 | AG 1.00 | GG 1.03 |
| rs11571833 | 13 | A/T | 0.003 | 0.95 | 1.00 | AA 1.00 | AT 0.95 | TT 0.90 |
| rs2236007 | 14 | G/A | 0.93 | 0.9 | 0.82 | GG 1.22 | GA 1.09 | AA 0.98 |
| rs999737 | 14 | C/T | 0.95 | 1.03 | 1.06 | CC 0.95 | CT 0.97 | TT 1.00 |
| rs2588809 | 14 | C/T | 0.29 | 1.01 | 1.01 | CC 0.99 | CT 1.00 | TT 1.01 |
| rs941764 | 14 | A/G | 0.7 | 1.1 | 1.14 | AA 0.87 | AG 0.96 | GG 1.06 |
| rs3803662 | 16 | G/A | 0.51 | 0.99 | 0.99 | GG 1.01 | GA 1.00 | AA 0.99 |
| rs17817449 | 16 | T/G | 0.6 | 1.05 | 1.06 | TT 0.94 | TG 0.99 | GG 1.04 |
| rs11075995 | 16 | A/T | 0.18 | 1.07 | 1.03 | AA 0.98 | AT 1.04 | TT 1.12 |
| rs13329835 | 16 | A/G | 0.63 | 1.08 | 1.10 | AA 0.91 | AG 0.98 | GG 1.06 |
| rs6504950 | 17 | G/A | 0.65 | 1.06 | 1.08 | GG 0.93 | GA 0.98 | AA 1.04 |
| rs527616 | 18 | G/C | 0.86 | 0.98 | 0.97 | GG 1.04 | GC 1.01 | CC 0.99 |
| rs1436904 | 18 | T/G | 0.75 | 0.98 | 0.97 | TT 1.03 | TG 1.01 | GG 0.99 |
| rs2363956 | 19 | | | | | | | |
| rs8170 | 19 | G/A | 0.19 | 1.13 | 1.05 | GG 0.95 | GA 1.08 | AA 1.22 |
| rs4808801 | 19 | A/G | 0.33 | 1.01 | 1.01 | AA 0.99 | AG 1.00 | GG 1.01 |
| rs3760982 | 19 | G/A | 0.47 | 1 | 1.00 | GG 1.00 | GA 1.00 | AA 1.00 |
| rs2284378 | 20 | C/T | 0.16 | 1.06 | 1.02 | CC 0.98 | CT 1.04 | TT 1.10 |
| rs2823093 | 21 | G/A | 0.57 | 1.03 | 1.03 | GG 0.97 | GA 1.00 | AA 1.03 |
| rs17879961 | 22 | | | | | | | |
| rs132390 | 22 | T/C | 0.052 | 0.88 | 0.99 | TT 1.01 | TC 0.89 | CC 0.78 |
| rs6001930 | 22 | T/C | 0.13 | 1.02 | 1.01 | TT 0.99 | TC 1.01 | CC 1.04 |

TABLE 11

Hispanic SNPs (n = 82). Alleles represented as major/minor (eg for rs616488 A is the common allele and G less common). OR minor allele numbers below 1 means the minor allele is not the risk allele, whereas when above 1 the minor allele is the risk allele.

| SNP | Chromosome | Alleles | Minor allele frequency | OR Minor Allele | μ | Adjusted Risk Score | | |
|---|---|---|---|---|---|---|---|---|
| rs616488 | 1 | A/G | 0.33 | 0.9417 | 0.96 | AA 1.04 | GA 0.98 | GG 0.92 |
| rs11552449 | 1 | C/T | 0.17 | 1.0810 | 1.03 | CC 0.97 | TC 1.05 | TT 1.14 |
| rs11249433 | 1 | A/G | 0.40 | 1.0993 | 1.08 | AA 0.93 | GA 1.02 | GG 1.12 |
| rs6678914 | 1 | G/A | 0.414 | 0.9890 | 0.99 | GG 1.01 | AG 1.00 | AA 0.99 |
| rs4245739 | 1 | A/C | 0.258 | 1.0291 | 1.02 | AA 0.99 | CA 1.01 | CC 1.04 |
| rs12710696 | 2 | G/A | 0.357 | 1.0387 | 1.03 | GG 0.97 | AG 1.01 | AA 1.05 |
| rs4849887 | 2 | C/T | 0.098 | 0.9187 | 0.98 | CC 1.02 | TC 0.93 | TT 0.86 |
| rs2016394 | 2 | G/A | 0.48 | 0.9504 | 0.95 | GG 1.05 | AG 1.00 | AA 0.95 |
| rs1550623 | 2 | A/G | 0.16 | 0.9445 | 0.98 | AA 1.02 | GA 0.96 | GG 0.91 |
| rs1045485 | 2 | G/C | 0.13 | 0.9644 | 0.99 | GG 1.01 | CG 0.97 | CC 0.94 |
| rs13387042 | 2 | A/G | 0.49 | 0.8794 | 0.89 | AA 1.13 | GA 0.99 | GG 0.87 |
| rs16857609 | 2 | C/T | 0.26 | 1.0721 | 1.04 | CC 0.96 | TC 1.03 | TT 1.11 |
| rs6762644 | 3 | A/G | 0.4 | 1.0661 | 1.05 | AA 0.95 | GA 1.01 | GG 1.08 |
| rs4973768 | 3 | C/T | 0.47 | 1.0938 | 1.09 | CC 0.92 | TC 1.00 | TT 1.10 |
| rs12493607 | 3 | G/C | 0.35 | 1.0529 | 1.04 | GG 0.96 | CG 1.01 | CC 1.07 |
| rs7696175 | 4 | T/C | 0.38 | 1.14 | 1.11 | TT 0.90 | CT 1.03 | CC 1.17 |
| rs9790517 | 4 | C/T | 0.23 | 1.0481 | 1.02 | CC 0.98 | TC 1.03 | TT 1.07 |

TABLE 11-continued

Hispanic SNPs (n = 82). Alleles represented as major/minor (eg for rs616488 A is the common allele and G less common). OR minor allele numbers below 1 means the minor allele is not the risk allele, whereas when above 1 the minor allele is the risk allele.

| SNP | Chromosome | Alleles | Minor allele frequency | OR Minor Allele | μ | Adjusted Risk Score | | |
|---|---|---|---|---|---|---|---|---|
| rs6828523 | 4 | C/A | 0.13 | 0.9056 | 0.98 | CC 1.03 | AC 0.93 | AA 0.84 |
| rs4415084 | 5 | | | | | | | |
| rs10069690 | 5 | C/T | 0.26 | 1.0242 | 1.01 | CC 0.99 | TC 1.01 | TT 1.04 |
| rs7726159 | 5 | C/A | 0.338 | 1.0359 | 1.02 | CC 0.98 | AC 1.01 | AA 1.05 |
| rs2736108 | 5 | C/T | 0.292 | 0.9379 | 0.96 | CC 1.04 | TC 0.97 | TT 0.91 |
| rs10941679 | 5 | A/G | 0.25 | 1.1198 | 1.06 | AA 0.94 | GA 1.06 | GG 1.18 |
| rs889312 | 5 | A/C | 0.28 | 1.1176 | 1.07 | AA 0.94 | CA 1.05 | CC 1.17 |
| rs10472076 | 5 | T/C | 0.38 | 1.0419 | 1.03 | TT 0.97 | CT 1.01 | CC 1.05 |
| rs2067980 | 5 | G/A | 0.16 | 1 | 1.00 | GG 1.00 | AG 1.00 | AA 1.00 |
| rs1353747 | 5 | T/G | 0.095 | 0.9213 | 0.99 | TT 1.02 | GT 0.94 | GG 0.86 |
| rs1432679 | 5 | A/G | 0.43 | 1.0670 | 1.06 | AA 0.94 | GA 1.01 | GG 1.08 |
| rs11242675 | 6 | T/C | 0.39 | 0.9429 | 0.96 | TT 1.05 | CT 0.99 | CC 0.93 |
| rs204247 | 6 | A/G | 0.43 | 1.0503 | 1.04 | AA 0.96 | GA 1.01 | GG 1.06 |
| rs17529111 | 6 | A/G | 0.218 | 1.0457 | 1.02 | AA 0.98 | GA 1.03 | GG 1.07 |
| rs2180341 | 6 | G/A | 0.23 | 0.9600 | 0.98 | GG 1.02 | AG 0.98 | AA 0.94 |
| rs9485370 | 6 | | | | | | | |
| rs12662670 | 6 | T/G | 0.073 | 1.1392 | 1.02 | TT 0.98 | GT 1.12 | GG 1.27 |
| rs3757318 | 6 | | | | | | | |
| rs2046210 | 6 | G/A | 0.34 | 1.0471 | 1.03 | GG 0.97 | AG 1.01 | AA 1.06 |
| rs17157903 | 7 | T/C | 0.09 | 0.93 | 0.99 | TT 1.01 | CT 0.94 | CC 0.88 |
| rs720475 | 7 | G/A | 0.25 | 0.9452 | 1.00 | GG 1.03 | AG 0.97 | AA 0.92 |
| rs9693444 | 8 | C/A | 0.32 | 1.0730 | 1.05 | CC 0.95 | AC 1.02 | AA 1.10 |
| rs6472903 | 8 | T/G | 0.18 | 0.9124 | 0.97 | Tr 1.03 | GT 0.94 | GG 0.86 |
| rs2943559 | 8 | A/G | 0.07 | 1.1334 | 1.02 | AA 0.98 | GA 1.11 | GG 1.26 |
| rs13281615 | 8 | A/G | 0.41 | 1.0950 | 1.08 | AA 0.93 | GA 1.01 | GG 1.11 |
| rs11780156 | 8 | C/T | 0.16 | 1.0691 | 1.02 | CC 0.98 | TC 1.05 | TT 1.12 |
| rs1011970 | 9 | G/T | 0.17 | 1.0502 | 1.02 | GG 0.98 | TG 1.03 | TT 1.08 |
| rs10759243 | 9 | C/A | 0.39 | 1.0542 | 1.04 | CC 0.96 | AC 1.01 | AA 1.07 |
| rs865686 | 9 | T/G | 0.38 | 0.8985 | 0.92 | TT 1.08 | GT 0.97 | GG 0.87 |
| rs2380205 | 10 | C/T | 0.44 | 0.9771 | 0.98 | CC 1.02 | TC 1.00 | TT 0.97 |
| rs7072776 | 10 | G/A | 0.29 | 1.0581 | 1.03 | GG 0.97 | AG 1.02 | AA 1.08 |
| rs11814448 | 10 | A/C | 0.02 | 1.2180 | 1.01 | AA 0.99 | CA 1.21 | CC 1.47 |
| rs10822013 | 10 | | | | | | | |
| rs10995190 | 10 | G/A | 0.16 | 0.8563 | 0.95 | GG 1.05 | AG 0.90 | AA 0.77 |
| rs704010 | 10 | C/T | 0.38 | 1.0699 | 1.05 | CC 0.95 | TC 1.02 | TT 1.09 |
| rs7904519 | 10 | A/G | 0.46 | 1.0584 | 1.05 | AA 0.95 | GA 1.00 | GG 1.06 |
| rs2981579 | 10 | G/A | 0.4 | 1.2524 | 1.21 | GG 0.83 | AG 1.03 | AA 1.29 |
| rs2981582 | 10 | T/C | 0.42 | 1.1900 | 1.17 | TT 0.86 | CT 1.02 | CC 1.21 |
| rs11199914 | 10 | C/T | 0.32 | 0.9400 | 0.96 | CC 1.04 | TC 0.98 | TT 0.92 |
| rs3817198 | 11 | T/C | 0.31 | 1.0744 | 1.05 | TT 0.96 | CT 1.03 | CC 1.10 |
| rs3903072 | 11 | G/T | 0.47 | 0.9442 | 0.95 | GG 1.05 | TG 1.00 | TT 0.94 |
| rs554219 | 11 | C/G | 0.112 | 1.1238 | 1.03 | CC 0.97 | GC 1.09 | GG 1.23 |
| rs614367 | 11 | | | | | | | |
| rs78540526 | 11 | C/T | 0.032 | 1.1761 | 1.01 | CC 0.99 | TC 1.16 | TT 1.37 |
| rs75915166 | 11 | C/A | 0.059 | 1.0239 | 1.00 | CC 1.00 | AC 1.02 | AA 1.05 |
| rs11820646 | 11 | C/T | 0.41 | 0.9563 | 0.96 | CC 1.04 | TC 0.99 | TT 0.95 |
| rs12422552 | 12 | G/C | 0.26 | 1.0327 | 1.02 | GG 0.98 | CG 1.02 | CC 1.05 |
| rs10771399 | 12 | A/G | 0.12 | 0.8629 | 0.97 | AA 1.03 | GA 0.89 | GG 0.77 |
| rs17356907 | 12 | A/G | 0.3 | 0.9078 | 0.95 | AA 1.06 | GA 0.96 | GG 0.87 |
| rs1292011 | 12 | A/G | 0.42 | 0.9219 | 0.94 | AA 1.07 | GA 0.99 | GG 0.91 |
| rs11571833 | 13 | A/T | 0.008 | 1.2609 | 1.00 | AA 1.00 | TA 1.26 | TT 1.58 |
| rs2236007 | 14 | G/A | 0.21 | 0.9203 | 0.97 | GG 1.03 | AG 0.95 | AA 0.88 |
| rs999737 | 14 | C/T | 0.23 | 0.9239 | 0.97 | CC 1.04 | TC 0.96 | TT 0.88 |
| rs2588809 | 14 | C/T | 0.16 | 1.0667 | 1.02 | CC 0.98 | TC 1.04 | TT 1.11 |
| rs941764 | 14 | A/G | 0.34 | 1.0636 | 1.04 | AA 0.96 | GA 1.02 | GG 1.08 |
| rs3803662 | 16 | G/A | 0.26 | 1.2257 | 1.12 | GG 0.89 | AG 1.09 | AA 1.34 |
| rs17817449 | 16 | T/G | 0.4 | 0.9300 | 0.94 | TT 1.06 | GT 0.98 | GG 0.92 |
| rs11075995 | 16 | A/T | 0.241 | 1.0368 | 1.02 | AA 0.98 | TA 1.02 | TT 1.06 |
| rs13329835 | 16 | A/G | 0.22 | 1.0758 | 1.03 | AA 0.97 | GA 1.04 | GG 1.12 |
| rs6504950 | 17 | G/A | 0.28 | 0.9340 | 0.96 | GG 1.04 | AG 0.97 | AA 0.91 |
| rs527616 | 18 | G/C | 0.38 | 0.9573 | 0.97 | GG 1.03 | CG 0.99 | CC 0.95 |
| rs1436904 | 18 | T/G | 0.4 | 0.9466 | 0.96 | TT 1.04 | GT 0.99 | GG 0.94 |
| rs2363956 | 19 | G/T | 0.487 | 1.0264 | 1.03 | GG 0.97 | TG 1.00 | TT 1.03 |
| rs8170 | 19 | G/A | 0.19 | 1.0314 | 1.01 | GG 0.99 | AG 1.02 | AA 1.05 |
| rs4808801 | 19 | A/G | 0.35 | 0.9349 | 0.95 | AA 1.05 | GA 0.98 | GG 0.92 |
| rs3760982 | 19 | G/A | 0.46 | 1.0553 | 1.05 | GG 0.95 | AG 1.00 | AA 1.06 |
| rs2284378 | 20 | | | | | | | |
| rs2823093 | 21 | G/A | 0.27 | 0.9274 | 0.96 | GG 1.04 | AG 0.96 | AA 0.89 |
| rs17879961 | 22 | A/G | 0.005 | 1.3632 | 1.00 | AA 1.00 | GA 1.36 | GG 1.85 |
| rs132390 | 22 | T/C | 0.036 | 1.1091 | 1.01 | TT 0.99 | CT 1.10 | CC 1.22 |
| rs6001930 | 22 | T/C | 0.11 | 1.1345 | 1.03 | TT 0.97 | CT 1.10 | CC 1.25 |

Example 2—Risk Thresholds

Breast cancer risk assessment is important as it allows the identification of women who are at elevated risk who may benefit from either targeted screening or preventative measures (De la Cruz, 2014: Advani and Morena-Aspitia, 2014). Both genetic and environmental factors are thought to play a role in multifactoral susceptibility to breast cancer (Lichtenstein et al., 2000; Mahoney et al., 2008). In order to optimally assess risk, both components are considered together. Currently, breast cancer risk is often assessed by utilizing the National Cancer Institute's (NCI) Breast Cancer Risk Assessment Tool (BCRAT), often referred to as the "Gail Model" (Gail et al., 1989: Costantino et al., 1999: Rockhill et al., 2001). The BCRAT incorporates several risk factors related to personal history and also incorporates some family history information.

The current model takes the information provided by the ordering physician to calculate a Gail score, and combines it with the patient's common genetic markers for breast cancer to produce Integrated Lifetime (Example shown in FIG. 1) and 5-Year patient risk (Example shown in FIG. 2) assessments for breast cancer. It is recommended that a patient receive appropriate genetic or clinical counseling to explain the implications of the test results. American Cancer Society (ACS) guidelines recommend screening breast MRI and mammography for women at high risk (20% lifetime risk). American Society of Clinical Oncology (ASCO) suggest women at high risk (GAIL index>1.66% for 5-year risk) may be offered an estrogen receptor therapy to reduce their risk.

The current test provides additional important information about a woman's risk of developing breast cancer by assessing genetic information from a cheek cell sample. The test detects SNPs. At least 70 of these distinct genetic locations are analysed (genotyped), each of which has been shown reproducibly to modify an individual's odds of developing breast cancer. The test combines the information from all SNPs in the panel because the scientific validation studies support a simple multiplicative model for combining the SNP risks (Mealifle et al., 2010).

Example 3—Combination of SNP Risk Scores with Breast Cancer Risk Models

There are several popular breast cancer risk prediction models. These include BOADICEA (Antonio et al., 2008 and 2009) and BRCAPRO (Chen et al., 2004; Mazzola et al., 2014: Parmigianin et al., 1998), both of which are based on pedigree data for breast and ovarian cancer; the Gail Model (BCRAT) (Costatino et al., 1999; Gail et al., 1989), which is based on established risk factors for breast cancer and family history represented b) the number of first-degree relatives with breast cancer: and the Tyrer-Cuzick Model (IBIS) (Tyrer et al., 2004), which combines information on familial and personal risk factors for breast cancer. At an individual level, all of these risk prediction models must have good discriminatory accuracy to be able to provide information that is clinically useful to help a woman make decisions on screening or prevention that are tailored to her specific circumstances.

The present inventors tested the ability of a 77 SNP panel to improve the discriminatory accuracy of the Gail, Tyrer-Cuzick, BOADICEA and BRCAPRO models in a Caucasian cohort.

For each risk prediction model, the five-year clinical risk of invasive breast cancer was calculated. For BCRAT, in accordance with the model's design, risk predictions were restricted to women aged 35 years and older. A SNP risk score was calculated using published estimates of the odds ratio (OR) per allele and risk allele frequencies (p) assuming independence of additive risks on the log OR scale. Cases and controls were recruited to the Australian Breast Cancer Family Registry (ABCFR), which were included in a population-based case-control-family study. Briefly, between 1992 and 1998, the ABCFR used the state population-based cancer registries in New South Wales and Victoria to recruit women who had incident diagnoses of histologically-confirmed first primary invasive breast cancer. Recruitment was limited to women living in metropolitan Sydney or Melbourne. and included all women aged less than 40 years at diagnosis and a random sample of women aged 40-59 years at diagnosis. Controls were randomly selected from the electoral roll (for which registration is compulsory for all adult Australian citizens) and were from the same geographic regions and had the same age distribution as the cases. For each SNP, the unscaled population average risks were calculated as $I/\mu$, $OR/\mu$ and $OR2/\mu$ for the three genotypes. The SNP risk score was then calculated b, multiplying the adjusted risk values for each of the 77 SNPs (Dite et al., 2013). For each risk prediction model, a combined risk score was calculated by multiplying the SNP risk score by the model's predicted five-year risk. Discrimination was measured by calculating the area under the receiver operating characteristic curve (AUC).

Table 12 shows that for each of the four risk prediction models, the combined risk score gave higher discrimination than the risk scores alone.

Example 4—Calculation of Risk

This example is a hypothetical case in which the inventors have assumed that all factors remain constant, except for ethnicity of the woman. In this example the three women (one Caucasian, one African-American and one Hispanic) have the following characteristics—45 year old, age at first period was 12, first child at 26, no first-degree relatives with breast cancer, and have not had an) positive breast biopsies.

Table 13 outlines the genotypes of the three women, whereas Table 14 provides details of the risk calculation.

TABLE 12

Area under the receiver operating characteristic curve (AUC) and 95% confidence interval (CI) for each of the risk scores.

| Risk Algorithm | AUC | (95% CI) |
|---|---|---|
| Gail (BCRAT) | 0.64 | (0.60, 0.68) |
| Tyrer-Cuzick (IBIS) | 0.57 | (0.54, 0.60) |
| BOADICEA | 0.66 | (0.63, 0.70) |
| BRCAPRO | 0.63 | (0.60, 0.67) |
| Gail × SNP | 0.66 | (0.62, 0.70) |
| Tyrer-Cuzick × SNP | 0.63 | (0.59, 0.66) |
| BOADICEA × SNP | 0.69 | (0.66, 0.73) |
| BRCAPRO × SNP | 0.68 | ((0.65, 0.71) |

TABLE 14

Risk calculations using the genotype scores from Table 13.

| | Gail 5-Year Risk | Gail Lifetime Risk | SNP risk | Combined SNP × 5-Year Risk | Combined SNP × Lifetime Risk |
|---|---|---|---|---|---|
| Caucasian | 0.9% | 10.6% | 5.75 | 5.175% | 60.95% |
| African American | 0.9% | 9.3% | 1.09 | 0.98% | 10.14% |
| Hispanic | 0.6% | 7.5% | 0.67 | 0.40% | 5.03% |

The impact of the genotypic risk is evidenced when we multiply the genotypic and clinical risk (Gail Score) together. In the above instance, the Caucasian has their 5-Year risk elevated to 5.175% and would be offered Tamoxifen chemoprevention. She also has her Lifetime risk elevated to 60.95% and would be offered annual MRI screening.

The African American has a genotypic risk score close to 1 and her risk remains close to average (5-year risk=0.985 and lifetime risk=10.14%).

The Hispanic woman has a genotypic risk of 0.67 (ie, this genotype is protective) and her subsequent 5-year risk is reduced to 0.40% and her lifetime risk reduced to 5.03%.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The present application claims priority from AU 2014903898 filed 30 Sep. 2014, the disclosures of which are incorporated herein by reference.

The invention claimed is:

1. A method for producing a number which represents the risk of a human self-reported Caucasian female subject developing breast cancer, the method comprising:

a) obtaining the odds ratio (OR) of association with breast cancer of 77 single nucleotide polymorphisms (SNPs) consisting of SNPs rs616488, rs11552449, rs11249433, rs6678914, rs4245739, rs12710696, rs4849887, rs2016394, rs1550623, rs1045485, rs13387042, rs16857609, rs6762644, rs4973768, rs12493607, rs9790517, rs6828523, rs10069690, rs7726159, rs2736108, rs10941679, rs889312, rs10472076, rs1353747, rs1432679, rs11242675, rs204247, rs17529111, rs12662670, rs2046210, rs720475, rs9693444, rs6472903, rs2943559, rs13281615, rs11780156, rs1011970, rs10759243, rs865686, rs2380205, rs7072776, rs11814448, rs10995190, rs704010, rs7904519, rs2981579, rs11199914, rs3817198, rs3903072, rs554219, rs78540526, rs75915166, rs11820646, rs12422552, rs10771399, rs17356907, rs1292011, rs11571833, rs2236007, rs999737, rs2588809, rs941764, rs3803662, rs17817449, rs11075995, rs13329835, rs6504950, rs527616, rs1436904, rs2363956, rs8170, rs4808801, rs3760982, rs2823093, rs17879961, rs132390, and rs6001930;

b) obtaining the identity of alleles present in the genome of the female subject at a panel of SNPs consisting of the 77 SNPs;

c) determining an adjusted risk score for each of the 77 SNPs of the female subject, where:
   (i) if two major alleles are present at the SNP, then the adjusted risk score for the SNP is $1/\mu$,
   (ii) if one major and one minor allele are present at the SNP, then the adjusted risk score for the SNP is $OR/\mu$,
   (iii) if two minor alleles are present at the SNP, then the adjusted risk score for the SNP is $OR^2/\mu$, and
   (iv) if the genotype is missing for the SNP, then the adjusted risk score for the SNP is 1,
   where $\mu=(1-p)^2+2p(1-p)OR+p^2OR^2$, wherein OR is the odds ratio of a minor allele at the given SNP and p is the frequency of the minor allele among self-reported Caucasian females;

d) multiplying together the adjusted risk score for each of the 77 SNPs of the female subject to produce a genetic risk score of the female subject;

e) obtaining a clinical risk assessment of the female subject; and f) combining the clinical risk assessment of the female subject with the genetic risk score of the female subject, to produce a number which represents the risk of the human self-reported Caucasian female subject developing breast cancer relative to the average risk of developing breast cancer in the population to which the human self-reported Caucasian female subject belongs.

2. The method of claim 1, wherein the female has not had breast cancer, lobular carcinoma or ductal carcinoma.

3. The method of claim 1, wherein the female has had a biopsy of the breast.

4. The method according to claim 1, wherein the results of the risk assessment indicate that the female should be subjected to more frequent screening and/or prophylactic anti-breast cancer therapy.

5. A computer implemented method for producing a number which represents the risk of a human self-reported Caucasian female subject developing breast cancer, the method operable in a computing system comprising a processor and a memory, the method comprising:
   (a) receiving data comprising the identity of alleles present in the genome of the female subject at a panel of single nucleotide polymorphisms (SNPs) consisting of SNPs rs616488, rs11552449, rs11249433, rs6678914, rs4245739, rs12710696, rs4849887, rs2016394, rs1550623, rs1045485, rs13387042, rs16857609, rs6762644, rs4973768, rs12493607, rs9790517, rs6828523, rs10069690, rs7726159, rs2736108, rs10941679, rs889312, rs10472076, rs1353747, rs1432679, rs11242675, rs204247, rs17529111, rs12662670, rs2046210, rs720475, rs9693444, rs6472903, rs2943559, rs13281615, rs11780156, rs1011970, rs10759243, rs865686, rs2380205, rs7072776, rs11814448, rs10995190, rs704010, rs7904519, rs2981579, rs11199914, rs3817198, rs3903072, rs554219, rs78540526, rs75915166, rs11820646, rs12422552, rs10771399, rs17356907, rs1292011, rs11571833, rs2236007, rs999737, rs2588809, rs941764, rs3803662, rs17817449, rs11075995, rs13329835, rs6504950, rs527616, rs1436904, rs2363956, rs8170, rs4808801, rs3760982, rs2823093, rs17879961, rs132390, and rs6001930;

(b) processing the data by determining an adjusted risk score for each of the 77 SNPs of the female subject, where:
   (i) if two major alleles are present at the SNP, then the adjusted risk score for the SNP is $1/\mu$,
   (ii) if one major and one minor allele are present at the SNP, then the adjusted risk score for the SNP is $OR/\mu$,
   (iii) if two minor alleles are present at the SNP, then the adjusted risk score for the SNP is $OR^2/\mu$, and
   (iv) if the genotype is missing for the SNP, then the adjusted risk score for the SNP is 1,
   where $\mu=(1-p)^2+2p(1-p)OR+p^2OR^2$, wherein OR is the odds ratio of association with breast cancer of the 77 SNPs of a minor allele at the given SNP and p is the frequency of the minor allele among self-reported Caucasian females;

(c) processing the data by multiplying together the adjusted risk score for each of the 77 SNPs of the female subject to produce a genetic risk score of the female subject;

(d) receiving data comprising a clinical risk assessment of the female subject; and (e) combining the genetic risk score of the female subject with the clinical risk assessment of the female subject to produce a number which represents the risk of the human self-reported Caucasian female subject developing breast cancer relative to the average risk of developing breast cancer in the population to which the human self-reported Caucasian female subject belongs.

6. The method of claim 5, wherein the female has not had breast cancer, lobular carcinoma or ductal carcinoma.

7. The method of claim 5, wherein the female has had a biopsy of the breast.

8. The method according to claim 5, wherein the results of the risk assessment indicate that the female should be subjected to more frequent screening and/or prophylactic anti-breast cancer therapy.

9. The method of claim 1, further comprising identifying the human female subject as having an increased genetic risk of developing breast cancer relative to the average genetic risk of developing breast cancer in the population to which the human female subject belongs if the genetic risk score is greater than 1.

10. The method of claim 1, wherein the clinical risk assessment is obtained using the Tyrer-Cuzick Model.

11. A method for producing a number which represents the risk of a human self-reported Caucasian female subject developing breast cancer, the method comprising:
   a) obtaining the odds ratio (OR) of association with breast cancer of 77 single nucleotide polymorphisms (SNPs) consisting of SNPs rs616488, rs11552449, rs11249433, rs6678914, rs4245739, rs12710696, rs4849887, rs2016394, rs1550623, rs1045485, rs13387042, rs16857609, rs6762644, rs4973768, rs12493607, rs9790517, rs6828523, rs10069690, rs7726159, rs2736108, rs10941679, rs889312, rs10472076, rs1353747, rs1432679, rs11242675, rs204247, rs17529111, rs12662670, rs2046210, rs720475, rs9693444, rs6472903, rs2943559, rs13281615, rs11780156, rs1011970, rs10759243, rs865686, rs2380205, rs7072776, rs11814448, rs10995190, rs704010, rs7904519, rs2981579, rs11199914, rs3817198, rs3903072, rs554219, rs78540526, rs75915166, rs11820646, rs12422552, rs10771399, rs17356907, rs1292011, rs11571833, rs2236007, rs999737, rs2588809, rs941764, rs3803662, rs17817449, rs11075995, rs13329835, rs6504950, rs527616, rs1436904, rs2363956, rs8170, rs4808801, rs3760982, rs2823093, rs17879961, rs132390, and rs6001930 by logistic regression analysis of cases identified as having histologically-confirmed first primary invasive breast cancer and controls randomly selected from the same geographic regions as the cases and having the same age distribution as the cases;

b) obtaining the identity of alleles present in the genome of the female subject at a panel of SNPs consisting of the 77 SNPs;

c) determining an adjusted risk score for each of the 77 SNPs of the female subject, where:
  (i) if two major alleles are present at the SNP, then the adjusted risk score for the SNP is $1/\mu$,
  (ii) if one major and one minor allele are present at the SNP, then the adjusted risk score for the SNP is $OR/\mu$,
  (iii) if two minor alleles are present at the SNP, then the adjusted risk score for the SNP is $OR^2/\mu$, and
  (iv) if the genotype is missing for the SNP, then the adjusted risk score for the SNP is 1,
  where $\mu=(1-p)^2+2p(1-p)OR+p^2OR^2$, wherein OR is the odds ratio of a minor allele at the given SNP and p is the frequency of the minor allele among self-reported Caucasian females;

d) multiplying together the adjusted risk score for each of the 77 SNPs of the female subject to produce a genetic risk score of the female subject;

e) obtaining a clinical risk assessment of the female subject; and f) combining the clinical risk assessment of the female subject with the genetic risk score of the female subject, to produce a number which represents the risk of the human self-reported Caucasian female subject developing breast cancer relative to the average risk of developing breast cancer in the population to which the human self-reported Caucasian female subject belongs.

12. The method of claim 11, wherein the female has not had breast cancer, lobular carcinoma or ductal carcinoma.

13. The method of claim 11, wherein the female has had a biopsy of the breast.

14. The method according to claim 11, wherein the results of the risk assessment indicate that the female should be subjected to more frequent screening and/or prophylactic anti-breast cancer therapy.

15. The method of claim 11, wherein the cases and controls are aged 35 years or older.

16. The method of claim 11, wherein the clinical risk assessment is obtained using the Tyrer-Cuzick Model.

17. The method of claim 1, wherein the combining the clinical risk assessment of the female subject with the genetic risk score of the female subject in step (f) comprises multiplying the clinical risk assessment of the female subject with the genetic risk score of the female subject.

18. The method of claim 5, wherein the combining the clinical risk assessment of the female subject with the genetic risk score of the female subject in step (e) comprises multiplying the clinical risk assessment of the female subject with the genetic risk score of the female subject.

19. The method of claim 11, wherein the combining the clinical risk assessment of the female subject with the genetic risk score of the female subject in step (f) comprises multiplying the clinical risk assessment of the female subject with the genetic risk score of the female subject.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Homo sapiens

<400> SEQUENCE: 1
tatgggaagg agtcgttgag                                              20

<210> SEQ ID NO 2
<211> LENGTH: 20
<212> TYPE: DNA
<213> ORGANISM: Homo sapiens

<400> SEQUENCE: 2
ctgaatcact ccttgccaac                                              20

<210> SEQ ID NO 3
<211> LENGTH: 20
<212> TYPE: DNA
<213> ORGANISM: Homo sapiens

<400> SEQUENCE: 3
caaaatgatc tgactactcc                                              20

<210> SEQ ID NO 4
<211> LENGTH: 20
<212> TYPE: DNA
<213> ORGANISM: Homo sapiens

<400> SEQUENCE: 4
tgaccagtgc tgtatgtatc                                              20

<210> SEQ ID NO 5
<211> LENGTH: 20
<212> TYPE: DNA
<213> ORGANISM: Homo sapiens

<400> SEQUENCE: 5
tctcacctga taccagattc                                              20

<210> SEQ ID NO 6
<211> LENGTH: 20
<212> TYPE: DNA
<213> ORGANISM: Homo sapiens

```
<400> SEQUENCE: 6
tctctcctta atgcctctat                                              20

<210> SEQ ID NO 7
<211> LENGTH: 20
<212> TYPE: DNA
<213> ORGANISM: Homo sapiens

<400> SEQUENCE: 7
actgctgcgg gttcctaaag                                              20

<210> SEQ ID NO 8
<211> LENGTH: 21
<212> TYPE: DNA
<213> ORGANISM: Homo sapiens

<400> SEQUENCE: 8
ggaagattcg attcaacaag g                                            21

<210> SEQ ID NO 9
<211> LENGTH: 19
<212> TYPE: DNA
<213> ORGANISM: Homo sapiens

<400> SEQUENCE: 9
ggtaactatg aatctcatc                                               19

<210> SEQ ID NO 10
<211> LENGTH: 20
<212> TYPE: DNA
<213> ORGANISM: Homo sapiens

<400> SEQUENCE: 10
aaaaagcaga gaaagcaggg                                              20

<210> SEQ ID NO 11
<211> LENGTH: 20
<212> TYPE: DNA
<213> ORGANISM: Homo sapiens

<400> SEQUENCE: 11
agatgatctc tgagatgccc                                              20

<210> SEQ ID NO 12
<211> LENGTH: 20
<212> TYPE: DNA
<213> ORGANISM: Homo sapiens

<400> SEQUENCE: 12
ccagggtttg tctaccaaag                                              20

<210> SEQ ID NO 13
<211> LENGTH: 19
<212> TYPE: DNA
<213> ORGANISM: Homo sapiens

<400> SEQUENCE: 13
aatcacttaa aacaagcag                                               19

<210> SEQ ID NO 14
<211> LENGTH: 20
<212> TYPE: DNA
<213> ORGANISM: Homo sapiens
```

```
<400> SEQUENCE: 14 cacataccte tacctctage                                               20

<210> SEQ ID NO 15
<211> LENGTH: 19
<212> TYPE: DNA
<213> ORGANISM: Homo sapiens

<400> SEQUENCE: 15
ttccctagtg gagcagtgg                                                19

<210> SEQ ID NO 16
<211> LENGTH: 20
<212> TYPE: DNA
<213> ORGANISM: Homo sapiens

<400> SEQUENCE: 16
ctttcttcgc aaatgggtgg                                               20

<210> SEQ ID NO 17
<211> LENGTH: 20
<212> TYPE: DNA
<213> ORGANISM: Homo sapiens

<400> SEQUENCE: 17
gcactcatcg ccacttaatg                                               20

<210> SEQ ID NO 18
<211> LENGTH: 20
<212> TYPE: DNA
<213> ORGANISM: Homo sapiens

<400> SEQUENCE: 18
gaacagctaa accagaacag                                               20

<210> SEQ ID NO 19
<211> LENGTH: 20
<212> TYPE: DNA
<213> ORGANISM: Homo sapiens

<400> SEQUENCE: 19
atcactctta tttctccccc                                               20

<210> SEQ ID NO 20
<211> LENGTH: 20
<212> TYPE: DNA
<213> ORGANISM: Homo sapiens

<400> SEQUENCE: 20
tgagtcactg tgctaaggag                                               20
```